United States Patent
Prat Quinones et al.

(10) Patent No.: US 9,643,961 B2
(45) Date of Patent: *May 9, 2017

(54) CYCLOHEXYLAMINE DERIVATIVES HAVING β2 ADRENERGIC ANTAGONIST AND M3 MUSCARINIC ANTAGONIST ACTIVITIES

(71) Applicant: Almirall, S.A., Barcelona (ES)

(72) Inventors: Maria Prat Quinones, Barcelona (ES); Silvia Fonquerna Pou, Barcelona (ES); Carlos Puig Duran, Barcelona (ES); Wenceslao Lumeras Amador, Barcelona (ES); Jose Aiguade Bosch, Barcelona (ES); Juan Francisco Caturla Javaloyes, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,926

(22) Filed: Mar. 14, 2016

(65) Prior Publication Data

US 2016/0264557 A1   Sep. 15, 2016

Related U.S. Application Data

(63) Continuation of application No. 13/697,060, filed as application No. PCT/EP2011/002376 on May 13, 2011, now Pat. No. 9,315,463.

(60) Provisional application No. 61/365,045, filed on Jul. 16, 2010.

(30) Foreign Application Priority Data

May 13, 2010 (EP) ..................... 10382118

(51) Int. Cl.
| | | |
|---|---|---|
| C07D 215/26 | (2006.01) | |
| C07D 409/14 | (2006.01) | |
| A61K 31/4709 | (2006.01) | |
| C07D 405/12 | (2006.01) | |
| C07D 409/12 | (2006.01) | |
| C07D 413/14 | (2006.01) | |

(52) U.S. Cl.
CPC ........ *C07D 409/14* (2013.01); *A61K 31/4709* (2013.01); *C07D 215/26* (2013.01); *C07D 405/12* (2013.01); *C07D 409/12* (2013.01); *C07D 413/14* (2013.01)

(58) Field of Classification Search
None
See application file for complete search history.

(56) References Cited

U.S. PATENT DOCUMENTS

| 4,556,653 A | 12/1985 | Giani et al. |
| 5,397,800 A | 3/1995 | Alker et al. |
| 6,673,908 B1 | 1/2004 | Stanton, Jr. |
| 9,072,734 B2 | 7/2015 | Mitsuyama et al. |
| 9,233,108 B2 | 1/2016 | Aiguade Bosch et al. |
| 9,315,463 B2 | 4/2016 | Prat Quinones et al. |
| 2012/0046467 A1 | 2/2012 | Mitsuyama et al. |
| 2013/0053359 A1 | 2/2013 | Prat Quinones et al. |
| 2013/0281415 A9 | 10/2013 | Prat Quinones et al. |
| 2014/0303127 A1 | 10/2014 | Bosch et al. |
| 2014/0378421 A1 | 12/2014 | Bosch et al. |
| 2015/0329535 A1 | 11/2015 | Sole Feu et al. |
| 2016/0009698 A1 | 1/2016 | Julia Jane et al. |
| 2016/0015704 A1 | 1/2016 | Aparici Virgili et al. |
| 2016/0143915 A1 | 5/2016 | Aiguade Bosch et al. |
| 2016/0166566 A1 | 6/2016 | Julia Jane et al. |
| 2016/0175295 A1 | 6/2016 | Aparici Virgili et al. |
| 2016/0200718 A1 | 7/2016 | Aiguade Bosch et al. |

FOREIGN PATENT DOCUMENTS

| CN | 101544572 A | 9/2009 |
| EP | 0147475 | 10/1985 |
| EP | 1 078 629 | 2/2001 |
| EP | 1 894 568 | 3/2008 |
| EP | 2 386 555 | 11/2011 |
| EP | 2 426 121 | 3/2012 |
| EP | 2 592 077 | 5/2013 |
| EP | 2 592 078 | 5/2013 |
| WO | WO 98/09632 | 3/1998 |
| WO | WO 99/30703 | 6/1999 |
| WO | WO 01/14339 | 3/2001 |
| WO | WO 2004/074246 | 9/2004 |
| WO | WO 2004/074276 | 9/2004 |
| WO | WO 2004/074812 | 9/2004 |
| WO | WO 2004/089892 | 10/2004 |
| WO | WO 2004/106333 | 12/2004 |
| WO | WO 2005/080375 | 9/2005 |
| WO | WO 2005/111004 | 11/2005 |
| WO | WO 2005/123693 | 12/2005 |
| WO | WO 2006/023454 | 3/2006 |

(Continued)

OTHER PUBLICATIONS

International Search Report for PCT International Appliation No. PCT/EP2011/002376, mailed Aug. 1, 2011.
Naito, Ryo et al., "Synthesis and antimuscarinic propterties quinuclidin-3-yl 1,2,3,4-tetrahydroisoquinoline-2-carboxylate derivaties as novel muscarinic receptor antagonists." J.Med. Chem., 48:6597-6606 (2005).
Van Noord, J.A., et al., "Comparison of tiotropium once daily, formoterol twoice daily and both combined once daily in patients with COPD," Eur. Respir. J., 26:214-222 (2005).
A.D. Hughes et al., "Dual-pharmacology muscarinic antagonist and β₂ agonist molecules for the treatment of chronic obstructive pulmonary disease," Future Med. Chem., 2011, 3(13), pp. 185-1605.
A.D. Hughes et al., Multivalent dual pharmacology muscarinic antagonist and β₂ agonist (MABA) molecules for the treatment of COPD, Progress in Medicinal Chemistry, 2012, 51, pp. 71-95.

(Continued)

*Primary Examiner* — Savitha Rao
*Assistant Examiner* — Gregg Polansky
(74) *Attorney, Agent, or Firm* — Finnegan, Henderson, Farabow, Garrett & Dunner LLP

(57) ABSTRACT

The present invention relates to novel compounds having β2 adrenergic agonist and M3 muscarinic antagonist dual activity, to pharmaceutical compositions containing them, to the process for their preparation and to their use in respiratory therapies.

3 Claims, No Drawings

(56) References Cited

FOREIGN PATENT DOCUMENTS

| | | |
|---|---|---|
| WO | WO 2006/023457 | 3/2006 |
| WO | WO 2006/023460 | 3/2006 |
| WO | WO 2007/017670 | 2/2007 |
| WO | WO 2007/090859 | 8/2007 |
| WO | WO 2007/107828 | 9/2007 |
| WO | WO 2008/000483 | 1/2008 |
| WO | WO 2008/017824 | 2/2008 |
| WO | WO 2008/017827 | 2/2008 |
| WO | WO 2008/041095 | 4/2008 |
| WO | WO 2008/087437 | 7/2008 |
| WO | WO 2008/096127 | 8/2008 |
| WO | WO 2008/096129 | 8/2008 |
| WO | WO 2008/149110 | 12/2008 |
| WO | WO 2009/013244 | 1/2009 |
| WO | WO 2009/017813 | 2/2009 |
| WO | WO 2009/098448 | 8/2009 |
| WO | WO 2009/139709 | 11/2009 |
| WO | WO 2010/004517 | 1/2010 |
| WO | WO 2010/015792 | 2/2010 |
| WO | WO 2010/069504 | 6/2010 |
| WO | WO 2010/123766 | 10/2010 |
| WO | WO 2011/012897 | 2/2011 |
| WO | WO 2011/141180 | 11/2011 |
| WO | WO 2012/044825 | 4/2012 |
| WO | WO 2012/085582 | 6/2012 |
| WO | WO 2012/085583 | 6/2012 |
| WO | WO 2012/168349 | 12/2012 |
| WO | WO 2012/168359 | 12/2012 |
| WO | WO 2013/068552 | 5/2013 |
| WO | WO 2013/068554 | 5/2013 |
| WO | WO 2013/068875 | 5/2013 |
| WO | WO 2013/071009 | 5/2013 |
| WO | WO 2013/071169 | 5/2013 |
| WO | WO 2014/086924 | 6/2014 |
| WO | WO 2014/086927 | 6/2014 |
| WO | WO 2014/095920 | 6/2014 |
| WO | WO 2014/131851 | 9/2014 |
| WO | WO 2014/131852 | 9/2014 |
| WO | WO 2015/011244 | 1/2015 |
| WO | WO 2015/011245 | 1/2015 |
| WO | WO 2016/046390 | 3/2016 |

OTHER PUBLICATIONS

A.D. Hughes et al., Discovery of muscarinic acetylcholine receptor antagonist and beta-2 adrenoceptor agonist (MABA) dual pharmacology molecules, Respiratory Drug Delivery Europe, 2013, pp. 47-58.
P.J. Barnes, "Airway pharmacology," Textbook of Respiratory Medicine, 3$^{rd}$ Edition, Chapter 11, 2000, pp. 267-272.
E.C. Bateman et al., "Pharmacodynamics of GSK961081, a bifunctional molecule, in patients with COPD," Pulmonary Pharmacology and Therapeutics, 2013, 26, pp. 581-587.
P.A. Glossop et al., "Progress in the development of Inhaled, long-acting $\beta_2$-adrenoceptor agonists," Annual Reports in Medicinal Chemistry, 2006, vol. 41, pp. 237-248.
B.B. Hoffman, "Catecholamines, sympathomimetic drugs, and adrenergic receptor antagonists," Goodman and Gilman's The Pharmacological Basis of Therapeutics, 10$^{th}$ Edition, Chapter 10, 2001, pp. 215-232.
J.R. Jacobsen, "Third-generation long-acting $\beta_2$-adrenoceptor agonists: medicinal chemistry strategies employed in the identification of once-daily inhaled $\beta_2$-adrenoceptor agonsits," Future Med. Chem., 2011, 3(13), pp. 1607-1622.
A. McNamara, "Preclinical efficacy of THRX-200495, a dual pharmacology muscarinic receptor antagonist and $\beta_2$-adrenoceptor agonist (MABA)," Pulmonary Pharmacology and Therapeutics, 2012, pp. 1-7.
P. Norman, "Evaluation of WO-2012085582 and WO-2012085583 two identified MABAs backups to AZD-2115," Expert Opinion Ther. Patents 2012, 22(11), pp. 1377-1382.
P. Norman, "Novel dihydroquinoline-based MABAs: clues to the identity of LAS-190892L evaluation of WO20111411802," Expert Opinion Ther. Patents, 2012, 22(2), p. 185-192.
V. Norris et al., Bronchodilation and safety of supratherapeutic doses of salbutamol or ipratropium, bromide added to single dose GSK961081 in patients with moderate to severe COPD, Polumonary Pharmacology and Therapeutics, 2013, 26, pp. 574-580.
P.L.M.L. Wielders et al., "A new class of bronchodilator improves lung function in COPD: a trial with GSK961081," Eur. Respir Journal, 2013, 42, pp. 972-981.
Banerjee, R. et al., "Synthon robustness in saccharinate salts of some substituted pyridines," CrystEng Comm, 8:pp. 680-785 (2006).
Bastin, R.J. et al., "Salt Selection and Optimisation Procedures for Pharmaceutical New Chemical Entities," Org Process Res Dev, 4, pp. 427-435 (2000).
Chung, K.F., "p38 Mitogen-Activated Protein Kinase Pathways in Asthma and COPD," Chest 139(6): pp. 1470-1479 (2011).
Miller-Larsson, A., and Selrods, O., "Advances in Asthma and COPD Treatment: Combination Therapy with Inhaled Corticosteriods and Long-Acting $\beta2$ Agonists," Curr Pharm Des, 12(25): pp. 3261-3279 (2006).
Rogers, D.F., "Tachykinin receptor antagonist for astma and COPD," Expert Opin Ther Patents, 11(7): pp. 1097-1121 (2001).
Shan, W., et al., "Dual $\beta2$-adrenoceptor agonists-PDE4 inhibitors for the treatment of asthma and COPD," Bioorg Med Chem. Lett. 22: pp. 1523-1526 (2012).
Thorsson, L. and Gellar, D., "Factors guiding the choice of delivery device for inhaled corticosteroids in the long-term management of stable asthma and COPD: Focus on budesonide," Respir Med, 99: pp. 836-849 (2005).
Ray, Nicholas C. et al., "Muscarinic antagonist-$\beta$-adrenergic agonist dual pharmacology molecules as bronchodilators: a patent review," Informa Healthcare, vol. 19, No. 1, pp. 1-12 (2009).
International Search Report for International Application No. PCT/EP2012/072311, dated Dec. 10, 2012.
International Search Report for International Application No. PCT/EP2012/072309, dated Dec. 19, 2012.
International Search Report for International Application No. PCT/EP2013/076973, mailed Mar. 11, 2014.
International Search Report for International Application No. PCT/EP2014/053874, mailed Apr. 17, 2014.
International Search Report for International Application No. PCT/EP2014/053871, mailed Mar. 27, 2014.
International Search Report for International Application No. PCT/EP2011/002376, mailed Aug. 1, 2011.
Office Action dated Feb. 3, 2015, in U.S. Appl. No. 14/357,344.
Restriction Requirement dated Feb. 18, 2015, in U.S. Appl. No. 14/357,400.
Office Action dated Jun. 2, 2015, in U.S. Appl. No. 14/357,344.
Restriction Requirement dated Feb. 20, 2015, in U.S. Appl. No. 13/697,060.
Notice of Allowance dated Sep. 2, 2015, in U.S. Appl. No. 14/357,344.
U.S. Appl. No. 14/653,048, filed Jun. 17, 2015.
U.S. Appl. No. 14/770,200, filed Aug. 27, 2015.
U.S. Appl. No. 14/770,206, filed Aug. 27, 2015.
U.S. Appl. No. 14/357,344, filed May 9, 2014.
U.S. Appl. No. 14/357,400, filed May 9, 2014.
U.S. Appl. No. 13/697,060, filed Nov. 9, 2012.
U.S. Appl. No. 14/956,767, filed Dec. 2, 2015.
U.S. Appl. No. 14/956,836, filed Dec. 2, 2015.
U.S. Appl. No. 14/906,957, filed Jan. 22, 2016.
U.S. Appl. No. 14/906,991, filed Jan. 22, 2016.
International Search Report for International Application No. PCT/EP2014/065966, mailed Aug. 19, 2014.
International Search Report for International Application No. PCT/EP2014/065965, mailed Sep. 18, 2014.
Requirement for Restriction/Election dated Feb. 11, 2016, for U.S. Appl. No. 14/770,200.
Requirement for Restriction/Election dated Mar. 21, 2016, for U.S. Appl. No. 14/956,767.

(56) References Cited

OTHER PUBLICATIONS

Requirement for Restriction/Election dated Sep. 22, 2016 for U.S. Appl. No. 14/906,957.
Notice of Allowance dated Aug. 3, 2016, in U.S. Appl. No. 14/653,046.
Notice of Allowance dated Sep. 26, 2016, in U.S. Appl. No. 14/770,206.
Non-Final Office Action dated Mar. 8, 2016, for U.S. Appl. No. 14/956,636.
Non-Final Office Action dated Mar. 21, 2016, for U.S. Appl. No. 14/653,048.
Non-Final Office Action dated May 5, 2016, for U.S. Appl. No. 14/770,206.
Non-Final Office Action dated Jun. 10, 2016, for U.S. Appl. No. 14/770,200.
Non-Final Office Action dated Jul. 8, 2016, for U.S. Appl. No. 14/956,767.
Non-Final Office Action dated Aug. 11, 2016, for U.S. Appl. No. 14/906,991.
Berge, S. et al., Pharmaceut. Sc., 1977, vol. 66(1), pp. 1-19.

CYCLOHEXYLAMINE DERIVATIVES HAVING β2 ADRENERGIC ANTAGONIST AND M3 MUSCARINIC ANTAGONIST ACTIVITIES

This application is a continuation of U.S. patent application Ser. No. 13/697,060, filed Nov. 9, 2012, which is a national stage filing under 35 U.S.C. §371 of International Application No. PCT/EP2011/002376, filed on May 13, 2011, which claims priority to European Patent Application No. 10382118.7, filed May 13, 2010, and U.S. Provisional Application No. 61/365,045, filed Jul. 16, 2010. The contents of each respective application is incorporated herein by reference.

FIELD OF THE INVENTION

The present invention relates to novel compounds having β2 adrenergic agonist and M3 muscarinic antagonist dual activity. This invention also relates to pharmaceutical compositions containing them, process for their preparation and their use in respiratory therapies.

BACKGROUND OF THE INVENTION

Bronchodilator agents play an outstanding role in the treatment of respiratory disorders such as COPD and asthma. Beta-adrenergic agonists and cholinergic muscarinic antagonists are well established bronchodilator agents in widespread clinical use. Beta-adrenergic agonists currently used by the inhaled route include short-acting agents such as salbutamol (qid) or terbutaline (tid) and long-acting agents such as salmeterol and formoterol (bid). These agents produce bronchodilation through stimulation of adrenergic receptors on airway smooth muscle, reversing the bronchoconstrictor responses to a variety of mediators, such as acetylcholine. Inhaled muscarinic antagonists currently used include the short-acting ipratropium bromide or oxitropium bromide (qid) and the long-acting tiotropium (qd). These agents produce bronchodilation by reducing vagal cholinergic tone of airway smooth muscle. In addition to improve lung function, these agents also improve quality of life and reduce exacerbations. There are in the clinical literature a number of studies strongly demonstrating that the administration of a combination of a beta-2 agonist and a M3 antagonist is more efficacious for the treatment of COPD than either of the components alone (for example, van Noord. J. A., et al., Eur. Respir. J., 26, 214-222). Pharmaceutical compositions containing a combination of both types of bronchodilator agents are also known in the art for use in respiratory therapy. As an example, WO2009013244 discloses a medical composition containing salmeterol as beta-adrenergic agonist agent and tiotropium as antimuscarinic agent.

A single molecule possessing dual activity at muscarinic M3 and adrenergic β2 receptors (MABA) would be desirable both in terms of efficacy and side-effects in the treatment of COPD. It would show also a relevant advantage in terms of formulation compared with the two-component combination. It would be also easier to co-formulate with other therapeutic agents such as inhaled anti-inflammatories to create triple therapy combinations. Thus there is a need for new compounds having both beta2 receptor agonist and muscarinic receptor antagonist activity and being suitable for the treatment of respiratory diseases, such as asthma and COPD.

SUMMARY OF THE INVENTION

The invention provides novel compounds that possess both β2 adrenergic receptor agonist and muscarinic receptor antagonist activities. Accordingly, there is provided a compound of formula (I), or pharmaceutically acceptable salts or N-oxides or solvates or deuterated derivatives thereof:

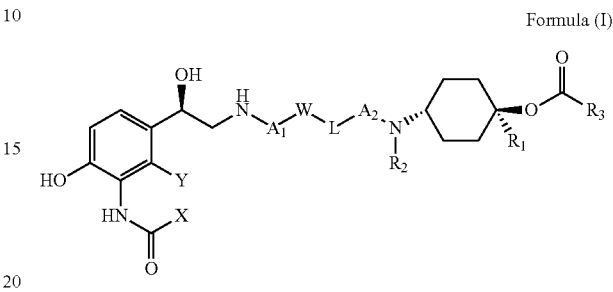

Formula (I)

Wherein:
Both X and Y represents a hydrogen atom or,
X together with Y form the group —CH=CH—, —CH$_2$—O— or —S—, wherein in the case of —CH$_2$—O— the methylene group is bound to the carbon atom in the amido substituent holding X and the oxygen atom is bound to the carbon atom in the phenyl ring holding Y,
R$_1$ and R$_2$ independently represent a hydrogen atom or a C$_{1-4}$ alkyl group,
R$_3$ represents a group of formula:

i)

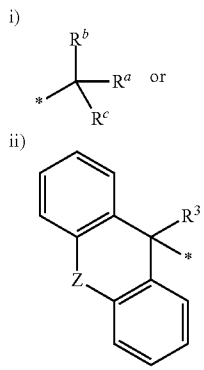

ii)

wherein:
R$^a$ represents a hydrogen atom, a hydroxy group, a hydroxymethyl group or a C$_{1-4}$ alkyl group,
R$^b$ and R$^c$ independently represents a thienyl group, a phenyl group, a benzyl group or a C$_{4-6}$ cycloalkyl group,
Z represents a direct bond or an oxygen atom, and
* represents the point of attachment of R$_3$ to the remainder of the molecule of formula (I),
A$_1$ and A$_2$ independently represent a C$_{1-6}$ alkylene group optionally substituted with one or more C$_{1-4}$ alkyl groups.
L represents a direct bond, —O—, —NH(CO)—, —(CO)NH— or —NH(CO)O—, wherein, in the case of —NH(CO)O—, the nitrogen atom is bound to the W substituent and the oxygen atom is bound to the A2 substituent; and W represents a direct bond or a phenylene group which is optionally substituted with one or more substituents selected from a halogen atom, a $C_{1-4}$ alkyl group, a $C_{1-4}$ alkoxy group and a cyano group.

The invention also provides a pharmaceutical composition comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a disease or condition associated with dual β2 adrenergic receptor and muscarinic receptor activities (e.g. a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis) in a mammal, comprising administering to the mammal, a therapeutically effective amount of a compound of the invention. The invention further provides a method of treatment comprising administering a therapeutically effective amount of a combination of a compound of the invention together with one or more other therapeutic agents.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with dual β2 adrenergic receptor and muscarinic receptor activities (e.g. a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis) in a mammal.

DETAILED DESCRIPTION OF THE INVENTION

When describing the compounds, compositions and methods of the invention, the following terms have the following meanings, unless otherwise indicated.

As used herein the term $C_{1-4}$ alkyl embraces linear or branched radicals having 1 to 4 carbon atoms. Examples include methyl, ethyl, n-propyl, i-propyl, n-butyl, sec-butyl or t-butyl.

As used herein, the term $C_{1-6}$ alkylene embraces divalent alkyl moieties typically having from 1 to 6 carbon atoms, preferably from 1 to 4 carbon atoms. Examples of $C_{1-6}$ alkylene radicals include methylene, ethylene, propylene, butylene, pentylene and hexylene radicals. A said optionally substituted alkylene group is typically unsubstituted or substituted with 1, 2 or 3 substituents which may be the same or different.

As used herein, the term $C_{1-4}$ alkoxy (or alkyloxy) embraces optionally substituted, linear or branched oxy-containing radicals each having alkyl portions of 1 to 4 carbon atoms. Examples of $C_{1-4}$ alkoxy radicals include methoxy, ethoxy, n-propoxy, i-propoxy, n-butoxy, sec-butoxy and t-butoxy. An alkoxy group is typically unsubstituted or substituted with 1, 2 or 3 substituents which may be the same or different.

As used herein, the term $C_{4-6}$ cycloalkyl group embraces saturated carbocyclic radicals monocyclic or polycyclic ring having from 4 to 6 carbon atoms, preferably from 4 to 5 carbon atoms. Examples include cyclopropyl, cyclobutyl, cyclopentyl and cyclohexyl. It is preferably cyclopropyl, cyclobutyl and cyclopentyl.

As used herein, the term halogen atom embraces chlorine, fluorine, bromine or iodine atoms typically a fluorine, chlorine or bromine atom. The term halo when used as a prefix has the same meaning.

The term "therapeutically effective amount" refers to an amount sufficient to effect treatment when administered to a patient in need of treatment.

The term "treatment" as used herein refers to the treatment of a disease or medical condition in a human patient which includes:

(a) preventing the disease or medical condition from occurring, i.e., prophylactic treatment of a patient;

(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

The phrase "disease or condition associated with β2 adrenergic receptor and muscarinic activities" includes all disease states and/or conditions that are acknowledged now, or that are found in the future, to be associated with both β2 adrenergic receptor and muscarinic receptor activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

On the other hand M3 receptor activity is associated with gastrointestinal-tract disorders such as Irritable bowel syndrome (IBS) (see, for ex., U.S. Pat. No. 5,397,800), GI ulcers, spastic colitis (see, for ex., U.S. Pat. No. 4,556,653); urinary-tract disorders such as urinary incontinence (see, for ex., J. Med. Chem., 2005, 48, 6597-6606), pollakiuria; motion sickness and vagally induced sinus bradycardia.

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphosulfonic, citric, ethanesulfonic, formic, fumaric, gluconic, glutamic, hydrobromic, hydrochloric, hydrofluoric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), napadisilic (1,5-naphthalenedisulfonic acid), triphenyl acetic and the like. Particularly preferred are salts derived from formic, fumaric, hydrobromic, hydrochloric, hydrofluoric, acetic, sulfuric, methanesulfonic, xinafoic, tartaric, maleic, succinic napadisilic acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The term "solvate" refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

As used herein, the term solvate means a compound which further includes a stoichiometric or non-stoichiometric amount of solvent such as water, acetone, ethanol, methanol, dichloromethane, 2-propanol, or the like, bound by non-covalent intermolecular forces. When the solvent is water, the term hydrate is used instead of solvate.

As used herein, the term deuterated derivative embraces compounds of the invention where in a particular position at least one hydrogen atom is replaced by deuterium. Deuterium (D or $^2$H) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of the invention has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of de oration on the compound of at least 3500 (52.5% deuterium incorporation).

In a preferred embodiment, the isotopic enrichment factor is at least 5000 (75% deuterium). In a more preferred embodiment, the isotopic enrichment factor is at least 6333.3 (95% deuterium incorporation). In a most preferred embodiment, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known too en ordinary skilled in the art, including mass spectrometry (MS) and nuclear magnetic resonance (NMR).

The term "amino-protecting group" refers to a protecting group suitable for preventing undesired reactions at amino nitrogen. Representative amino-protecting groups include, but are not limited to, formyl; acyl groups, for example alkanoyl groups such as acetyl; alkoxycarbonyl groups such as tert-butoxycarbonyl (Boc); arylmethoxycarbonyl groups such as benzyloxycarbonyl (Cbz) and 9-fluorenylmethoxycarbonyl (Fmoc); arylmethyl groups such as benzyl (Bn), trityl (Tr), and 1,1-di-(4'-methoxyphenyl)methyl; silyl groups such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The compounds of the invention contain at least one chiral centre. If more than one chiral centre is present, the invention includes individual diastereoisomers and mixtures of diastereoisomers in which each diastereoisomer may be present in equal amounts, or which may be enriched in one or more diastereoisomer.

Typically, X together with Y form the group —CH═CH— or —CH$_2$—O—. Preferably, X together with Y forms the group —CH═CH—.

Typically $R_1$ and $R_2$ independently represent a hydrogen atom or a methyl group; preferably $R_1$ represents hydrogen and $R_2$ represents a methyl group, $R_1$ and $R_2$ are both methyl groups, or both $R_1$ and $R_2$ are hydrogen atoms.

In a particularly preferred embodiment, $R_1$ represents a hydrogen atom and $R_2$ represents a methyl group.

Typically, $R_3$ represents a group of formula ii), wherein Z is an oxygen atom and $R^a$ is selected from a hydrogen atom, a hydroxy group and a methyl group.

Typically, $R_3$ represents a group of formula i) wherein:
$R^a$ represents a hydrogen atom, a hydroxy group or a methyl group, preferably $R^a$ represents a hydroxy group,
$R^b$ and $R^c$ independently represents a thienyl group, a cyclopentyl group or a phenyl group; preferably a thienyl group or a phenyl group; and more preferably both $R^b$ and $R^c$ are thienyl groups.

Typically, $A_1$ and $A_2$ independently represent a $C_{1-6}$ alkylene group optionally substituted with one or two methyl groups.

Typically, L is selected from —O—, —NH(CO)— and —NH(CO)O— groups, wherein, in the case of —NH(CO)O—, the nitrogen atom is bound to the W substituent and the oxygen atom is bound to the A2 substituent. Preferably L is selected from —O— and —NH(CO)— groups.

For the avoidance of doubt, the right hand side of the moieties depicted as possible L groups is attached to $A_2$, and the left hand side of the depicted moieties is attached to W.

Typically, W represents a phenylene group which is optionally substituted with one or two substituents selected from a chlorine atom, a methyl group, a methoxy group and a cyano group, preferably the phenylene group is substituted with two substituents selected from a chlorine atom, a methyl group, a methoxy group and a cyano group. In one embodiment of the present invention, X together with Y form —CH═CH— or —CH$_2$—O— group, $R_1$ represents a hydrogen atom or a methyl group, $R_2$ represents a hydrogen atom or a methyl group, $R_3$ represents a group of formula (i), wherein $R^a$ represents a hydroxy group and $R^b$ and $R^c$ are independently selected from a phenyl group, a cyclopentyl group and a thienyl group, or $R_3$ represents a group of formula (ii), wherein $R^a$ represents a methyl group and Z represents an oxygen atom, $A_1$ and $A_2$ independently represent a $C_{1-6}$ alkylene group optionally substituted with one or two methyl groups, L is selected from a direct bond, —O—, —NH(CO)— and —NH(CO)O— groups and W represents a direct bond or a phenylene group which is optionally substituted with one or two substituents selected from a chlorine atom, a fluorine atom, a methoxy group and a cyano group. Preferably, X together with Y form —CH═CH— group, $R_1$ represents a hydrogen atom, $R_2$ represents a hydrogen atom or a methyl group, $R_3$ represents a group of formula (I), wherein $R^a$ represents a hydroxy group and both $R^b$ and $R^c$ are thienyl group, $A_1$ and $A_2$ independently represent a $C_{1-6}$ alkylene group optionally substituted with one or two methyl groups, L is selected from a direct bond, —O—, —NH(CO)— and —NH(CO)O— groups and W represents a direct bond or a phenylene group which is optionally substituted with one or two substituents selected from a chlorine atom, a methoxy and cyano group. More Preferably, $R_2$ represents a hydrogen atom, L is selected from —O—, —NH(CO)— and —NH(CO)O— groups and W represents a phenylene group which is substituted with two substituents selected from chlorine atoms, methyl, methoxy or cyano groups.

In a preferred embodiment, X together with Y form —CH═CH— group, $R_1$ represents a hydrogen atom, $R_2$ represents a methyl group, $R_3$ represents a group of formula (i), wherein $R^a$ represents a hydroxy group and both $R^b$ and $R^c$ are thienyl group, $A_1$ and $A_2$ independently represent a $C_{1-6}$ alkylene group optionally substituted with one or two methyl groups, L is selected from —O—, —NH(CO)— and —NH(CO)O— groups and W represents a phenylene group which is substituted with two substituents selected from chlorine atoms, methyl, methoxy or cyano groups.

Particular individual compounds of the invention include:

Formic acid—trans-4-[(9-{[(2R)-2-hydroxy-2-(8-hydroxy-2-oxo-1,2-dihydroquinolin-5-yl)ethyl]amino}nonyl)(methyl)amino]cyclohexyl hydroxy(di-2-thienyl)acetate (2:1);

Formic acid—trans-4-[{2-[4-(2-{[(2R)-2-hydroxy-2-(8-hydroxy-2-oxo-1,2-dihydroquinolin-5-yl)ethyl]amino}ethyl)phenoxy]ethyl}(methyl)amino]cyclohexyl hydroxy(di-2-thienyl)acetate (1:1);

Formic acid—trans-4-[{3-[4-(2-{[(2R)-2-hydroxy-2-(8-hydroxy-2-oxo-1,2-dihydroquinolin-5-yl)ethyl]amino}ethyl)phenoxy]propyl}(methyl)amino]cyclohexyl hydroxy(di-2-thienyl)acetate (1:1);

trans-4-[{2-[(6-{[(2R)-2-Hydroxy-2-(8-hydroxy-2-oxo-1,2-dihydroquinolin-5-yl)ethyl]amino}hexyl)oxy]ethyl}(methyl)amino]cyclohexyl hydroxy(di-2-thienyl)acetate hydrofluoride;

trans-4-[{3-[(6-{[(2R)-2-Hydroxy-2-(8-hydroxy-2-oxo-1,2-dihydroquinolin-5-yl)ethyl]amino}hexyl)oxy]propyl}(methyl)amino]cyclohexyl hydroxy(di-2-thienyl)-acetate hydrofluoride;

Formic acid—trans-4-[{3-[4-({[(2R)-2-hydroxy-2-(8-hydroxy-2-oxo-1,2-dihydroquinolin-5-yl)ethyl]amino}methyl)phenoxy]propyl}(methyl)amino]cyclohexyl hydroxy(di-2-thienyl)acetate (1:1);

trans-4-[{2-[4-({[(2R)-2-Hydroxy-2-(8-hydroxy-2-oxo-1,2-dihydroquinolin-5-yl)ethyl-amino}methyl)phenoxy]ethyl}(methyl)amino]cyclohexylhydroxy(di-2-thienyl)-acetate hydrofluoride;

trans-4-[{3-[4-(2-{[(2R)-2-Hydroxy-2-(8-hydroxy-2-oxo-1,2-dihydroquinolin-5-yl)ethyl]amino}propyl)phenoxy]propyl}(methyl)amino]cyclohexylhydroxy(di-2-thienyl)acetate hydrofluoride, trans-4-((3-(2-Chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexylhydroxy(di-2-thienyl)acetate hydrofluoride;

trans-4-((3-(2-Chloro-4-(((2R)-2-hydroxy-2-(8-hydroxy-2-oxo-1,2-dihydroquinolin-5-yl)ethylamino)methyl)phenylamino)-3-oxopropyl)(methyl)amino)cyclohexylhydroxy-(di-2-thienyl)acetate hydrofluoride;

trans-4-[{3-[2-Chloro-4-({[(2R)-2-hydroxy-2-(8-hydroxy-2-oxo-1,2-dihydroquinolin-5-yl)ethyl]amino}methyl)-5-methoxyphenoxy]propyl}(methyl)amino]cyclohexyl hydroxy-(di-2-thienyl)acetate hydrofluoride;

trans-4-[{2-[({[2-Chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}-(methyl)amino]cyclohexylhydroxy(di-2-thienyl)acetate hydrofluoride, trans-4-[(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)(methyl)amino]-1-methylcyclohexyl hydroxy(di-2-thienyl)acetate, trans-4-[(3-{[4-({[(2R)-2-hydroxy-2-(8-hydroxy-2-oxo-1,2-dihydroquinolin-5-yl)ethyl]amino}methyl)phenyl]amino}-3-oxopropyl)(methyl)amino]cyclohexyl hydroxy (di-2-thienyl)acetate hydrofluoride (1:2), trans-4-[(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)(methyl)amino]-cyclohexyl hydroxy(di-2-thienyl)acetate, trans-4-[(3-{[2-fluoro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)(methyl)amino]-cyclohexyl hydroxy(di-2-thienyl)acetate, trans-4-[(3-{[4-({[(2R)-2-hydroxy-2-(8-hydroxy-2-oxo-1,2-dihydroquinolin-5-yl)ethyl]amino}methyl)-3-methoxyphenyl]amino}-3-oxopropyl)(methyl)amino]-cyclohexyl hydroxy(di-2-thienyl)acetate hydrofluoride (1:2), trans-4-[(3-{[2,5-difluoro-4-({[(2R)-2-hydroxy-2-(8-hydroxy-2-oxo-1,2-dihydroquinolin-5-yl)ethyl]amino}methyl)phenyl]amino}-3-oxopropyl)(methyl)amino]-cyclohexyl hydroxy(di-2-thienyl)acetate hydrofluoride (1:2), trans-4-[(3-{[2-fluoro-4-({[(2R)-2-hydroxy-2-(8-hydroxy-2-oxo-1,2-dihydroquinolin-5-yl)ethyl]amino}methyl)phenyl]amino}-3-oxopropyl)(methyl)amino]cyclohexyl hydroxy(di-2-thienyl)acetate hydrofluoride (1:2), trans-4-[(3-{[2-chloro-4-(2-{[(2R)-2-hydroxy-2-(8-hydroxy-2-oxo-1,2-dihydroquinolin-5-yl)ethyl]amino}ethyl)-5-methoxyphenyl]amino}-3-oxopropyl)-(methyl)amino]cyclohexyl hydroxy(di-2-thienyl)acetate hydrofluoride (1:2), trans-4-[{3-[2-chloro-4-(2-{[(2R)-2-hydroxy-2-(8-hydroxy-2-oxo-1,2-dihydroquinolin-5-yl)ethyl]amino}ethyl)-5-methoxyphenoxy]propyl}(methyl)-amino]cyclohexyl hydroxy(di-2-thienyl)acetate hydrofluoride (1:2), trans-4-[{2-[({[2-cyano-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)amino]cyclohexyl hydroxy(di-2-thienyl)acetate hydrofluoride (1:2), trans-4-[{2-[({[2,5-difluoro-4-({[(2R)-2-hydroxy-2-(8-hydroxy-2-oxo-1,2-dihydroquinolin-5-yl)ethyl]amino}methyl)phenyl]amino}carbonyl)oxy]ethyl}-(methyl)amino]cyclohexyl hydroxy(di-2-thienyl)acetate hydrofluoride (1:2), trans-4-[(3-{[2-chloro-4-({[(2R)-2-hydroxy-2-(8-hydroxy-2-oxo-1,2-dihydroquinolin-5-yl)ethyl]amino}methyl)-5- methoxyphenyl]amino}-2,2-dimethyl-3-oxopropyl)-(methyl)amino]cyclohexyl hydroxy(di-2-thienyl)acetate, trans-4-[{4-[2-chloro-4-({[(2R)-2-hydroxy-2-(8-hydroxy-2-oxo-1,2-dihydroquinolin-5-yl)ethyl]amino}methyl)-5-methoxyphenoxy]butyl}(methyl)amino]cyclohexyl hydroxy(di-2-thienyl)acetate hydrofluoride (1:2), trans-4-[{2-[({[2-chloro-4-({[(2R)-2-hydroxy-2-(5-hydroxy-3-oxo-3,4-dihydro-2H-1,4-benzoxazin-8-yl)ethyl]amino}methyl)-5-methoxyphenyl]amino}carbonyl)oxy]-ethyl}(methyl)amino]cyclohexyl hydroxy(di-2-thienyl)acetate, trans-4-[(9-{[(2R)-2-hydroxy-2-(8-hydroxy-2-oxo-1,2-dihydroquinolin-5-yl)ethyl]-amino}nonyl)(methyl)amino]cyclohexyl 9-methyl-9H-xanthene-9-carboxylate, trans-4-[{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)-amino]cyclohexyl (2R)-cyclopentyl(hydroxy)phenylacetate, and trans-4-[{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)amino]cyclohexyl (2S)-cyclopentyl(hydroxy)2-thienylacetate.

Of particular interest are the compounds:

Formic acid—trans-4-[(9-{[(2R)-2-hydroxy-2-(8-hydroxy-2-oxo-1,2-dihydroquinolin-5-yl)ethyl]amino}nonyl)(methyl)amino]cyclohexyl hydroxy(di-2-thienyl)acetate (2:1);

Formic acid—trans-4-[{3-[4-(2-{[(2R)-2-hydroxy-2-(8-hydroxy-2-oxo-1,2-dihydroquinolin-5-yl)ethyl]amino}ethyl)phenoxy]propyl}(methyl)amino]cyclohexyl hydroxy(di-2-thienyl)acetate (1:1);

trans-4-[{3-[(6-{[(2R)-2-Hydroxy-2-(8-hydroxy-2-oxo-1,2-dihydroquinolin-5-yl)ethyl]-amino}hexyl)oxy]propyl}(methyl)amino]cyclohexyl hydroxy(di-2-thienyl)acetate hydrofluoride;

Formic acid—trans-4-[{3-[4-({[(2R)-2-hydroxy-2-(8-hydroxy-2-oxo-1,2-dihydroquinolin-5-yl)ethyl]amino}methyl)phenoxy]propyl}(methyl)amino]cyclohexylhydroxy-(di-2-thienyl)acetate (1:1);

trans-4-((3-(2-Chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexylhydroxy(di-2-thienyl)acetate hydrofluoride;

trans-4-[{3-[2-Chloro-4-({[(2R)-2-hydroxy-2-(8-hydroxy-2-oxo-1,2-dihydroquinolin-5-yl)ethyl]amino}methyl)-5-methoxyphenoxy]propyl}(methyl)amino]cyclohexylhydroxy-(di-2-thienyl)acetate hydrofluoride, trans-4-[(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)(methyl)amino]-1-methylcyclohexyl hydroxy(di-2-thienyl)acetate, trans-4-[(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)(methyl)amino]-cyclohexyl hydroxy(di-2-thienyl)acetate, trans-4-[(3-{[2-fluoro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)(methyl)amino]-cyclohexyl hydroxy(di-2-thienyl)acetate, trans-4-[(3-{[2-chloro-4-(2-{[(2R)-2-hydroxy-2-(8-hydroxy-2-oxo-1,2-dihydroquinolin-5-y)ethyl]amino}ethyl)-5-methoxyphenyl]amino}-3-oxopropyl)(methyl)amino]-cyclohexyl hydroxy(di-2-thienyl)acetate hydrofluoride (1:2), trans-4-[{3-[2-chloro-4-(2-{[(2R)-2-hydroxy-2-(8-hydroxy-2-oxo-1,2-dihydroquinolin-5-yl)ethyl]amino}ethyl)-5-methoxyphenoxy]propyl}(methyl)amino]cyclohexyl hydroxy(di-2-thienyl)acetate hydrofluoride (1:2);

trans-4-[{2-[({[2-cyano-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)-amino]cyclohexyl hydroxy(di-2-thienyl)acetate hydrofluoride (1:2), trans-4-[{4-[2-chloro-4-({[(2R)-2-hydroxy-2-(8-hydroxy-2-oxo-1,2-dihydroquinolin-5-yl)ethyl]amino}methyl)-5-methoxyphenoxy]butyl}(methyl)amino]cyclohexyl hydroxy(di-2-thienyl)acetate hydrofluoride (1:2), and trans-4-[{2-[({[2-chloro-4-({[(2R)-2-hydroxy-2-(5-hydroxy-3-oxo-3,4-dihydro-2H-1,4-benzoxazin-8-yl)ethyl]amino}methyl)-5-methoxyphenyl]amino}carbonyl)oxy]ethyl}-(methyl)amino]cyclohexyl hydroxy(di-2-thienyl)acetate, and trans-4-[{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)-amino]cyclohexyl (2R)-cyclopentyl(hydroxy)phenylacetate.

In an embodiment of the present invention the pharmaceutical composition further comprises a therapeutically effective amount of one or more other therapeutic agents, in particular one or more drugs selected from the group consisting of corticosteroids, and PDE4 inhibitors It is also an embodiment of the present invention that the pharmaceutical composition is formulated for administration by inhalation.

The compounds of the present invention as hereinabove defined may also be combined with one or more other therapeutic agents, in particular one or more drugs selected from the group consisting of corticosteroids and PDE4 inhibitors.

The invention is also directed to compounds of formula (I) for use in the treatment of a pathological condition or disease associated with both β2 adrenergic receptor and muscarinic receptor activities such as a pulmonary disease. In particular the pulmonary disease is asthma or chronic obstructive pulmonary disease.

The pathological condition or disease can also be applied within the scope of the present invention to the treatment of a disease or condition selected from the group consisting of pre-term labor, glaucoma, neurological disorders, cardiac disorders, and inflammation, urological disorders such as urinary incontinence and gastrointestinal disorders such as irritable bowel syndrome or spastic colitis The invention is also directed to the use of compounds of formula (I) for the manufacture of a medicament for the treatment of pathological condition or disease associated with one or both β2 adrenergic receptor and muscarinic receptor activities such as a pulmonary disease, in particular asthma or chronic obstructive pulmonary disease, pre-term labor, glaucoma, neurological disorders, cardiac disorders, inflammation, urological disorders and gastrointestinal disorders.

The invention is also directed to a method of treating these diseases, which comprises administering a therapeutically effective amount of a pharmaceutical composition comprising a dual β2 adrenergic receptor agonists and muscarinic receptor antagonists according to the present invention. The method further comprises administering a therapeutically effective amount of one or more other therapeutic agent selected from the group consisting of a corticosteroid and a PDE4 inhibitor.

The invention is also directed to a method of modulating the activity of a β2 adrenergic and/or a M3 receptor, the method comprising stimulating a β2 adrenergic receptor and/or blocking a M3 receptor with a modulatory amount of compounds of formula (I).

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below.

One of the most convenient route for the preparation of compounds of formula (I) is depicted in Scheme 1.

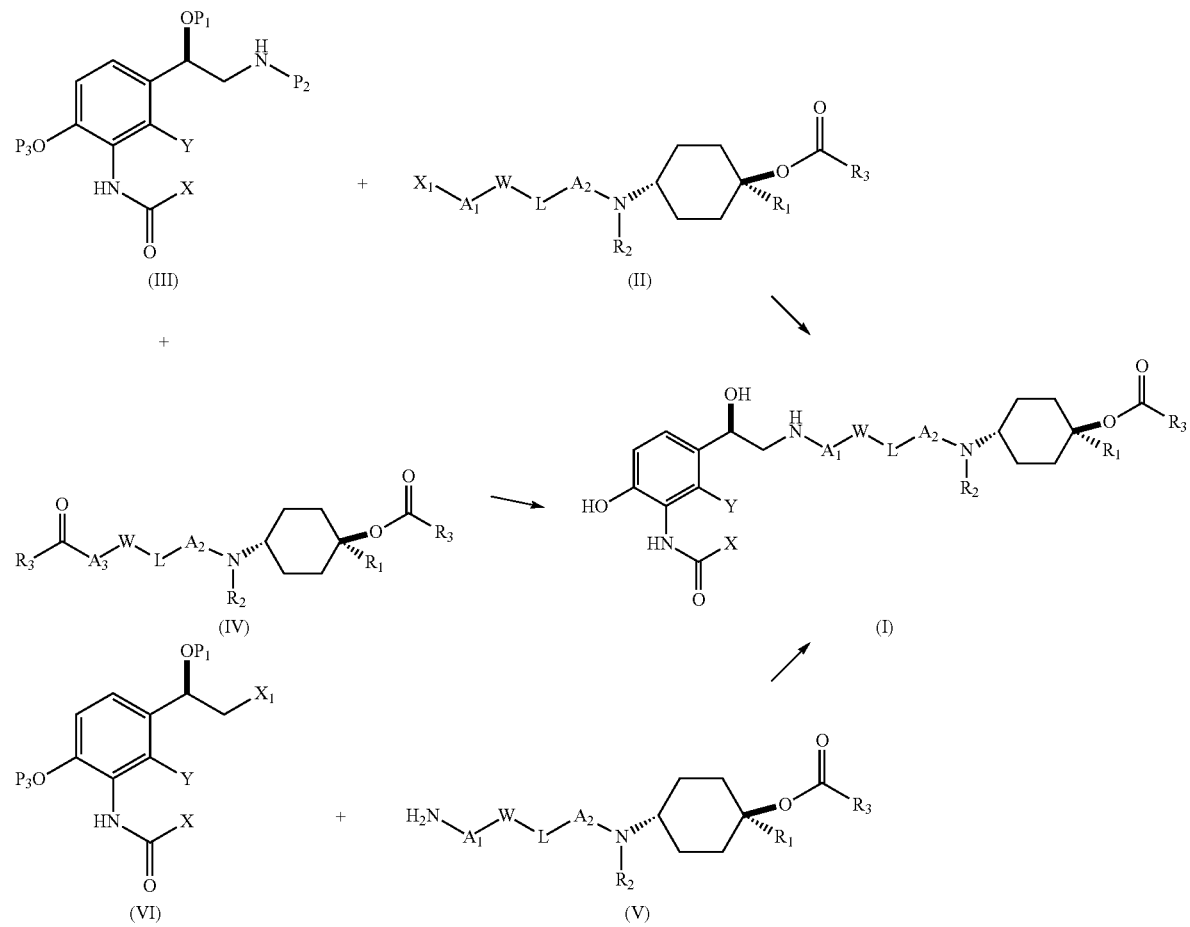

Compounds of formula (I) may be prepared by reacting Intermediates of formula (II), wherein $X_1$ represents a leaving group such as a halogen atom or an active ester as mesylate or tosylate, with intermediates of formula (III), wherein $P_1$ and $P_3$ independently represent a hydrogen atom or a oxygen-protecting group such as a silyl or benzyl ether and $P_2$ represents a hydrogen atom or a nitrogen-protecting group such as for example a benzyl group. This reaction is best carried out in an aprotic polar solvent such as DMF, 1-methyl-2-pyrrolidone or DMSO in a range of temperatures between room temperature and 200° C., in the presence of an acid scavenger such as sodium hydrogen carbonate or a tertiary amine.

Alternatively, compounds of formula (I) may be prepared by reacting intermediates of formula (V) with intermediates of formula (VI) wherein $X_1$, $P_1$ and $P_3$ have the same meaning as disclosed above, following the same synthetic procedure disclosed above; and subsequently removing whichever protecting group present in the intermediate to provide a compound of formula (I). Such deprotection processes involve, for example, a desilylation process, by using triethylamine trihydrofluoride, TBAF, hydrogen chloride or other acidic reagents in an inert solvent like THF in a range of temperatures between 0° C. and 50° C. The deprotection could also be carried out by a debenzylation process, for example, by hydrogenating the compound in the presence of a catalyst such as palladium on charcoal in an inert solvent like ethanol or THF or a mixture of solvents. This reaction is typically carried out at a hydrogen pressure between 10 and 60 psi and in a range of temperatures between room temperature and 50° C.

In another alternative way, compounds of formula (I) may also be prepared by reacting intermediates of formula (IV) wherein $A_0$ represents a group that together with the adjacent methylene newly formed affords the $A_1$ group, being $R_0$ a hydrogen or $C_{1-4}$ alkyl group, with intermediates of formula (III). This reaction is best carried out in a solvent or mixture of solvents like THF, methanol, dichloromethane or DMSO at a temperature between 0° C. and 60° C. using a hydride like sodium borohydride or sodium triacetoxyborohydride as reducing agent.

Intermediates of formula (II) may be prepared from commercially available starting materials and reagents using well known procedures, as depicted in Scheme 2.

Intermediates of formula (II) may be prepared from alcohol derivatives of formula (VII) via acylation with sulphonyl halides in the presence of an acid scavenger or by halogenation with a variety of halogenating agents.

Intermediates of formula (VII) may be prepared by direct alkylation of an amine of formula (VIII) with the corresponding alkylating fragment (IXa) wherein $X_3$ represents a leaving group such as a halogen atom or an active ester as mesylate or tosylate, in the presence of an acid scavenger such as a tertiary amine.

Alternatively, Intermediates of formula (II) may be directly obtained from intermediates of formula (VIII) and intermediates (IXb), wherein $X_1$ and $X_3$ are as previously disclosed.

The amino-ester derivatives of formula (VIII) may be prepared by deprotecting compounds of formula (X), wherein $P_4$ represents a protecting group, for example, by removing tert-butoxycarbonyl group (BOC) in the presence of acidic media such as hydrogen chloride in THF.

Intermediates of formula (X) are best prepared by a transesterification process starting from literature-known aminoalcohol derivatives of formula (XII) and methyl esters derivative of formula (XI), typically in the presence of a base as sodium hydride and and by displacing the equilibrium by distillation of a solvent like toluene.

Intermediates of formula (III) are widely described in the literature (see, for example, US2004242622 example 6; WO2008149110 intermediate 65; US2007249674 example 3B), and may be prepared following the same synthetic procedure described therein.

Scheme 2

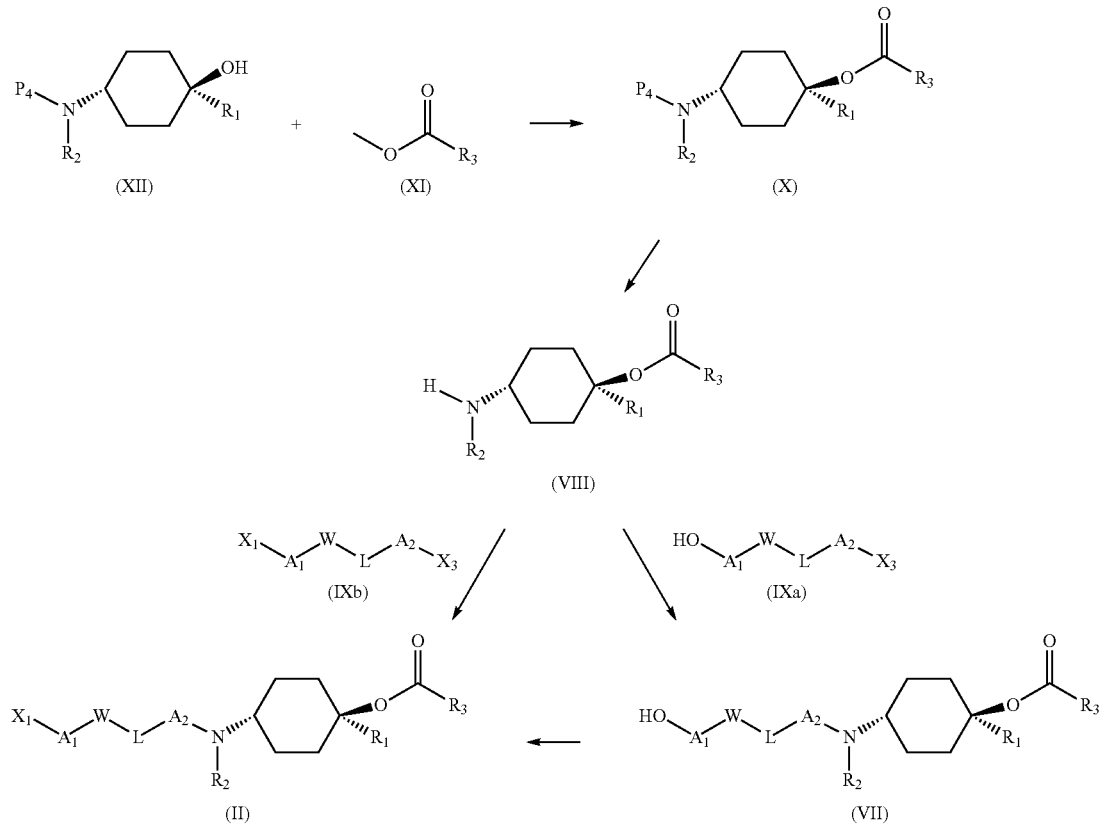

Intermediates of formula (IV) may be prepared either by oxidation of intermediates of formula (XIII) with an oxidizing agent such as manganese dioxide or Dess-Martin reagent or by direct alkylation of an intermediate of formula (VIII) with an alkylating agent of formula (XIV) in the presence of an acid scavenger. Compounds (IV) are also available by homolagation of aldehydes (XVIII) through reaction with methoxymethyltriphenylphosphine in the presence of a base such as lithium bis(trimethylsilyl)amidure and subsequent acidic hydrolysis of the intermediate enolic ether or by oxidation of the vinyl derivatives (XX), prepared in turn by alkylation of (VIII) with intermediates (XIX). This oxidation can be accomplished with a variety of agents, such as osmium tetroxyde in the presence of N-methylmorpholine N-oxyde.

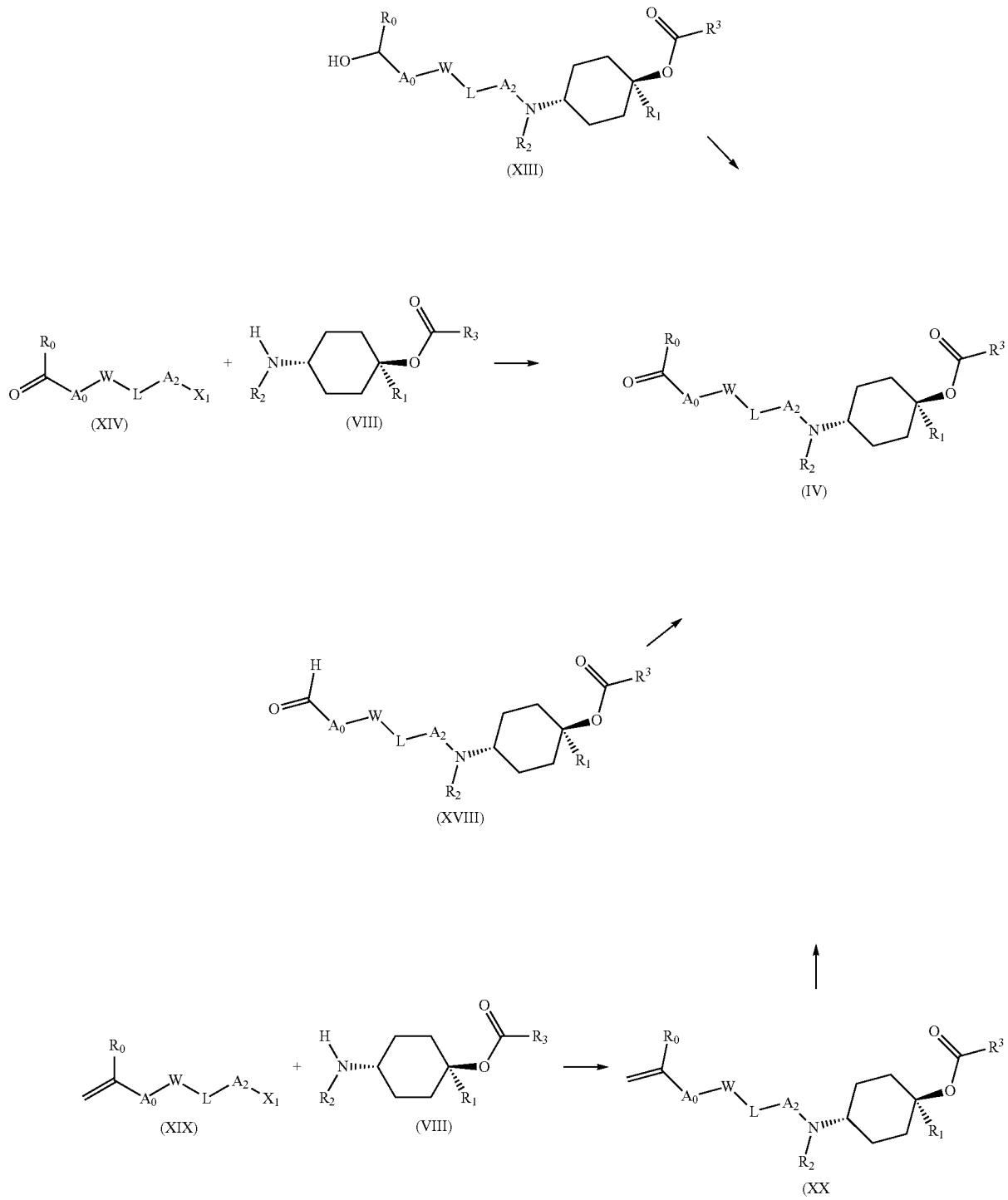

Intermediates of formula (V) may be prepared from their N-protected homologues (XV) by a specific deprotecting process such as the treatment of N-BOC derivative with acidic media like hydrogen chloride in THF.

Scheme 4

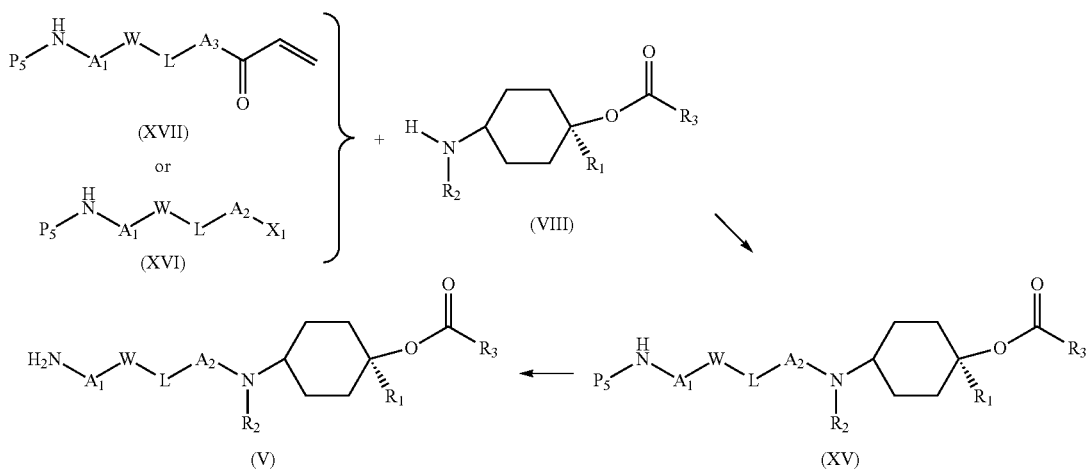

Intermediates of formula (XV) are in turn prepared from intermediates of formula (VIII) by procedures well known in the art, such as alkylation procedures with intermediates of formula (XVI) in the presence of an acid scavenger such as a tertiary amine or with intermediates of formula (XVII), wherein $A_3$ plus the additional 3 adjacent carbon atoms give raise to A.

EXAMPLES

General. Reagents, starling materials, and solvents were purchased from commercial suppliers and used as received. Concentration refers to evaporation under vacuum using a Büchi rotatory evaporator. Reaction products were purified, when necessary, by flash chromatography on silica gel (40-63 µm) with the solvent system indicated or using preparative HPLC conditions (see bellow description of two systems used). Spectroscopic data were recorded on a Varian Gemini 300 spectrometer. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector.

HPLC System 1:
C-18 reversed phase column silica from MERCK, water/acetonitrile as eluents [0.1% v/v ammonium formate buffered] using a gradient from 0% to 100%.

HPLC System 2:
C-18 reversed phase column silica from MERCK, water/acetonitrile (without buffer) as eluents using a gradient from 0% to 100%.

Intermediate 1 tert-butyl(trans-4-hydroxycyclohexyl)carbamate

To a solution of (1R,4R)-4-aminocyclohexanol (15 g, 0.13 mol) in acetonitrile (240 mL) was added in portions di-tert-butyl dicarbonate (31.2 g, 0.14 mol). The mixture was stirred overnight at room temperature. The precipitate obtained was washed with hexane/ethyl acetate (3:1) and hexane giving the title compound as a white solid (83%).

$^1$H NMR (300 MHz, CHLOROFORM-d) □ ppm 1.17 (br. s., 2 H) 1.44 (br. s., 9 H) 1.32-1.40 (m, 2 H) 1.99 (br. s., 4 H) 3.44 (br. s., 1 H) 3.61 (br. s., 1 H) 4.38 (br. s., 1 H)

Intermediate 2 trans-4-(Methylamino)cyclohexanol

To a mixture of lithium aluminium hydride (9 g, 0.23 mol) in tetrahydrofuran (425 mL) was added slowly tert-butyl (trans-4-hydroxycyclohexyl)carbamate (intermediate 1, 10 g, 0.046 mol). The mixture was refluxed overnight. Once the mixture was cooled to room temperature, 9 ml of water, 9 ml of 4N NaOH solution and 18 ml of water were carefully and successively dropped. The organic solvent was removed under reduced pressure and the crude obtained was dissolved with chloroform and dried over magnesium sulphate. The filtrate was evaporated to dryness and co evaporated with hexane to give the title compound as a white solid (89%). This intermediate is also described in JMC, 1987, 30(2), p313.

$^1$H NMR (300 MHz, CHLOROFORM-a) □ ppm 1.04-1.20 (m, 2 H) 1.25-1.40 (m, 2 H) 1.97 (br. s., 4 H) 2.27-2.40 (m, 1 H) 3.57-3.70 (m, 1 H)

Intermediate 3 tert-butyl(trans-4-hydroxycyclohexyl)methylcarbamate

To a solution of trans-4-(methylamino)cyclohexanol (intermediate 2, 5.3 g, 0.04 mol) in acetonitrile (92 mL) was added in portions di-tert-butyl dicarbonate (9.9 g, 0.04 mol). The mixture was stirred overnight at room temperature. The solvent was removed under reduced pressure and the crude was purified by column chromatography with silica gel, eluting with a mixture of chloroform/methanol (from 75:1 to 4:1)) to give the title compound as a colourless oil (87%).

¹H NMR (300 MHz, CHLOROFORM-d) ☐☐☐☐ ppm 1.34-1.43 (m, 2 H) 1.46 (s, 9 H) 1.49-1.57 (m, 2 H) 1.70 (d, J=9.89 Hz, 2 H) 2.03 (br. s., 3 H) 2.71 (br. s., 3 H) 3.57 (br. s., 1 H)

Intermediate 4 trans-4-[(tert-butoxycarbonyl)(methyl)amino]cyclohexyl hydroxy(di-2-thienyl)-acetate To a solution of methyl hydroxy(di-2-thienyl)acetate (5.8 g, 0.02 mol) (prepared according to *Acta Chemica Scandinavica* 24 (1970) 1590-1596) in anhydrous toluene (95 mL) was first added a solution of tert-butyl(trans-4-hydroxycyclohexyl)-methylcarbamate (intermediate 3; 6 g, 0.02 mol) in anhydrous toluene (95 mL) and secondly sodium hydride (60%, 0.45 g, 0.01 mol). After few minutes the mixture was warmed to 155° C. and the solvent was distilled and simultaneously replaced. This procedure was carried on during 1 hour and a half. The mixture was cooled to room temperature and diluted with ether (300 mL). The organic layer was washed with sodium bicarbonate 4% (2×200 mL) and brine, dried, filtered and evaporated over reduced pressure giving the title compound as a yellow solid (69%), which was used in the next step without further purification.

LRMS (m/z): 452 (M+1)⁺.

Intermediate 5 trans-4-(methylamino)cyclohexyl hydroxy(di-2-thienyl)acetate

To a solution of trans-4-[(tert-butoxycarbonyl)(methyl)amino]cyclohexyl hydroxy(di-2-thienyl)acetate (intermediate 4; 8.1 g, 0.01 mol) in dioxane (13.5 mL) was added hydrogen chloride 4M in dioxane (27 mL). The mixture was stirred at room temperature for 24 hours. The precipitate obtained was filtrated and washed with ether. The crude was dissolved in water and potassium carbonate was added until pH=8-9. The product was extracted with ethyl acetate and the organic layer was washed with brine, dried and evaporated to dryness giving the title compound as a white solid (78%).

LRMS (m/z): 352 (M+1)⁺.
¹H NMR (300 MHz, CHLOROFORM-d) ☐ ppm 1.14-1.30 (m, 2 H) 1.42-1.57 (m, 2 H) 1.88-2.11 (m, 4 H) 2.36-2.48 (m, 1 H) 3.71 (s, 3 H) 4.82-4.95 (m, 1 H) 6.94-7.00 (m, 2 H) 7.14-7.19 (m, 2 H) 7.25-7.30 (m, 2 H)

Intermediate 6 trans-4-[(9-bromononyl)(methyl)amino]cyclohexyl hydroxy(di-2-thienyl)acetate

Trans-4-(methylamino)cyclohexyl hydroxy(di-2-thienyl)acetate (intermediate 5, 0.5 g, 0.001 mol), 1,9-dibromononane (2.9 mL, 0.01 mol) and triethylamine (0.44 mL, 0.003 mol) were mixed together under nitrogen atmosphere and stirred at 70° C. for 94 hours. The reaction mixture was evaporated and purified by column chromatography with silica gel, eluting with chloroform/methanol (from 100 to 4:1) to give the title compound as a brown oil (55%).

LRMS (m/z): 556, 558 (1Br) (M, M+2)⁺.

Intermediate 7 trans-4-[(9-{[(2R)-2-{[tert-butyl(dimethyl)silyl]oxy}-2-(8-hydroxy-2-oxo-1,2-dihydroquinolin-5-yl)ethyl]amino}nonyl)(methyl)amino]cyclohexylhydroxy(di-2-thienyl)acetate A mixture of trans-4-[(9-bromononyl)(methyl)amino]cyclohexyl hydroxy(di-2-thienyl)-acetate (intermediate 6; 0.44 g, 0.79 mmol), 5-((1R)-2-amino-1-{[tert-butyl(dimethyl)silyl]oxy}ethyl)-8-hydroxyquinolin-2(1H)-one (prepared according to preparation 8 from US20060035931) (0.26 g, 0.79 mmol) and sodium bicarbonate (0.08 g, 0.95 mmol) in dimethylacetamide (9 mL) was stirred overnight at 60° C. The organic solvent was removed under reduced pressure and the crude was partitioned between ethyl acetate and water. The organic layer was washed with water and brine, dried, filtrated and evaporated giving a crude which was purified by column chromatography with silica gel, eluting with chloroform/methanol (from 15:1 to 4:1) to give the title compound as a yellow oil (25%).

LRMS (m/z): 811 (M+1)⁺.

Example 1 trans-4-[(9-{[(2R)-2-hydroxy-2-(8-hydroxy-2-oxo-1,2-dihydroquinolin-5-yl)ethyl]-amino}nonyl)(methyl)amino]cyclohexyl hydroxy(di-2-thienyl)acetate formiate (2:1)

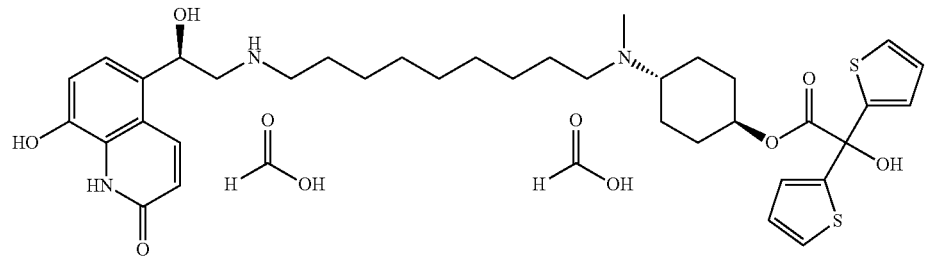

To a solution of trans-4-[(9-{[(2R)-2-{[tert-butyl(dimethyl)silyl]oxy}-2-(8-hydroxy-2-oxo-1,2-dihydroquinolin-5-yl)ethyl]amino}nonyl)(methyl)amino]cyclohexyl hydroxy(di-2-thienyl)acetate (intermediate 7; 0.8 g, 0.13 mmol) in tetrahydrofuran (5.1 mL) was added triethylamine trihydrofluoride (0.14 mL, 0.89 mmol) under nitrogen atmosphere. The reaction mixture was stirred at room temperature for 20 hours. The crude reaction was diluted with methylene chloride and the organic layer washed with sodium bicarbonate and brine, dried, filtered and evaporated. The crude product was purified by preparative reversed-phase HPLC (System 1) obtaining the title compound as a colourless solid (61%).

LRMS (m/z): 696 (M+1)$^+$.

$^1$H NMR (400 MHz, DMSO-d$_6$)☐☐ ppm 1.24 (s, 10 H) 1.36 (br. s., 6 H) 1.53 (br. s., 4 H) 1.71 (br. s., 2 H) 1.92 (br. s., 2 H) 2.14 (s, 3 H) 2.31-2.46 (m, 4 H) 2.69-2.80 (m, 2 H) 2.81-2.94 (m, 2 H) 5.23 (dd, J=8.79, 3.71 Hz, 1 H) 6.51 (d, J=10.16 Hz, 1 H) 6.95-7.00 (m, 3 H) 7.07 (dd, J=3.71, 1.37 Hz, 2 H) 7.09 (d, J=8.21 Hz, 1 H) 7.46 (dd, J=5.08, 1.17 Hz, 2 H) 8.19 (d, J=9.77 Hz, 1 H) 8.39 (br. s., 2 H, x2HCOOH)

Intermediate 8

2-[4-(2-bromoethoxy)phenyl]ethanol

To a solution of 4-(2-hydroxyethyl)phenol (5 g, 0.035 mol) in acetone (50 mL) was added 1,2-dibromoethane (15.6 mL, 1.3 mol) and potassium carbonate (13 g, 0.09 mol). The mixture was stirred at 80° C. for 48 hours. The salts were filtered and the mixture was evaporated. The crude obtained was partitioned between ethyl acetate/water. The organic layer was washed with sodium hydroxide 2N, water and brine, dried, filtered and the solvent was removed under reduced pressure to give the title compound as a white solid (73%), which was used in the next step without further purification.

LRMS (m/z): 246 (M+1)$^+$.

Intermediate 9 trans-4-[{2-[4-(2-hydroxyethyl)phenoxy]ethyl}(methyl)amino]cyclohexylhydroxyl-(di-2-thienyl)acetate Obtained as a colourless oil (57%) from trans-4-(methylamino)cyclohexyl hydroxy(di-2-thienyl)acetate (intermediate 5; 0.35 g, 0.001 mol), 2-[4-(2-bromoethoxy)phenyl]ethanol (intermediate 8; 0.36 g, 0.0015 mol) and triethylamine (0.27 mL, 0.002 mol) following the experimental procedure as described for intermediate 6 followed by column chromatography with silica gel, eluting with chloroform/methanol (from 75:1 to 25:1)

LRMS (m/z): 516 (M÷1)$^+$.

Intermediate 10 trans-4-{methyl[2-(4-{2-[(methylsulfonyl)oxy]ethyl}phenoxy)ethyl]amino}-cyclohexylhydroxy(di-2-thienyl)acetate To a mixture of trans-4-[{2-[4-(2-hydroxyethyl)phenoxy]ethyl}(methyl)amino]cyclohexyl hydroxy(di-2-thienyl)acetate (intermediate 9; 0.22 g, 0.44 mmol) in chloroform (3 mL) and triethylamine (0.09 mL, 0.66 mmol) was added methanesulfonyl chloride (0.03 mL, 0.5 mmol) at 0° C. during 15 minutes, then the mixture was stirred at room temperature for 24 hours. The mixture was diluted with chloroform and washed with sodium bicarbonate 4%, water and brine, dried and filtered. The solvent was removed under reduced pressure giving crude which was purified by column chromatography with silica gel, eluting with chloroform/methanol 50:1. The title compound was obtained as yellow oil (70%).

LRMS (m/z): 594(M+1)$^+$.

Intermediate 11 trans-4-[{2-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]ethyl}(methyl)amino]cyclohexyl hydroxy(di-2-thienyl)acetate Obtained as a brown oil (33%) from trans-4-(methyl[2-(4-{2-[(methylsulfonyl)oxy]ethyl}-phenoxy)ethyl]amino}cyclohexyl hydroxy(di-2-thienyl)acetate (intermediate 10; 0.16 g, 0.27 mmol), 5-((1R)-2-amino-{[tert-butyl(dimethyl)silyl]oxy}ethyl)-8-hydroxyquinolin-2(1H)-one (prepared according to preparation 8 from US20060035931) (0.09 g, 0.27 mmol) and sodium bicarbonate (0.03 g, 0.33 mmol) following the experimental procedure as described for intermediate 7 and the crude obtained was used in the next step without further purification.

LRMS (m/z): 833(M+1)$^+$.

Example 2 trans-4-[{2-[4-(2-{[(2R)-2-hydroxy-2-(8-hydroxy-2-oxo-1,2-dihydroquinolin-5-yl)ethyl]amino}ethyl)phenoxy]ethyl}(methyl)amino]cyclohexylhydroxy(di-2-thienyl)acetate formiate (1:1)

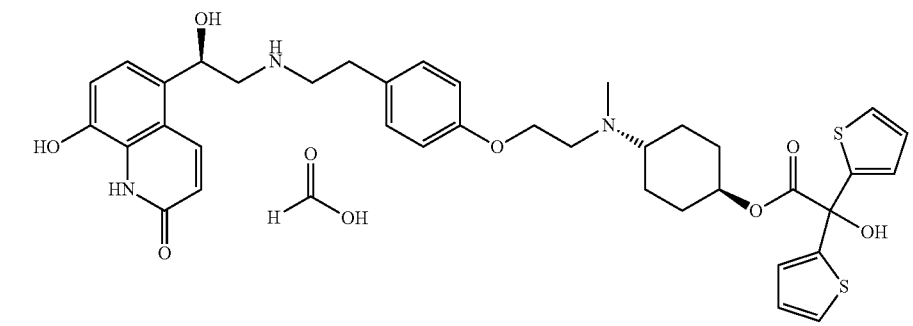

Obtained as white solid (25%) from trans-4-[{2-[4-(2-{[(2R)-2-{[tert-butyl(dimethyl)silyl]-oxy}-2-(8-hydroxy-2-oxo-1,2-dihydroquinolin-5-yl)ethyl]amino}ethyl)phenoxy]ethyl}-(methyl)amino]cyclohexyl hydroxy(di-2-thienyl)acetate (intermediate 11, 0.25 g, 0.09 mmol) and triethylamine trihydrofluoride (0.25 mL, 1.53 mmol) following the experimental procedure as described in Example 1, followed by a purification by preparative reversed-phase HPLC (System 1).

LRMS (m/z): 717(M+1)$^+$.

Intermediate 12 trans-4-[{3-[4-(2-hydroxyethyl)phenoxy]propyl}(methyl)amino]cyclohexyl-hydroxy(di-2-thienyl)acetate Obtained as a colourless oil (41%) from 2-(4-(3-bromopropoxy)phenyl)ethanol (prepared according to intermediate 26 from WO2008096127) (1.1 g, 0.004 mol), trans-4-(methylamino)cyclohexyl hydroxy(di-2-thienyl)acetate (intermediate 5; 1 g, 0.003 mol) and triethylamine (0.78 mL, 0.005 mol) following the experimental procedure as described for intermediate 6, followed by a purification by column chromatography with silica gel, eluting with chloroform/methanol 15:1.

LRMS (m/z): 530(M+1)$^+$.

Intermediate 13 trans-4-{methyl[3-(4-{2-[(methylsulfonyl)oxy]ethyl}phenoxy)propyl]amino}-cyclohexylhydroxy(di-2-thienyl)acetate Obtained as a colourless oil (83%) from trans-4-[{3-[4-(2-hydroxyethyl)phenoxy]propyl}-(methyl)amino]cyclohexyl hydroxy(di-2-thienyl)acetate (intermediate 12; 0.63 g, 0.001 mol), triethylamine (0.14 mL, 0.001 mol) and methanesulfonyl chloride (0.1 mL, 0.001 mol) following the experimental procedure as described in intermediate 10 (reaction time: 3 hours), followed by a purification by column chromatography with silica gel, eluting with chloroform/methanol (from 50:1 to 15:1).

LRMS (m/z): 608 (M+1)$^+$.

Intermediate 14 trans-4-[{3-[4-(2-{[(2R)-2-hydroxy-2-(8-hydroxy-2-oxo-1,2-dihydroquinolin-5-yl)ethyl]amino}ethyl)phenoxy]propyl}(methyl)amino]cyclohexylhydroxy(di-2-thienyl)acetate Obtained as a brown oil (25%) from trans-4-{methyl[3-(4-{2-[(methylsulfonyl)oxy]ethyl}-phenoxy)propyl]amino}cyclohexyl hydroxy(di-2-thienyl)acetate (intermediate 13; 0.6 g, 0.9 mmol), 5-((1R)-2-amino-1-{[tert-butyl(dimethyl)silyl]oxy}ethyl)-8-hydroxyquinolin-2(1H)-one (prepared according to preparation 8 from US20060035931) (0.3 g, 0.9 mmol) and sodium bicarbonate (0.1 g, 1.2 mmol) following the experimental procedure as described for intermediate 7 (reaction time: 32 hours). The crude obtained was used in the next step without further purification.

LRMS (m/z): 847 (M+1)$^+$.

Example 3 trans-4-[{3-[4-(2-{[(2R)-2-hydroxy-2-(8-hydroxy-2-oxo-1,2-dihydroquinolin-5-yl)ethyl]amino}ethyl)phenoxy]propyl}(methyl)amino]-cyclohexylhydroxy(di-2-thienyl)acetate formiate (1:1)

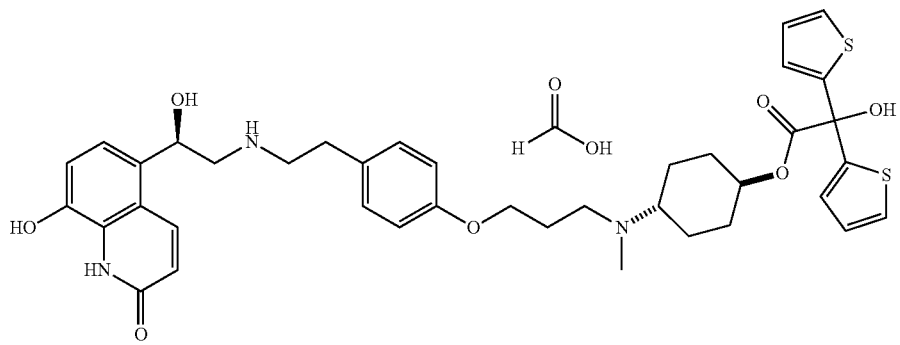

Obtained as a white solid (27%) from trans-4-[{3-[4-(2-{[(2R)-2-hydroxy-2-(8-hydroxy-2-oxo-1,2-dihydroquinolin-5-yl)ethyl]amino}ethyl)phenoxy]propyl}(methyl)amino]-cyclohexyl hydroxy(di-2-thienyl)acetate (intermediate 14; 0.87 g, 0.25 mmol) and triethylamine trihydrofluoride (0.84 mL, 5.19 mmol) following the experimental procedure as described in Example 1, followed by a purification by preparative reversed-phase HPLC (System 1) and a lyophilization.

LRMS (m/z): 742(M+1)$^+$.

$^1$H NMR (300 MHz, DMSO-d$_6$) ☐ ppm 1.29 (br. s., 4 H) 1.64 (br. s., 2 H) 1.72 (br. s., 2 H) 1.85 (br. s., 2 H) 2.09 (s, 3 H) 2.11 (br. s., 2 H) 2.33 (br. s., 1 H) 2.63 (br. s., 2 H) 2.73 (br. s., 3 H) 3.86 (br. s., 2 H) 4.62 (br. s., 2 H) 5.02 (br. s., 1 H) 6.44 (d, J=9.89 Hz, 1 H) 6.76 (br. s., 3 H) 6.83-6.95 (m, 3 H) 6.95-7.07 (m, 4 H) 7.40 (br. s., 2 H) 8.09 (d, J=9.89 Hz, 1 H) 8.26 (s, 1 H, HCOOH)

Intermediate 15

13,13,14,14-Tetramethyl-1-phenyl-2,5,12-trioxa-13-silapentadecane

To a mixture of 2-(benxyloxy)ethanol (1.8 mL, 0.01 mol), (6-bromohexyloxy)(tert-butyl)dimethylsilane (7.18 mL, 0.02 mol) and tetrabutylammonium bromide (0.23 g, 0.71 mmol) was added dropwise sodium hydroxide (32% p/v, 9.6 mL, 0.07 mol). The mixture was stirred vigorously overnight at 70° C. Water (200 mL) was added into the mixture and the crude was extracted with hexane (2×100 mL), the combined organic layers were washed with water and brine, dried, filtered and evaporated to dryness. The crude oil obtained was purified by column chromatography with silica gel, eluting with hexane/ethyl acetate (from 50:1 to 5:1) to give the title compound as colourless oil (85%).

LRMS (m/z): 367(M+1)$^+$.

Intermediate 16

2-[(6-{[tert-Butyl(dimethyl)silyl]oxy}hexyl)oxy]ethanol

To a solution of 13,13,14,14-tetramethyl-1-phenyl-2,5,12-trioxa-13-silapentadecane (intermediate 15; 3.1 g, 0.008 mol) in methanol (74 mL) was added palladium on charcoal (10%, 0.3 g). The mixture was stirred overnight at room temperature under hydrogen (balloon pressure). The catalyst was filtered and the filtrate was evaporated under reduced pressure giving crude, which was purified by column chromatography with silica gel, eluting with hexane/ethyl acetate (from 9:1 to 4:1) to give the title compound as a colourless oil (77%).

$^1$H NMR (300 MHz, CHLOROFORM-d) □□ ppm 0.02 (s, 3H) 0.85 (s, 9 H) 1.31 (ddd, J=7.35, 3.98, 3.78 Hz, 4 H) 1.42-1.57 (m, 2 H) 1.97 (t, J=6.18 Hz, 2 H) 3.43 (t, J=6.59 Hz, 2 H) 3.46-3.51 (m, 2 H) 3.56 (t, J=6.45 Hz, 2 H) 3.68 (dt, J=5.84, 4.64 Hz, 2 H)

Intermediate 17

2-[(6-{[tert-Butyl(dimethyl)silyl]oxy}hexyl)oxy]ethyl methanesulfonate

Obtained as a colourless oil (92%) from 2-[(6-{[tert-butyl(dimethyl)silyl]oxy}hexyl)-oxy]ethanol (intermediate 16; 2 g, 0.007 mol), triethylamine (3.52 mL, 0.02 mol) and methanesulfonyl chloride (1.2 mL, 0.01 mol) following the experimental procedure as described in intermediate 10, followed by a purification by column chromatography with silica gel, eluting with hexane/ethyl acetate (from 5:1 to 3:1)

$^1$H NMR (300 MHz, CHLOROFORM-a) □□□□ppm 0.05 (s, 6 H) 0.89 (s, 9 H) 1.30-1.42 (m, 4 H) 1.58 (br. s., 4 H) 3.06 (s, 3 H) 3.48 (t, J=6.59 Hz, 2 H) 3.60 (t, J=6.45 Hz, 2 H) 3.69 (d, J=4.67 Hz, 2 H) 4.37 (d, J=4.39 Hz, 2 H)

Intermediate 18 trans-4-[{2-[(6-{[tert-butyl(dimethyl)silyl]oxy}hexyl)oxy]ethyl}-(methyl)amino]-cyclohexyl hydroxy(di-2-thienyl)acetate Obtained as an oil (31%) from 2-[(6-{[tert-butyl(dimethyl)silyl]oxy}hexyl)oxy]ethyl methanesulfonate (intermediate 17; 0.45 g, 1.28 mmol), trans-4-(methylamino)-cyclohexyl hydroxy(di-2-thienyl)acetate (intermediate 5, 0.3 g, 0.85 mmol) and triethylamine (0.2 mL, 1.71 mmol) following the experimental procedure as described in intermediate 6, followed by a purification by column chromatography with silica gel, eluting with chloroform/methanol (from 50/1 to 25/1).

LRMS (m/z): 610(M+1)$^+$.

Intermediate 19 trans-4-[{2-[(6-hydroxyhexyl)oxy]ethyl}(methyl)amino]-cyclohexylhydroxy(di-2-thienyl)acetate To a solution of trans-4-[{2-[(6-{[tert-butyl(dimethyl)silyl]oxy}hexyl)oxy]ethyl}(methyl)-amino]cyclohexyl hydroxy(di-2-thienyl)acetate (intermediate 18; 0.1 g, 0.28 mmol) in tetrahydrofuran (2.4 mL) was added hydrochloric acid (1M, 1.13 mL) The mixture was stirred at room temperature for 1 hour. The mixture was neutralized by a saturated solution of sodium bicarbonate and the crude was extracted with ethyl acetate, dried, filtered and evaporated to dryness. The title compound was obtained as a colourless oil (85%).

LRMS (m/z): 496(M+1)$^+$.

Intermediate 20 trans-4-{methyl[2-({6-[(methylsulfonyl)oxy]hexyl}oxy)ethyl]amino}cyclohexyl hydroxy(di-2-thienyl)acetate Obtained as an oil (88%) from trans-4-[{2-[(6-hydroxyhexyl)oxy]ethyl}(methyl)-amino]cyclohexyl hydroxy(di-2-thienyl)acetate (intermediate 19; 0.1 g, 0.31 mmol), triethylamine (0.09 mL, 0.64 mmol)) and methanesulfonyl chloride (0.042 mL, 0.54 mmol) following the experimental procedure as described in intermediate 10, followed by a purification by column chromatography with silica gel, eluting with chloroform/methanol (from 50:1 to 25:1).

LRMS (m/z): 574(M+1)$^+$.

Intermediate 21 trans-4-[[(12R)-12-(8-hydroxy-2-oxo-1,2-dihydroquinolin-5-yl)-14,14,15,15-tetramethyl-3,13-dioxa-10-aza-14-silahexadec-1-yl](methyl)amino]cyclohexyl hydroxy(di-2-thienyl)acetate Obtained as an brown oil (16%) from trans-4-{methyl[2-({6-[(methylsulfonyl)oxy]hexyl}-oxy)ethyl]amino}cyclohexylhydroxy(di-2-thienyl)acetate (intermediate 20; 0.16 g, 0.28 mmol), 5-((1R)-2-amino-1-{[tert-butyl(dimethyl)silyl]oxy}ethyl)-8-hydroxyquinolin-2(1H)-one (prepared according to preparation 8 from US20060035931) (0.09 g, 0.28 mmol) and sodium bicarbonate (0.029 g, 0.35 mmol) following the experimental procedure as described in intermediate 7, the crude obtained was used in the next step without further purification.

LRMS (m/z): 811(M+1)$^+$.

Example 4 trans-4-[{2-[(6-{[(2R)-2-hydroxy-2-(8-hydroxy-2-oxo-1,2-dihydroquinolin-5-yl)-ethyl]amino}hexyl)oxy]ethyl}(methyl)amino]cyclohexylhydroxy(di-2-thienyl)-acetate hydrofluoride

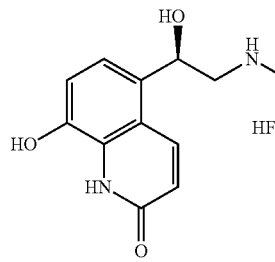 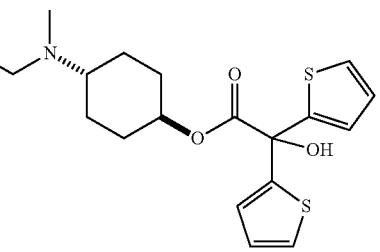

Obtained as a white solid (39%) from trans-4-[[(12R)-12-(8-hydroxy-2-oxo-1,2-dihydroquinolin-5-yl)-14,14,15,15-tetramethyl-3,13-dioxa-10-aza-14-silahexadec-1-yl](methyl)amino]cyclohexyl hydroxy(di-2-thienyl)acetate (intermediate 20, 0.24 g, 0.05 mmol) and triethylamine trihydrofluoride (0.25 mL, 1.53 mmol) following the experimental procedure as described in Example 1, followed by a purification by preparative reversed-phase HPLC (System 2) and a lyophilization.

LRMS (m/z): 699(M+1)+.

Intermediate 22

14,14,15,15-Tetramethyl-1-phenyl-2,6,13-trioxa-14-silahexadecane

Obtained as a colourless oil (67%) from 3-(benzyloxy)propan-1-ol (2 mL, 0.01 mol), (6-bromohexyloxy)(tert-butyl)dimethylsilane (7.1 mL, 0.02 mol), tetrabutylammonium bromide (0.24 g, 0.0007 mol) and sodium hydroxide (32% p/v, 9.5 mL) following the experimental procedure as described in intermediate 15, followed by a purification by column chromatography with silica gel, eluting with hexane/ethyl acetate 10:1.

LRMS (m/z): 381(M+1)$^{30}$.

Intermediate 23

3-[(6-{[tert-butyl(dimethyl)silyl]oxy}hexyl)oxy]propan-1-ol

Obtained as colourless oil (95%) from 14,14,15,15-tetramethyl-1-phenyl-2,6,13-trioxa-14-silahexadecane (intermediate 22; 3.3 g, 0.008 mol) and palladium on charcoal (10%, 0.3 g) following the experimental procedure as described in intermediate 16, followed by a purification by column chromatography with silica gel, eluting with hexane/ethyl acetate 7/1.

$^1$H NMR (300 MHz, CHLOROFORM-d) □ ppm 0.01 (s, 6 H) 0.85 (s, 9 H) 1.26-1.35 (m, 4 H) 1.42-1.59 (m, 4 H) 1.80 (d, J=5.49 Hz, 2 H) 3.38 (t, J=6.59 Hz, 2 H) 3.52-3.61 (m, 4 H) 3.69-3.78 (m, 2 H)

Intermediate 24

3-[(6-{[tert-butyl(dimethyl)silyl]oxy}hexyl)oxy]propylmethanesulfonate

Obtained as an oil (94%) from 3-[(6-{[tert-butyl(dimethyl)silyl]oxy}hexyl)oxy]propan-1-ol (intermediate 23; 1 g, 0.003 mol), triethylamine (1.7 mL, 0.01 mmol) and methanesulfonyl chloride (0.29 mL, 0.003 mol) following the experimental procedure as described in intermediate 10, followed by a purification by column chromatography with silica gel, eluting with hexane/ethyl acetate (from 100% to 50%).

$^1$H NMR (300 MHz, CHLOROFORM-d)□□□□ ppm 0.01 (s, 6 H) 0.85 (br. s., 9 H) 1.31 (br. s., 4 H) 1.43-1.59 (m, 4 H) 1.97 (br. s., 2 H) 2.98 (s, 3 H) 3.38 (br. s., 3 H) 3,48 (br. s., 2 H) 3.57 (br. s., 2 H) 4.31 (br. s., 2 H).

Intermediate 25 trans-4-{[3-[(6-{[tert-butyl(dimethyl)silyl]oxy}hexyl)oxy]propyl}(methyl)amino]-cyclohexyl-hydroxy(di-2-thienyl)acetate Obtained as brown oil (52%) from 3-[(6-{[tert-butyl(dimethyl)silyl]oxy}hexyl)oxy]propyl methanesulfonate (intermediate 24; 0.74 g, 0.001 mol), trans-4-(methylamino)-cyclohexyl hydroxy(di-2-thienyl)acetate (intermediate 5, 0.76 g, 0.002 mol) and triethylamine (0.6 mL, 0.004 mol) following the experimental procedure as described in intermediate 6, followed by a purification by column chromatography with silica gel, eluting with chloroform/methanol 20/1.

LRMS (m/z): 624(M+1)+.

Intermediate 26 trans-4-[{3-[(6-hydroxyhexyl)oxy]propyl}(methyl)amino]cyclohexylhydroxy(di-2-thienyl)acetate Obtained as a brown solid (98%) from trans-4-[{3-[(6-{[tert-butyl(dimethyl)silyl]oxy}-hexyl)oxy]propyl}(methyl)amino]cyclohexyl hydroxy(di-2-thienyl)acetate (intermediate 25; 0.7 g, 0.001 mol) and hydrochloric acid (1M, 4.3 mL) following the experimental procedure as described in intermediate 19, the crude obtained was used in the next step without further purification.

LRMS (m/z): 510(M+1)+.

Intermediate 27 trans-4-{methyl[3-({6-[(methylsulfonyl)oxy]hexyl}oxy)propyl]amino}cyclohexyl hydroxy(di-2-thienyl)acetate Obtained as an oil (78%) from trans-4-[{3-[(6-hydroxyhexyl)oxy]propyl}(methyl)-amino]cyclohexyl hydroxy(di-2-thienyl)acetate (intermediate 26; 0.57 g, 0.001 mol), triethylamine (0.22 mL, 0.0012 mmol) and methanesulfonyl chloride (0.1 mL, 0.001 mol) following the experimental procedure as described in intermediate 10, followed by a purification by column chromatography with silica gel, eluting with chloroform/methanol 20/1.

LRMS (m/z): 588(M+1)+.

Intermediate 28 trans-4-[[(13R)-13-(8-hydroxy-2-oxo-1,2-dihydro-quinolin-5-yl)-15,15,16,16-tetramethyl-4,14-dioxa-11-aza-15-silaheptadec-1-yl](methyl)amino]cyclohexyl hydroxy(di-2-thienyl)acetate Obtained as brown oil (10%) from trans-4-{methyl[3-({6-[(methylsulfonyl)oxy]hexyl}oxy)-propyl]amino}cyclohexyl hydroxy(di-2-thienyl)acetate (intermediate 27; 0.5 g, 0.83 mmol), 5-((1R)-2-amino-1-{[tert-butyl(dimethyl)silyl]oxy}ethyl)-8-hydroxyquinolin-2(1H)-one (prepared according to preparation 8 from US20060035931) (0.27 g, 0.83 mmol) and sodium bicarbonate (0.09 g, 1.15 mmol) following the experimental procedure as described in intermediate 7, the crude obtained was used in the next step without further manipulation.

LRMS (m/z): 827(M+1)+.

Example 5 trans-4-[{3-[(6-{[(2R)-2-hydroxy-2-(8-hydroxy-2-oxo-1,2-dihydroquinolin-5-yl)-ethyl]amino}hexyl)oxy]propyl}(methyl)amino]cyclohexyl hydroxy(di-2-thienyl)-acetate hydrofluoride Intermediate 29 trans-4-[[3-(4-formylphenoxy)propyl](methyl)amino]cyclohexyl hydroxy(di-2-thienyl)acetate Obtained as a yellow oil (66%) from 4-(3-bromopropoxy)benzaidehyde (prepared according to example 53 from WO2008096127) (0.25 g, 0.001 mol), trans-4-(methylamino)cyclohexyl hydroxy(di-2-thienyl)acetate (intermediate 5; 0.25 g, 0.0007 mol) and triethylamine (0.19 mL, 0.001 mol) following the experimental procedure as described in intermediate 6, followed by a purification by column chromatography with silica gel, eluting with chloroform/methanol 50/1.

LRMS (m/z): 514(M+1)+.

Intermediate 30 trans-4-[{3-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]propyl}(methyl)amino]-cyclohexylhydroxy(di-2-thienyl)acetate To a solution of trans-4-[[3-(4-formylphenoxy)propyl](methyl)amino]cyclohexyl hydroxy(di-2-thienyl)acetate (in-

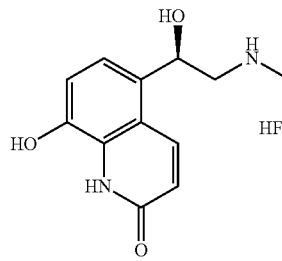
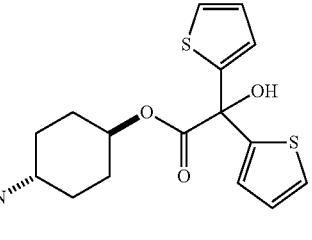

Obtained as a solid (16%) from trans-4-[[(13R)-13-(8-hydroxy-2-oxo-1,2-dihydroquinolin-5-yl)-15,15,16,16-tetramethyl-4,14-dioxa-11-aza-15-silaheptadec-1-yl](methyl)amino]cyclohexyl hydroxy(di-2-thienyl)acetate (intermediate 28; 0.35 g, 0.09 mmol) and triethylamine trihydrofluoride (0.46 mL, 2.82 mmol) following the experimental procedure as described in Example 1, followed by a purification by preparative reversed-phase HPLC (System 2).

LRMS (m/z): 712(M+1)+.

1H NMR (300 MHz, DMSO-d6) □□□ppm 1.27 (br. s., 4 H) 1.36 (br. s., 2 H) 1.41-1.61 (m, 4 H) 1.69 (br. s., 4 H) 1.91 (br. s., 4 H) 2.12 (s, 3 H) 2.38 (br. s., 2 H) 2.64 (br. s., 3 H) 2.78 (br. s., 2 H) 3.21-3.30 (m, 4 H) 4.69 (br. s., 1 H) 5.10 (br. s., 1 H) 6.52 (d, J=9.89 Hz, 1 H) 6.92 (d, J=8.24 Hz, 1 H) 6.97 (dd, J=5.08, 3.71 Hz, 2 H) 7.07 (dd, J=3.57, 1.37 Hz, 2 H) 7.07-7.10 (m, 1 H) 7.46 (dd, J=5.08, 1.24 Hz, 2 H) 8.17 (d, J=10.16 Hz, 1 H)

termediate 29; 25 mg, 0.05 mmol) in tetrahydrofuran (0.7 mL) was added (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (24 mg, 0.06 mmol). The mixture was stirred under nitrogen atmosphere at 60° C. for 6 hours. The reaction was cooled to 0° C. and sodium triacetoxyborohydride (32 mg, 0.15 mmol) was added. The mixture was stirred at room temperature overnight. A solution of sodium bicarbonate 4% (2 mL) was added into the reaction vessel (pH=8), and the crude was extracted with ethyl acetate. The organic layer was washed with water and brine, dried, filtered and the solvent was removed under reduced pressure giving the title compound as an oil (99%), which was used in the next step without further purification.

LRMS (m/z); 833(M+1)+.

Example 6 trans-4-[{3-[4-({[(2R)-2-hydroxy-2-(8-hydroxy-2-oxo-1,2-dihydroquinolin-5-yl)-ethyl]amino}methyl)phenoxy]propyl}(methyl)amino]-cyclohexylhydroxy(di-2-thienyl)acetate formate (1:1)

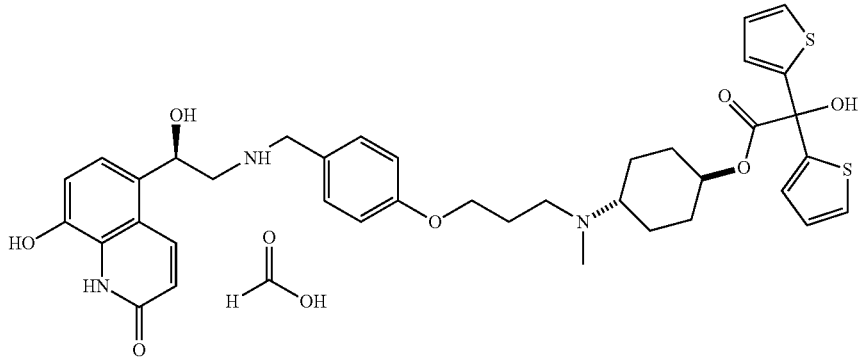

Obtained as pale yellow solid (54%) from trans-4-[{3-[4-({[(2R)-2-{[tert-butyl(dimethyl)-silyl]oxy}-2-(8-hydroxy-2-oxo-1,2-dihydroquinolin-5-yl)ethyl]amino}-methyl)phenoxy]-propyl}(methyl)amino]cyclohexylhydroxy(di-2-thienyl)acetate (intermediate 30; 0.21 g, 0.21 mmol) and triethylamine trihydrofluoride (0.12 mL, 0.77 mmol) following the experimental procedure as described in Example 1, followed by a purification by preparative reversed-phase HPLC (System 1).

LRMS (m/z): 718(M+1)$^+$.

$^1$H NMR (300 MHz, DMSO-d$_6$) □ ppm 1.37 (br. s., 4 H) 1.61-2.01 (m, 6 H) 2.17 (s, 3 H) 2.35-2.45 (m, 2 H) 2.54 (br. s., 1 H) 2.72 (br. s., 2 H) 3.77 (br. s., 2 H) 3.96 (br. s., 2 H) 4.69 (br. s., 1 H) 5.11 (br. s., 1 H) 6.48 (d, J=9.89 Hz, 1 H) 6.83-6.89 (m, 2H) 6.92 (d, J=7.97 Hz, 2 H) 6.98 (br. s., 2 H) 7.03-7.12 (m, 3 H) 7.25 (d, J=8.51 Hz, 2 H) 7.46 (d, J=6.32 Hz, 1 H) 8.09 (d, J=9.89 Hz, 1 H) 8.27 (s, 1 H, HCOOH)

Intermediate 31

4-(2-Bromoethoxy)benzaldehyde

To a solution of 4-hydroxybenzaldehyde (3 g, 0.024 mol) in ethanol (30 mL) was added potassium carbonate (6.6 g, 0.047 mol) and 1,2-dibromoethane (21 mL, 0.24 mol). The reaction mixture was stirred at 70° C. for 20 hours. The salts were filtered and the filtrate was concentrated. The crude was dissolved in ethyl acetate and the organic layer was washed with water, sodium hydroxide 2N and brine, dried, and filtered. The organic solvent was removed under reduced pressure to give the title compound as a yellow-orange solid (88%), which was used in the next step without further purification.

LRMS (m/z): 230(M+1)$^+$.

Intermediate 32 trans-4-[[2-(4-Formylphenoxy)ethyl](methyl)amino]cyclohexyl hydroxy(di-2-thienyl)acetate Obtained as a solid (60%) from 4-(2-bromoethoxy)benzaldehyde (intermediate 31; 0.5 g, 0.002 mol), trans-4-(methylamino)cyclohexyl hydroxy(di-2-thienyl)acetate (intermediate 5, 0.5 g, 0.001 mol) and triethylamine (0.39 mL, 0.002 mol) following the experimental procedure as described in intermediate 6, followed by a purification by column chromatography with silica gel, eluting with chloroform/methanol (from 50:1 to 25:1).

LRMS (m/z): 500(M+1)$^+$.

Intermediate 33 trans-4-[{2-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]ethyl}(methyl)amino]-cyclohexylhydroxy(di-2-thienyl)acetate Obtained as a yellow solid (89%) from trans-4-[[2-(4-formylphenoxy)ethyl](methyl)-amino]cyclohexyl hydroxy(di-2-thienyl)acetate (intermediate 32; 0.39 g, 0.79 mmol), (2R)-2-{[tert-butyl(dimethyl)silyl]oxy}-2-(8-hydroxy-2-oxo-1,2-dihydroquinolin-5-yl)-ethanaminium acetate (prepared according to preparation 8 from US20060035931) (0.37 g, 0.96 mmol) and sodium triacetoxyborohydride (0.5 g, 2.38 mmol) following the experimental procedure as described in intermediate 30, the crude obtained was used in the next step without further purification.

LRMS (m/z): 819(M+1)$^+$.

Example 7 trans-4-[{2-[4-({[(2R)-2-Hydroxy-2-(8-hydroxy-2-oxo-1,2-dihydroquinolin-5-yl)ethyl]amino}methyl)phenoxy]ethyl}(methyl)amino]cyclohexyl hydroxy(di-2-thienyl)acetate hydrofluoride

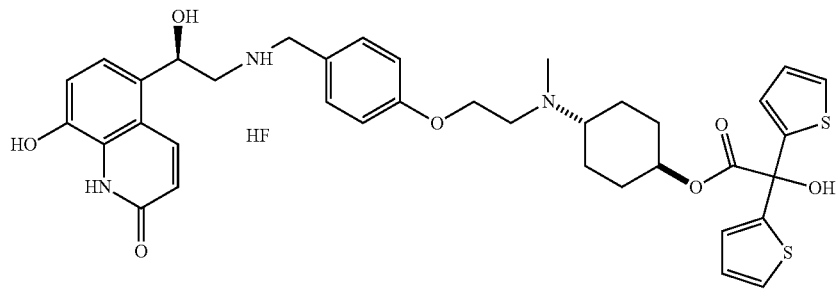

Obtained as a pale yellow solid (44%) from trans-4-[{2-[4-({[(2R)-2-{[tert-butyl-(dimethy)silyl]oxy}-2-(8-hydroxy-2-oxo-1,2-dihydroquinolin-5-yl)ethyl]amino}methyl)-phenoxy]ethyl}(methyl)amino]cyclohexyl hydroxy(di-2-thienyl)acetate (intermediate 33; 0.6 g, 0.71 mmol) and triethylamine trihydrofluoride (0.36 mL, 2.22 mmol) following the experimental procedure as described in Example 1, followed by a purification by preparative reversed-phase HPLC (System 2).

LRMS (m/z): 705(M+1)$^+$.

$^1$H NMR (300 MHz, DMSO-d$_6$) δ ppm 1.30-1.47 (m, 4 H) 1.74 (br. s., 2 H) 1.93 (br. s., 2 H) 2.25 (s, 3 H) 2.42-2.48 (m, 4 H) 2.76 (br. s., 4 H) 3.84 (s, 1 H) 3.98 (t, J=5.91 Hz, 2 H) 4.71 (br. s., 1 H) 5.17 (br. s., 1 H) 6.49 (d, J=9.89 Hz, 1 H) 6.84-6.94 (m, 3 H) 6.98 (dd, J=5.36, 3.98 Hz, 2 H) 7.07 (br. s., 4 H) 7.30 (d, J=8.24 Hz, 2 H) 7.47 (d, J=4.94 Hz, 1 H) 8.12 (d, J=9.89 Hz, 1 H)

Intermediate 34

1-[4-(3-Bromopropoxy)phenyl]acetone

To a solution of 1-(4-hydroxyphenyl)propan-2-one (2.2 g, 0.01 mol) in dimethylformamide (10 mL) was added 1,3-dibromopropane (7.6 mL, 0.07 mol), potassium carbonate (2.3 g, 0.01 mol) and potassium iodide (0.7 g, 0.004 mol). The mixture was stirred at room temperature for 72 hours. Water was added into the reaction vessel and the crude was extracted with ethyl acetate. The organic layer was washed with water and brine, dried, filtered and evaporated to dryness. The crude obtained was purified by column chromatography with silica gel, eluting with hexane/ethyl acetate (from 100% to 10%), obtaining the title compound (54%).

LRMS (m/z): 272(M+1)$^+$.

Intermediate 35 trans-4-(Methyl{3-[4-(2-oxopropyl)phenoxy]propyl}amino)cyclohexyl hydroxy(di-2-thienyl)acetate Obtained as brown-yellow oil (84%) from 1-[4-(3-bromopropoxy)phenyl]acetone (intermediate 34; 1 g, 0.003 mol), trans-4-(methylamino)cyclohexyl hydroxy(di-2-thienyl)acetate (intermediate 5, 0.6 g, 0.002 mol) and triethylamine (0.5 mL, 0.004 mol) following the experimental procedure as described in intermediate 6, followed by a purification by column chromatography with silica gel, eluting with chloroform/methanol 25:1

LRMS (m/z): 542(M+1)$^+$.

Intermediate 36 trans-4-[{3-[4-(2-{[(2R)-2-{[tert-butyl(dimethyl)silyl]oxy}-2-(8-hydroxy-2-oxo-1,2-dihydroquinolin-5-yl)ethyl]amino}propyl)phenoxy]propyl}(methyl)amino]-cyclohexylhydroxy(di-2-thienyl)acetate Obtained as a yellow foam (57%) from trans-4-(methyl{3-[4-(2-oxopropyl)phenoxy]-propyl}amino)cyclohexylhydroxy(di-2-thienyl)acetate (intermediate 35; 0.4 g, 0.72 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (0.34 g, 0.87 mmol) and sodium triacetoxyborohydride (0.4 g, 1.84 mol) following the experimental procedure as described in intermediate 30, the crude obtained was used in the next step without further purification.

LRMS (m/z): 861(M+1)$^+$.

Example 8 trans-4-[{3-[4-(2-{[(2R)-2-hydroxy-2-(8-hydroxy-2-oxo-1,2-dihydroquinolin-5-yl)-ethyl]amine}propyl)phenoxy]propyl}(methyl)amino]cyclohexylhydroxy(di-2-ienyl)acetate hydrofluoride

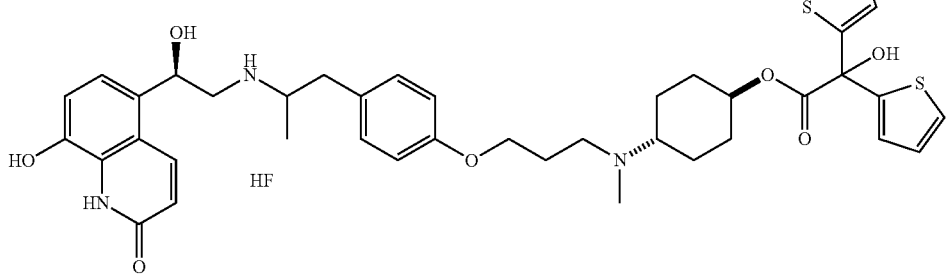

Obtained as a yellow foam (50%) from trans-4-[{3-[4-(2-{[(2R)-2-([tert-butyl(dimethyl)-silyl]oxy}-2-(8-hydroxy-2-oxo-1,2-dihydroquinolin-5-yl)ethyl]amino}-propyl)phenoxy]-propyl}(methyl)amino]cyclohexyl hydroxy(di-2-thienyl)acetate (intermediate 36; 0.37 g, 0.0002 mol) and triethylamine trihydrofluoride (1 mL, 0.01 mol) following the experimental procedure as described in Example 1, followed by a purification by preparative reversed-phase HPLC (System 2) and a lyophilization.

LRMS (m/z): 746(M+1)$^+$.

$^1$H NMR (300 MHz, DMSO-d$_6$) □ □□ppm 0.96 (br. s., 4 H) 1.36 (br. s., 3 H) 1.61-1.97 (m, 5 H) 2.18 (br. s., 5 H) 2.43 (br. s., 4 H) 2.86 (br. s., 2 H) 3.03 (br. s., 1 H) 3.93 (br. s., 2 H) 4.68 (br. s., 1 H) 5.15 (br. s., 1 H) 6.53 (d, J=9.89 Hz, 1 H) 6.81 (br. s., 2 H) 6.86-7.00 (m, 3 H) 7.06 (br. s., 4 H) 7.25 (br. s., 1 H) 7.46 (br. s., 2 H) 8.20 (br. s., 1 H)

Intermediate 37

Ethyl 4-amino-5-chloro-2-methoxybenzoate

A solution of 4-amino-5-chloro-2-methoxybenzoic acid (6.6 g, 0.031 mol) in hydrogen chloride 1.25M in Ethanol (250 mL, 0.31 mol) was stirred in a pressure vessel for 6 h at 65° C. The reaction mixture was basified with sodium hydroxide 2N and extracted with methylene chloride. The organic layer was washed with water, dried and filtered. The solvent was removed under reduced pressure giving the title compound as a white solid (78%), which was used in the next step without further purification.

LRMS (m/z): 230(M+1)$^+$.

Intermediate 38

(4-Amino-5-chloro-2-methoxyphenyl)methanol

To a solution of lithium aluminium hydride (0.96 g, 0.025 mol) in tetrahydrofuran (100 mL) was added dropwise at room temperature a solution of ethyl 4-amino-5-chloro-2-methoxybenzoate (intermediate 37; 4.4 g, 0.019 mol) in tetrahydrofuran (25 mL). Then the mixture was refluxed for 2 hours. The excess of hydride was destroyed by successive addition of 1 ml of water, 1 ml of 4N NaOH solution and 2 ml of water, filtered through celite and washed with ethyl acetate. The organic solvent was reduced and hexane was added. The mixture was cooled at 0° C. during 1 hour and then the precipitate was filtrated and washed with hexane. The title compound was obtained as a pale yellow solid (80%) which was used in the next step without further purification.

LRMS (m/z): 188(M+1)$^+$.

Intermediate 39

4-({[tert-butyl(dimethyl)silyl]oxy}methyl)-2-chloro-5-methoxyaniline

To a solution of (4-amino-5-chloro-2-methoxyphenyl)methanol (intermediate 38; 1.5 g, 0.008 mol) in dimethylformamide (35 mL) was added imidazole (1.7 g, 0.02 mol). The mixture was cooled to 0° C. and chloro(isopropyl)dimethylsilane (2.5 g, 0.01 mol) was added dropwise. The reaction was stirred overnight at room temperature. The solvent was removed and the crude was partitioned between water and hexane, the organic layer was washed with water, sodium bicarbonate 4% and brine, dried, filtered and evaporated to dryness. The crude obtained was purified by column chromatography with silica gel, eluting with hexane/ethyl acetate (from 8/1 to 4/1). The title compound was obtained as a yellow solid (58%).

LRMS (m/z): 302(M+1)$^+$.

Intermediate 40

N-[4-({[tert-butyl(dimethyl)silyl]oxy}methyl)-2-chloro-5-methoxyphenyl]-acrylamide To a solution of 4-({[tert-butyl(dimethyl)silyl]oxy}methyl)-2-chloro-5-methoxyaniline (intermediate 39; 0.2 g, 0.68 mmol) in methylene chloride (2 mL) and diethylisopropyl amine (0.17 mL, 1.02 mmol) was added dropwise a solution of acryloyl chloride (0.07 mL, 0.91 mmol) in methylene chloride (1 mL). The mixture was stirred at room temperature for 2 hours. The mixture was diluted with methylene chloride and washed with sodium bicarbonate 4% and water, the solvent was removed under reduced pressure giving a solid as a title compound (94%) which was used in the next step without further purification.

LRMS (m/z): 356(M+1)$^+$.

Intermediate 41 trans-4-((3-(4-((tert-butyl(dimethyl)silyloxy)methyl)-2-chloro-5-methoxy-phenylamino)-3-oxopropyl)(methyl)amino)cyclohexyl hydroxy(di-2-thienyl) acetate A mixture of N-[4-({[tert-butyl(dimethyl)silyl]oxy}methyl)-2-chloro-5-methoxyphenyl]-acrylamide (intermediate 40; 0.9 g, 0.002 mol) and trans-4-(methylamino) cyclohexyl hydroxy(di-2-thienyl)acetate (intermediate 5; 0.7 g, 0.002 mol) in methylene chloride (20 mL) was stirred at 75° C. in a closed vessel for 64 hours. The solvent was evaporated and the crude obtained was purified by column chromatography with silica gel, eluting with chloroform/methanol (from 50/1 to 25/1) to give the title compound as a white-yellow solid (49%).

LRMS (m/z): 707(M+1)$^+$.

Intermediate 42 trans-4-((3-(2-chloro-4-(hydroxymethyl)-5-methoxy-phenylamino)-3-oxopropyl)-(methyl)amino)cyclo-hexyl hydroxy(di-2-thienyl)acetate To a solution of trans-4-((3-(4-((tert-butyl(dimethyl)sily-loxy)methyl)-2-chloro-5-methoxyphenylamino)-3-oxopro-pyl)(methyl)amino)cyclohexyl hydroxy(di-2-thienyl)-ac-etate (intermediate 41; 0.76 mg, 1.08 mmol) in tetrahydrofuran (19 mL) was added hydrochloric acid 1M (3.25 mL, 3.25 mmol). The mixture was stirred at room temperature for 3 hours. The reaction mixture was neutralized by a saturated solution of sodium bicarbonate and extracted with ethyl acetate. The crude obtained was purified by column chromatography with silica gel, eluting with chloroform/methanol 50/1 to give the title compound as an oil (84%).

LRMS (m/z): 593(M+1)$^+$.

Intermediate 43 trans-4-((3-(2-chloro-4-formyl-5-methoxyphe-nylamino)-3-oxopropyl)(methyl)-amino)cyclohexyl hydroxy(di-2-thienyl)acetate To a solution of trans-4-((3-(2-chloro-4-(hydroxymethyl)-5-methoxyphenylamino)-3-oxopropyl)(methyl)amino)cy-clohexyl hydroxy(di-2-thienyl)acetate (intermediate 42; 0.4 g, 0.68 mmol) in chloroform (8.1 mL) was added in portions manganese (IV) oxide (0.62 mg, 7.2 mmol). The heterogeneous mixture was stirred at 45° C. for 3 hours. The mixture was filtered and the solvent was removed under reduced pressure to give the title compound as a yellow solid (88%), which was used in the next step without further purification.

LRMS (m/z): 592(M+1)$^+$.

Intermediate 44 trans-4-((3-(4-(((R)-2-(tert-butyldimethylsilyloxy)-2-(8-hydroxy-2-oxo-1,2-dihydroquinolin-5-yl)ethyl-amino)methyl)-2-chloro-5-methoxyphenylamino)-3-oxopropyl)(methyl)amino)cyclohexyl hydroxy(di-2-thienyl)acetate Obtained as a pale yellow solid (84%) from trans-4-((3-(2-chloro-4-formyl-5-methoxy-phenylamino)-3-oxopropyl) (methyl)amino)cyclohexyl hydroxy(di-2-thienyl)-acetate (intermediate 43; 0.5 g, 0.87 mmol), (2R)-2-{[tert-butyl (dimethyl)-silyl]oxy}-2-(8-hydroxy-2-oxo-1,2-dihydroqui-nolin-5-yl)ethanaminium acetate (prepared according to preparation 8 from US20060035931) (0.5 g, 1.3 mmol) and sodium triacetoxyborohydride (0.66 g, 3.15 mmol) following the experimental procedure as described in intermediate 30, the crude obtained was used in the next step without further purification.

LRMS (m/z): 910(M+1)$^+$.

Example 9 trans-4-((3-(2-chloro-4-(((2R)-2-hydroxy-2-(8-hy-droxy-2-oxo-1,2-dihydroquinolin-5-yl)ethylamino) methyl)-5-methoxyphenylamino)-3-oxopropyl) (methyl)amino)-cyclohexylhydroxy(di-2-thienyl) acetate hydrofluoride

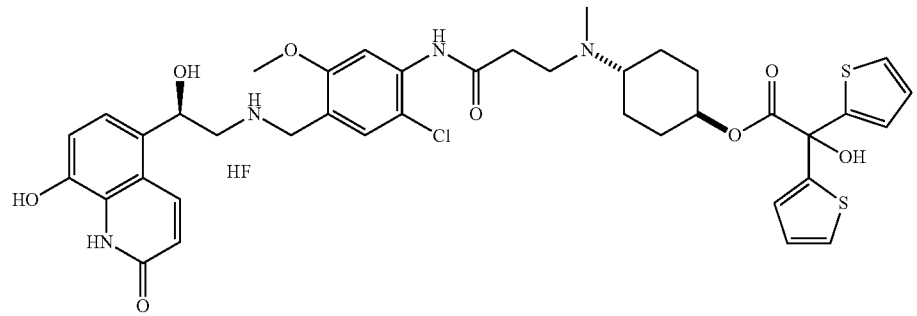

Obtained as a white solid (19%) from trans-4-((3-(4-(((R)-2-(tert-butyldimethylsilyloxy)-2-(8-hydroxy-2-oxo-1, 2-dihydroquinolin-5-yl)ethylamino)methyl)-2-chloro-5-methoxy-phenylamino)-3-oxopropyl)(methyl)amino) cyclohexyl hydroxy(di-2-thienyl)acetate (intermediate 44; 0.89 g, 0.74 mmol) and triethylamine trihydrofluoride (0.48 mL, 2.98 mmol) following the experimental procedure as described in Example 1, followed by a purification by preparative reversed-phase HPLC (System 2) and a lyophilization.

LRMS (m/z): 796(M+1)$^+$.

$^1$H NMR (300 MHz, DMSO-d$_6$) ☐ ppm 1.42 (br. s., 4 H) 1.76 (br. s., 2 H) 1.94 (br. s., 2 H) 2.27 (s, 3 H) 2.45-2.50 (m, 1 H) 2.59 (br. s., 2 H) 2.72 (br. s., 4 H) 3.64-3.76 (m, 5 H) 4.69 (br. s., 1 H) 5.06 (br. s., 1 H) 6.48 (d, J=9.89 Hz, 1 H) 6.87-6.94 (m, 2 H) 6.97 (dd, J=5.08, 3.71 Hz, 2 H) 7.07 (dd, J=3.71, 1.24 Hz, 2 H) 7.33 (s, 1 H) 7.47 (dd, J=5.08, 1.24 Hz, 2 H) 7.79 (s, 1 H) 8.12 (d, J=9.89 Hz, 1 H) 10.67 (s, 1 H)

Intermediate 45

(4-Amino-3-chlorophenyl)methanol

Obtained as a light brown solid (76%) starting from commercially available methyl 4-amino-3-chlorobenzoate (4 g; 0.021 mol) and lithium aluminium hydride (1.09 g; 0.028 mol) in 144 ml tetrahydrofuran following the experimental procedure as described for intermediate 38.
LRMS (m/z): 158(M+1)$^+$.

Intermediate 46

4-({[tert-butyl(dimethyl)silyl]oxy}methyl)-2-chloroaniline

Obtained as a light orange oil (87%) starting from (4-Amino-3-chierophenyl)methanol (intermediate 45; 2.72 g, 0.016 mol), 4.94 g (0.033 mmol) of chloro(tertbutyl)-dimethylsilane and 3.35 g (0.049 mol) of imidazole in 68 ml DMF and following the experimental procedure as described for intermediate 39.
LRMS (m/z): 272(M+1)$^+$.

Intermediate 47

N-[4-({[tert-butyl(dimethyl)silyl]oxy}methyl)-2-chlorophenyl]acrylamide

Obtained as a white crystalline solid (77%) strating from 4-({[tert-butyl(dimethyl)silyl]-oxy}methyl)-2-chloroaniline (intermediate 46; 2 g; 7.36 mmol), acryloyl chloride (0.78 ml; 9.56 mmol) and diethylisopropylamine (1.92 ml, 11.04 mmol) following the experimental procedure as described for intermediate 40.
LRMS (m/z): 326(M+1)$^+$.

Intermediate 48 trans-4-((3-(4-((tert-butyl(dimethyl)silyloxy)methyl)-2-chlorophenylamino)-3-oxopropyl)(methyl)amino)cyclohexyl hydroxy(di-2-thienyl)acetate Obtained as a beige solid (45%) starting from N-[4-({[tert-butyl(dimethyl)silyl]oxy}-methyl)-2-chlorophenyl]-acrylamide (intermediate 47; 0.56 g, 1.73 mmol) and trans-4-(methylamino)cyclohexyl hydroxy(di-2-thienyl)acetate (intermediate 5; 0.5 g, 1.42 mmol) in 14 ml dichloromethane and following the experimental procedure as described for intermediate 41.
LRMS (m/z): 677(M+1)$^+$.

Intermediate 49 trans-4-((3-(2-chloro-4-(hydroxymethyl)-phenylamino)-3-oxopropyl)(methyl)-amino)cyclohexyl hydroxy(di-2-thienyl)acetate Obtained as a beige foam (91%) starting from trans-4-((3-(4-((tert-butyl(dimethyl)-silyloxy)methyl)-2-chlorophenylamino)-3-oxopropyl)(methyl)amino)-cyclohexylhydroxy-(di-2-thienyl)acetate (intermediate 48; 433 mg, 0.64 mmol) and 1M hydrochloric acid (1.9 ml; 1.9 mmol) in tetrahydrofuran (12 mL) following the experimental procedure as described for intermediate 42.
LRMS (m/z): 563(M+1)$^+$.

Intermediate 50 trans-4-((3-(2-chloro-4-formyl-phenylamino)-3-oxopropyl)(methyl)amino)-cyclohexyl hydroxy(di-2-thienyl)acetate Obtained as a light brown oil (94%) starting from trans-4-((3-(2-chloro-4-(hydroxyl-methyl)phenylamino)-3-oxopropyl)(methyl)amino)cyclohexyl hydroxy(di-2-thienyl)-acetate (Intermediate 49; 0.06 g, 0.11 mmol) and manganese (IV) oxide (0.098 mg, 1.13 mmol) in chloroform (1.4 mL) following the experimental procedure as described for intermediate 43.
LRMS (m/z): 561(M+1)$^+$.

Intermediate 51 trans-4-((3-(4-(((R)-2-(tert-butyldimethylsilyloxy)-2-(8-hydroxy-2-oxo-1,2-dihydroquinolin-5-yl)ethylamino)methyl)-2-chlorophenylamino)-3-oxopropyl)(methyl)-amino)cyclohexyl hydroxy(di-2-thienyl)acetate Obtained as a white solid (65%) starting from trans-4-((3-(2-chloro-4-formylpherlylamino)-3-oxopropyl)(methyl)amino)cyclohexyl hydroxy(di-2-thienyl)acetate (intermediate 50; 54 mg, 0.10 mmol), (2R)-2-{[tert-butyl(dimethyl)-silyl]oxy}-2-(8-hydroxy-2-oxo-1,2-dihydroquinolin-5-yl) ethanaminium acetate (prepared according to preparation 8 from US20060035931) (57 mg, 0.14 mmol) and sodium triacetoxyborohydride (77 mg, 0.35 mmol) following the experimental procedure as described in intermediate 30 followed by a purification by preparative reversed-phase HPLC (CHCl3 to CHCl3/MeOH 95:5).
LRMS (m/z): 879(M+1)$^+$.

Example 10 trans-4-((3-(2-chloro-4-(((2R)-2-hydroxy-2-(8-hydroxy-2-oxo-1,2-dihydroquinolin-5-yl)ethylamino) methyl)phenylamino)-3-oxopropyl)(methyl)amino)-cyclohexyl-hydroxy(di-2-thienyl)acetate hydrofluoride

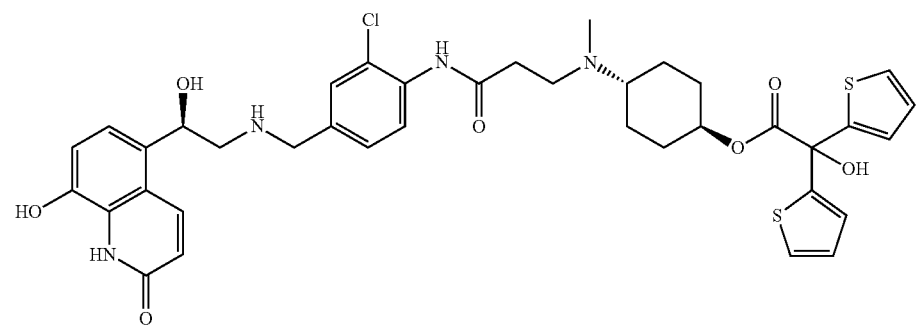 [SMILES: CN(CCC(=O)Nc1ccc(CNC[C@H](O)c2ccc(O)c3[nH]c(=O)ccc23)cc1Cl)[C@H]1CC[C@H](OC(=O)C(O)(c2cccs2)c2cccs2)CC1]

Obtained as a off-white solid (20%) from trans-4-((3-(4-(((R)-2-(tert-butyldimethyl-silyloxy)-2-(8-hydroxy-2-oxo-1,2-dihydroquinolin-5-yl)ethylamino)methyl)-2-chloro-phenylamino)-3-oxopropyl)(methyl)amino)cyclohexyl-hydroxy(di-2-thienyl)-acetate (intermediate 50; 55 mg, 0.06 mmol) and triethylamine trihydrofluoride (0.04 mL, 0.25 mmol) in 3 ml THF following the experimental procedure as described in Example 1, followed by a purification by preparative reversed-phase HPLC (System 2) and a lyophilization.

LRMS (m/z): 765(M+1)$^+$.

$^1$H NMR (300 MHz, DMSO-d$_8$) □ ppm 1.42 (br. s., 4 H) 1,80 (br. s., 2 H) 1.94 (br. s., 2 H) 2.27 (s, 3 H) 2.45-2.50 (m, 1 H) 2.59 (br. s., 2 H) 2.76 (br. s., 4 H) 3.64-3.76 (m, 2 H) 4.69 (br. s., 1 H) 5.31 (br. s., 1 H) 6.54 (d, J=9.89 Hz, 1 H) 6.92-6.97 (m, 2 H) 6.98-7.12 (m, 5 H) 7.25 (s, 1 H) 7.44 (dd, J=5.08, 1.24 Hz, 2 H) 7.65 (s, 1 H) 9.08 (br.s., 1 H) 10.47 (s, 1 H)

Intermediate 52

5-chloro-4-hydroxy-2-methoxybenzoic acid

To a suspension of 4-amino-5-chloro-2-methoxybenzoic acid (25 g; 0.12 mol) in 125 ml of water was added tetrafluoroboric acid (40.5 ml of 48% aqueous solution). The white cake was then cooled to 0° C. and NaNO2 (9.41 g in 75 mL of H2O) was added drop wise and the whole stirred at that temperature for 30 minutes. The white precipitate was collected by filtration. The diazonium salt was suspended in glacial AcOH (1250 mL) and the resulting suspension was stirred at 100° C. for 1 hour (it became a brown solution). It was allowed to stand at RT for two more hours. The solvent was removed under reduced pressure and the brown oily residue suspended in brine (1250 ml) and extracted with EtOAC (3×400 ml). The combined organic layers were dried over magnesium sulphate, filtered and evaporated under reduced pressure to give brown oil. Purification by preparative reversed-phase HPLC (Et2O/EtOH 0/100 to 40/60) afforded 3.0 g (13%) of a red solid.

LRMS (m/z): 203(M+1)$^+$.

Intermediate 53

Methyl 5-chloro-4-hydroxy-2-methoxybenzoate

To a solution of 5-chloro-4-hydroxy-2-methoxybenzoic acid (intermediate 52; 4.17 g: 13.69 mmol) in 123 ml of anhydrous methanol, 2.2 ml of acetyl chloride were added. The solution was stirred at 60° C. under nitrogen atmosphere for 18 hrs. The solution was evaporated under reduced pressure and the residue purified by preparative reversed-phase HPLC (Cl2CH2/EtOAc from 100/0 to 80/20), affording 2.2 g (75%) of a red solid.

LRMS (m/z); 217(M+1)$^+$.

Intermediate 54

2-Chloro-4-(hydroxymethyl)-5-methoxyphenol

A solution of methyl 5-chloro-4-hydroxy-2-methoxybenzoate (intermediate 53; 204 mg; 0.94 mmol) in 4.6 ml of anhydrous THF was stirred with external ice/water bath cooling. A solution of 1M LIAlH4 in THF was dropped in (1.9 ml; 1.9 mmol). After 5 minutes the external bath was removed and the stirring prosecuted for 3 additional hours. With external cooling 0.072 ml of water were added followed by 0.072 ml of 4N NaOH solution and 0.144 additional mi of water. After filtration the cake was thoroughly washed with THF and the filtrates were concentrated giving the title compound in 34% yield, LRMS (m/z): 189(M+1)$^+$.

Intermediate 55

[4-(3-Bromopropoxy)-5-chloro-2-methoxyphenyl] methanol

A mixture of 2-chloro-4-(hydroxymethyl)-5-methoxyphenol (intermediate 54; 0.5 g, 2.61 mmol), 1,3-dibromopropane (1,61 ml; 15.71 mmol) and potassium carbonate (737 mg; 5.23 mmol) in 12 ml acetone was heated to 75° C. in a sealed vessel and stirred for 16 hr. The solids were filtered and washed with acetone and the combined filtrates were concentrated to dryness and purified by preparative reversed-phase HPLC (hexane/EtOAc from 0 to 40%), affording the title compound (80%) as a light yellow oil.

LRMS (m/z): 309(M+1)$^+$.

Intermediate 56 trans-4-[{3-[2-chloro-4-(hydroxymethyl)-5-methoxyphenoxy]propyl}(methyl)-amino]cyclo-hexyl hydroxy(di-2-thienyl)acetate A mixture of [4-(3-bromopropoxy)-5-chloro-2-methoxy-phenyl]methanol (intermediate 55; 386 mg; 1.25 mmol), trans-4-(methylamino)cyclohexyl hydroxy(di-2-thienyl)acetate (intermediate 5; 438 mg, 1.25 mmol) and triethylamine 0.345 ml; 2.49 mmol) in 12 ml acetonitrile and 8.7 ml THF was stirred at 70° C. for 16 hr. An additional amount of intermediate 5 (219 mg; 0.62% mmol) was added and the heating prosecuted for 24 hr. The solvent was evaporated in vacuum and the residue purified by preparative reversed-phase HPLC (hexane/EtOAc from 0 to 40%), affording the title compound (80%) as a light yellow oil.

LRMS (m/z): 309(M+1)$^+$.

Intermediate 57 trans-4-[[3-(2-chloro-4-formyl-5-methoxyphenoxy) propyl](methyl)amino]-cyclohexylhydroxy(di-2-thienyl)acetate A mixture of trans-4-[{3-[2-chloro-4-(hydroxymethyl)-5-methoxyphenoxy]propyl}-(methyl)amino]cyclohexyl hydroxy(di-2-thienyl)acetate (intermediate 56; 418 mg, 0.70 mmol) and manganese (IV) oxide (755 mg; 7.38 mmol) in 9 ml of chloroform was stirred at 45° C. for 3 hr. The solids were filtered and washed with chloroform and the filtrate concentrated to dryness to give the title compound as colourless oil (97%).

LRMS (m/z): 307(M+1)$^+$.

Intermediate 58 trans-4-[{3-[4-({[(2R)-2-{[tert-butyl(dimethyl)silyl] oxy}-2-(8-hydroxy-2-oxo-1,2-dihydroquinolin-5-yl) ethyl]amino}methyl)-2-chloro-5-methoxyphenoxy] propyl}-(methyl)amino]cyclohexyl hydroxy(di-2-thienyl)acetate Obtained as a colourless oil (73%) from trans-4-[[3-(2-chloro-4-formyl-5-methoxy-phenoxy)propyl](methyl)

amino]cyclohexylhydroxy(di-2-thienyl)acetate (intermediate 57; 401 mg; 0.69 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (346 mg, 0.88 mmol) and sodium triacetoxyborohydride (557 mg, 2.50 mmol) following the experimental procedure as described in intermediate 30 followed by a purification by preparative reversed-phase HPLC (CHCl3 to CHCl3/MeOH 95:5).

LRMS (m/z): 896(M+1)⁺.

Example 11 trans-4-[{3-[2-chloro-4-({[(2R)-2-hydroxy-2-(8-hydroxy-2-oxo-1,2-dihydroquinolin-5-yl)ethyl]amino}methyl)-5-methoxyphenoxy]propyl}(methyl)amino]cyclohexyl hydroxy(di-2-thienyl)acetate hydrofluoride

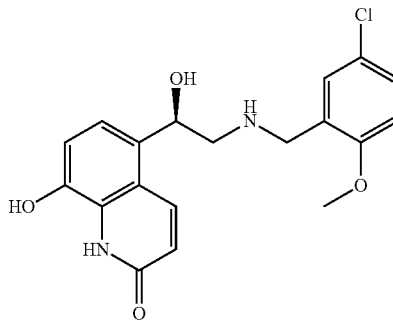
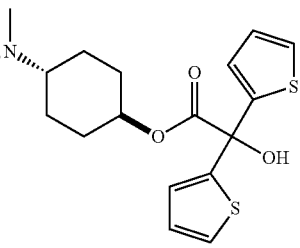

Obtained as a off-white solid (72%) from trans-4-[{3-[4-({[(2R)-2-{[tert-butyl(dimethyl)silyl]oxy}-2-(8-hydroxy-2-oxo-1,2-dihydroquinolin-5-yl)ethyl]amino}-methyl)-2-chloro-5-methoxyphenoxy]propyl}(methyl)amino]cyclohexylhydroxy(di-2-thienyl)acetate (intermediate 58; 59 mg, 0.06 mmol) and triethylamine trihydrofluoride (0.04 mL, 0.28 mmol) in 3 ml THF following the experimental procedure as described in Example 1, followed by a purification by preparative reversed-phase HPLC (System 2) and a lyophilization.

LRMS (m/z): 782(M+1)⁺.

¹H NMR (300 MHz, DMSO-d₆) □ ppm 1.36 (m., 4H); 1.70 (b.s., 2H); 1.82 (m., 2H); 1.89 (b.s.; 2H); 2.17 (s., 3H); 2.37 (b.s., 1H); 2.54 (m., 2H); 2.63 (m., 2H); 3.17 (b.s., 1H); 3.52 (m., 2H); 3.76 (s., 3H); 4.09 (t., 2H): 4.68 (b,s., 1H); 5.01 (m., 1H); 6.47 (d., 1H); 6.7 (s., 1H); 6.90 (d., 1H); 6.93-7.09 (c.s., 5H); 7.24 (s., 1H): 7.46 (d., 1H); 8.11 (d., 1H).

Intermediate 59 tert-Butyl [(5-chloro-4-isocyanato-2-methoxybenzyl)oxy]dimethylsilane

A solution of 4-({[tert-butyl(dimethyl)silyl]oxy}methyl)-2-chloro-5-methoxyaniline (intermediate 39; 300 mg, 1 mmol) in 4 ml of dichloromethane was cooled externally with an ice bath while dropping a solution of triphosgene (108 mg; 0.36 mmol) in 5 ml of dichloromethane. Triethylamine (0.28 ml; 2.01 mmol) was added slowly and the system stirred at room temperature for 3 hr. Half of the solvent is then evaporated in vacuo and 25 ml of pentane added. The white precipitate of ureas was filtered and the filtrate evaporated to dryness giving 311 mg of the title compound that were used without further purification in the next step.

Intermediate 60 trans-4-[(2-hydroxyethyl)(methyl)amino]cyclohexyl hydroxy(di-2-thienyl)acetate

A mixture of trans-4-(methylamino)cyclohexyl hydroxy(di-2-thienyl)acetate (intermediate 5; 300 mg: 0.85 mmol), 2-bromoethanol (0.145 ml; 2.05 mmol) and triethylamine (0.36 ml; 2.68 mmol) in 4.5 ml of acetonitrile and 3.5 ml of THF was stirred at 80° C. in a sealed vessel for 16 hr. Additional amounts of bromoethanol (0.145 ml; 2.05 mmol), triethylamine (0.36 ml; 2.58 mmol), acetonitrile (3.5 ml) and THF (3.5 ml) were added and the stirring and heating prosecuted for 24 additional hours. The solution was evaporated to dryness, dissolved in dichloromethane, washed with brine, dried and concentrated. Purification by preparative reversed-phase HPLC (Cl3CH/MeOH from 1:0 to 9:1) gave 76 as of the title product as a colourless oil.

LRMS (m/z): 396(M+1)⁺.

Intermediate 61 trans-4-[{2-[({[4-({[tert-butyl(dimethyl)silyl]oxy}methyl)-2-chloro-5-methoxy-phenyl]amino}carbonyl)oxy]ethyl}(methyl)amino]cyclohexylhydroxyl(di-2-thienyl)acetate A solution of trans-4-[(2-hydroxyethyl)(methyl)amino]cyclohexyl hydroxy(di-2-thienyl)-acetate (intermediate 60; 290.6 mg; 0.73 mmol) in 5 ml THF was dropped with stirring at room temperature into a solution of tert-butyl[(5-chloro-4-isocyanato-2-methoxybenzyl)oxy]dimethylsilane (intermediate 59; 311 mg; 0.87 mmol) in 5 ml THF. Triethylamine (0228 ml; 1.31 mmol) was added and the stirring prosecuted for 16 hr at 60° C. and for 4 additional hours at 80° C. The solution was concentrated and purified by preparative reversed-phase HPLC (CH₂Cl₂/isopropanol 10:0 to 9:1) to give 66% of the title compound.

LRMS (m/z): 723(M+1)⁺.

Intermediate 62 trans-4-[{2-[({[2-chloro-4-(hydroxymethyl)-5-methoxyphenyl]amino}carbonyl)-oxy]ethyl}(methyl)amino]cyclohexyl hydroxy(di-2-thienyl)acetate To a solution of trans-4-[{2-[({[4-({[tert-butyl(dimethyl)silyl]oxy}methyl)-2-chloro-5-methoxyphenyl]amino}carbonyl)oxy]ethyl}(methyl)amino]cyclohexyl hydroxy(di-2-thienyl)acetate (intermediate 61; 315 mg; 0.44 mmol) in 6 ml THF were added 1.31 ml (1.31 mmol) of aqueous 1M HCl and the system was stirred at room temperature for 2.5 hrs. The solution was basified with aqueous 4% sodium hydrogen carbonate solution and extracted thrice with ethyl acetate. The organic extracts were washed with brine, dried and concentrated. The residue was purified by preparative reversed-phase HPLC (CH2Cl2/isopropanol 10:0 to 9:1) to give 78% of the title compound.

LRMS (m/z): 609(M+1)$^+$.

Intermediate 63 trans-4-[[2-({[(2-chloro-4-formyl-5-methoxyphenyl)amino]carbonyl}oxy)ethyl]-(methyl)amino]cyclohexyl hydroxy(di-2-thienyl)acetate trans-4-[{2-[({[2-chloro-4-(hydroxymethyl)-5-methoxyphenyl]amino}carbonyl)oxy]ethyl}-(methyl)amino]cyclohexyl hydroxy(di-2-thienyl)acetate (intermediate 62; 200 mg; 0.33 mmol) was dissolved in 8 ml dichloromethane and stirred at room temperature in an inert atmosphere. Dess-Martin reagent (170 mg; 0.40 mmol) was added in 3 portions and the reaction stirred for 30 min. Dichloromethane (15 ml) was added, the solution was washed with 4% aqueous sodium hydrogen carbonate solution and vigorously stirred for 1 hour. The solid was filtered and the organic phase of the filtrate was washed with brine, dried and concentrated to give 197 mg of the title compound enough pure to continue with the next step.

LRMS (m/z): 607(M+1)$^+$.

Intermediate 64 trans-4-[{2-[({[4-({[(2R)-2-{[tert-butyl(dimethyl)silyl]oxy}2-(8-hydroxy-2-oxo-1,2-dihydroquinolin-5-yl)ethyl]amino}methyl)-2-chloro-5-methoxyphenyl]amino}-carbonyl)oxy]ethyl}(methyl)amino]cyclohexyl hydroxy(di-2-thienyl)acetate A solution of trans-4-[[2-({[(2-chloro-4-formyl-5-methoxyphenyl)amino]carbonyl}oxy)-ethyl](methyl)amino]cyclohexyl hydroxy(di-2-thienyl)acetate (intermediate 63; 195 mg; 0.28 mmol) and (2R)-2-{[tert-butyl(dimethyl)-silyl]oxy}-2-(8-hydroxy-2-oxo-1,2-dihydroquinolin-5-yl)ethanaminium acetate (prepared according to preparation 8 from US20060035931) (119 mg, 0.36 mmol) in 5 ml THF was stirred at 65° C. for 20 hrs. After cooling the reaction with an ice bath sodium triacetoxyborohydride (195 mg; 0.92 mol) was added in portions. The stirring was prosecuted for 15 minutes at 5° C. and 45 minutes at room temperature. The solution was concentrated to half the volume and 15 ml water and 15 ml of sq. 4% sodium hydrogen carbonate solution were added. The mixture was extracted thrice with ethyl acetate, washed with brine, dried and concentrated. The residue was purified by preparative reversed-phase HPLC (CHCl3/isopropanol 10:0 to 9:1) to give 47% of the title compound.

LRMS (m/z): 925(M+1)$^+$.

Example 12 trans-4-[{2-[({[2-chloro-4-({[(2R)-2-hydroxy-2-(8-hydroxy-2-oxo-1,2-dihydro-quinolin-5-yl)ethyl]amino}methyl)-5-methoxyphenyl]amino}carbonyl)oxy]ethyl}(methyl)amino]cyclohexyl hydroxy(di-2-thienyl)acetate hydrofluoride

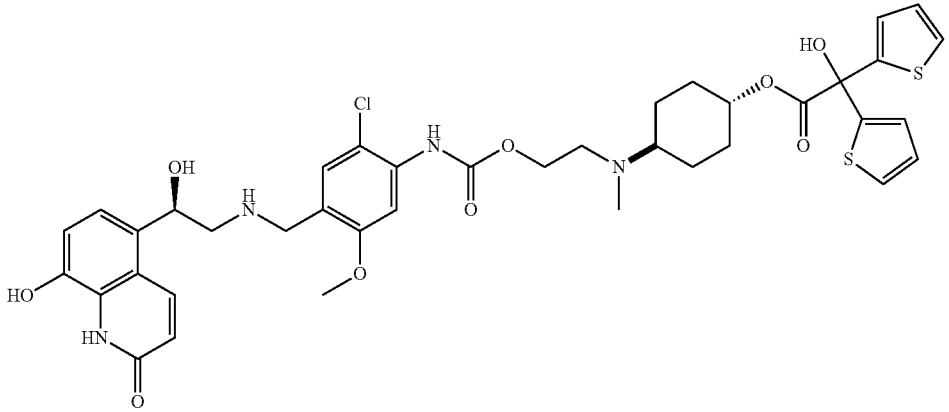

To a solution of trans-4-[{2-[({[4-({[(2R)-2-{[tert-butyl(dimethyl)silyl]oxy}2-(8-hydroxy-2-oxo-1,2-dihydroquinolin-5-yl)ethyl]amino}methyl)-2-chloro-5-methoxyphenyl]amino}-carbonyl)oxy]ethyl}(methyl)amino]cyclohexyl hydroxy(di-2-thienyl)acetate (intermediate 64; 125 mg; 014 mmol) in 5 ml THF triethylamine trihydrofluoride (0.04 mL, 0.28 mmol) was added. After stirring for 20 hr the liquid layer is discarded and the residue is stirred again with 5 ml THF for 1 hr and discarded. Acetonitrile (15 ml) is then added and the stirring prosecuted for 1 hr. The solid was filtered and washed with acetonitrile and diisopropyl ether. The pure title compound was obtained (67%).

LRMS (m/z): 811(M+1)$^+$.

$^1$H NMR (300 MHz, DMSO-d$_6$) δ ppm 1.06 (d., J=6Hz, 2H); 1.39 (m., 3H); 1.75 (m., 2H); 1.93 (m., 2H); 2.24 (s., 3H); 2.44 (b.s., 1H); 2.67 (m., 2H); 2.76 (m., 2H); 3.78 (m., 5H); 4.13 (m., 2H); 4.72 (b.s., 1H); 5.14 (t., 1H); 6.52 (d., J=12 Hz, 1H); 6.90-7.03 (m., 3H); 7.09 (m., 3H); 3H); 7.23 (s., 1H); 7.28 (b.s., 1H): 7.40 (s., 1H): 7.49 (d., J=6 Hz; 1H); 8.15 (d., J=12 Hz, 1H); 9.01 (s., 1H); 10.39 (b.s., 1H).

Intermediate 65

N,N-dibenzyl-1,4-dioxaspiro[4,5]decan-8-amine dibenzyl(1,4-dioxaspiro[4.5]dec-8-yl)amine To a solution of 1,4-dioxaspiro[4.5]decan-8-one (25 g, 0.16 mol) in 1,2-dichloroethane (396 mL) was added dibenzylamine (32.3 mL, 0.16 mol) under nitrogen atmosphere and the resulting solution was stirred for 2 hours at room temperature. Then sodium triacetoxyborohydride (55.4 g, 0.25 mol) was added portionwise and the reaction mixture was stirred at room temperature overnight. A mixture of bicarbonate and dichloromethane (1:1) was added to the reaction mixture and it was stirred for half an hour, then the organic phase was extracted and washed with bicarbonate and brine, dried, filtered and the organic solvent was evaporated under reduced pressure. The resulting oil was precipitated with hexane obtaining a white solid as a title compound (80%), which was used in the next step without further manipulation.

LRMS (m/z): 338 (M+1)$^+$.

Intermediate 66

4-(dibenzylamino)cyclohexanone

N,N-dibenzyl-1,4-dioxaspiro[4.5]decan-8-amine dibenzyl(1,4-dioxaspiro[4.5]dec-8-yl)-amine (intermediate 65; 43.6 g, 0.13 mol) was suspended in hydrochloric acid (35%, 49.4 mL, 0.59 mol), the resulting mixture was stirred at 100° C. during 8 hours. The mixture was cooled with ice-water and basified until pH~8 with potassium carbonate, then was extractes with chloroform. The organic layer was evaporated to dryness obtaining an oil which was purified by column chromatography with silica gel, eluting with hexane:ethyl acetate (from 98/2 to 90/10) to give the title compound as a yellow solid (72%).

LRMS (m/z): 294 (M+1)$^+$.

Intermediate 67 trans-4-(dibenzylamino)-1-methylcyclohexanol

To a solution of 4-(dibenzylamino)cyclohexanone (intermediate 66; 10 g, 32 mmol) in anhydride tetrahydrofuran was added slowly methyl lithium 1.6M in diethyl ether (30 mL, 48 mmol) under argon atmosphere at −78° C., and the resulting mixture was stirred at −78° C. during 4 hours. Then a saturated solution of ammonium chloride was added and the mixture was stirred overnight at room temperature. The organic solvent was evaporated and the crude obtained was treated with water and chloroform. The organic layer was dried with sodium sulphate, filtrated and evaporated obtaining an oil, which was purified by column chromatography with silica gel, eluting with hexane: ethyl acetate (from 0% of hexane to 31% of ethyl acetate) obtaining two different fractions, The first one corresponding to cis product and the other one to trans product as a white solid, which was the title compound (55%).

LRMS (m/z): 310 (M+1)$^+$.

Intermediate 68 trans-4-amino-1-methylcyclohexanol

To a solution of trans-4-(dibenzylamino)-1-methylcyclohexanol (intermediate 67; 5.7 g, 17.68 mmol) in anhydride ethanol (125 mL) was added palladium hydroxide (1.7 g, 2.44 mmol) under nitrogen atmosphere. The reaction mixture was stirred vigorously under hydrogen atmosphere overnight at room temperature. The mixture was filtered through celite and washed with ethanol. The solvent was evaporated under reduced pressure obtaining a white solid as a title compound (98%), which was used in the next step without further purification.

LRMS (m/z): 130 (M+1)$^+$.

Intermediate 69 tert-butyl(trans-4-hydroxy-4-methylcyclohexyl)carbamate

To a suspension of trans-4-amino-1-methylcyclohexanol (intermediate 68; 2.3 g, 18.27 mmol) in acetonitrile (33 mL) was added under argon atmosphere di-tert-butyl dicarbonate (4.3 g, 20.11 mmol). The mixture was stirred vigorously overnight at room temperature. The precipitate was filtrated and washed with hexane: ethyl acetate (3:1) obtaining a solid which was purified by column chromatography with silica gel, eluting with hexane: ethyl acetate (from 0% to 100% of ethyl acetate). The title compound was obtained as a white solid (90%).

$^1$H NMR (300 MHz, CHLOROFORM-d)

Intermediate 70 trans-1-methyl-4-(methylamino)cyclohexanol tert-butyl(trans-4-hydroxy-4-methylcyclohexyl)carbamate (intermediate 69; 3.6 g, 16.09 mmol) was added to a suspension of lithium aluminium hydride (3.1 g, 82.21 mmol) in anh. tetrahydrofuran at room temperature. Then the mixture was refluxed overnight. The mixture was cooled to room temperature and the excess of hydride was destroyed, and filtrated. The solvent was removed under reduced pressure obtaining an oil which solidifies. The title compound was obtained as a solid (98%).

$^1$H NMR (300 MHz, CHLOROFORM-d)

Intermediate 71 tert-butyl(trans-4-hydroxy-4-methylcyclohexyl) methylcarbamate

Obtained as a white solid (78%) from trans-1-methyl-4-(methylannino)cyclohexanol (intermediate 71; 2.5 g, 17.4 mmol) and di-tert-butyl dicarbonate (4.1 g, 19.2 mmol) following the experimental procedure as described in intermediate 69 (reaction time: 2 hours), followed by a purification by column chromatography with silica gel, eluting with chloroform/methanol (1:1).

$^1$H NMR (300 MHz, CHLOROFORM-d)

Intermediate 72 trans-4-[(tert-butoxycarbonyl)(methyl)amino]-1-methylcyclohexyl oxo(2-thienyl)-acetate To a solution of 2-oxo-2-(tipophen-2-yl)acetic acid (2.13 g, 13.64 mmol) in chloroform stabilized with amylenes (25 mL) and two drops of anhydride dimethylformamide was added dropwise a solution of oxalyl chloride (1.78 mL, 20.47 mmol) in chloroform/amylenes at low temperature. The mixture was stirred for 15 minutes at low temperature and for 2 hours at room temperature. The mixture was evaporated to dryness and the crude obtained was dissolved in anhydride methylen chloride (21 mL) and added dropwise at low temperature to a solution of tert-butyl(trans-4-hydroxy-4-methylcyclohexyl)methylcarbamate (intermediate 71; 2.77 g, 11.3 mmol) in anhydride methylene chloride (25 mL) and triethylamine (3.9 mL, 28.42 mmol). The mixture was stirred at room temperature overnight. The crude was partitioned with water and methylen chloride and the organic layer was washed with bicarbonate 4% and water, filtrated and evaporated to dryness giving a brown oil, which was purified by column chromatography with silica gel, eluting with hexane:ethylacetate (1:1). The title compound was obtained as an orange oil (62%).

LRMS (m/z): 382(M+1)$^+$.

Intermediate 73 trans-4-[(tert-butoxycarbonyl)(methyl)amino]-1-methylcyclohexyl hydroxy(di-2-thienyl)acetate To a suspension of magnesium (0.21 g, 8.64 mmol) in anhydride tetrahydrofuran (14.7 mL) in argon atmosphere was added dropwise the 20% of the solution of 2-bromotiophene (0.83 mL, 8.57 mmol) in anhydride tetrahydrofuran (9.8 mL), after some minutes the rest of the 2-bromotiophene solution was added dropwise. The mixture was stirred at 75° C. for 1 hour and then the reaction was cooled to room temperature and added dropwise at low temperature to a solution of trans-4-[(tert-butoxycarbonyl)(methyl)amino]-1-methylcyclohexyl oxo(2-thienyl)acetate (intermediate 72; 2.65 g, 6.6 mmol) in anhydride tetrahydrofuran (18.4 mL). Once the addition was finished, the mixture was stirred 1 hour at room temperature and 1 hour refluxing. The crude reaction was cooled and a saturated solution of ammonium chloride was added, then the crude was extracted with ether and the organic layer was washed with brine, dryed and filtered. The organic solvent was removed under reduced pressure giving a crude which was purified by column chromatography with silica gel, eluting with hexane:ethylacetate (1:1). The title compound was obtained as an orange oil (92%).

LRMS (m/z): 466(M+1)$^+$.

Intermediate 74 trans-1-methyl-4-(methylamino)cyclohexyl hydroxy(di-2-thienyl)acetate

Obtained as a solid form trans-4-[(tert-butoxycarbonyl)(methyl)amino]-1-methyl-cyclohexyl-hydroxy(di-2-thienyl)acetate (intermediate 73; 0.18 g, 0.39 mmol) and hydrogen chloride 4M in dioxane (0.49 mL, 1.96 mmol) following the experimental procedure as described in intermediate 5. The crude obtained was purified by column chromatography with silica gel, eluting with chloroform/methanol (1:1).

(m/z): 366(M+1)$^+$.

Intermediate 75 trans-4-[(3-{[4-({[tert-butyl(dimethyl)silyl]oxy}methyl)-2-chloro-5-methoxyphenyl]-amino}-3-oxopropyl)(methyl)amino]-1-methylcyclohexyl hydroxy(di-2-thienyl-)acetate Obtained as a yellow oil (69%) from trans-1-methyl-4-(methylamino)cyclohexyl hydroxy(di-2-thienyl)acetate (intermediate 74; 92 mg, 0.24 mmol) and N-[4-({[tert-butyl(dimethyl)silyl]oxy}methyl)-2-chloro-5-methoxyphenyl] acrylamide (intermediate 40; 104 mg, 0.29 mmol) following the experimental procedure as described in intermediate 41. The crude obtained was purified by column chromatography with silica gel, eluting with chloroform/hexane (1:1).

LRMS (m/z): 722(M+1)$^+$.

Intermediate 76 trans-4-[(3-{[2-chloro-4-(hydroxymethyl)-5-methoxyphenyl]amino}-3-oxopropyl)-(methyl)amino]-1-methylcyclohexyl hydroxy(di-2-thienyl)acetate Obtained as a colorless oil (73%) from trans-4-[(3-{[4-({[tert-butyl(dimethyl)silyl]oxy}methyl)-2-chloro-5-methoxyphenyl]amino}-3-oxopropyl)-(methyl)amino]-1-methylcyclohexyl hydroxy(di-2-thienyl)acetate (intermediate 75; 119 mg, 0.16 mmol) and hydrochloric acid 1M (0.49 mL, 0.5 mmol) following the experimental procedure as described in intermediate 42. The crude obtained was purified by column chromatography with silica gel, eluting with chloroform/methanol (15:1).

LRMS (m/z): 608(M+1)$^+$.

Intermediate 77 trans-4-[{3-[(2-chloro-4-formyl-5-methoxyphenyl)amino]-3-oxopropyl}-(methyl)amino]-1-methylcyclohexyl hydroxy(di-2-thienyl)acetate Obtained as a colorless oil (97%) from trans-4-[(3-{[2-chloro-4-(hydroxymethyl)-5-methoxyphenyl]amino}-3-oxopropyl)(methyl)amino]-1-methylcyclohexyl hydroxy(di-2-thienyl)acetate (intermediate 76; 432 mg, 0.7 mmol) and manganese (IV) oxide (754 mg, 7.37 mmol) following the experimental procedure as described in intermediate 43. The crude obtained was used in the next step without purification.

LRMS (m/z): 606(M+1)$^+$.

Intermediate 78 trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-3-oxopropyl)(methyl)amino]-1-methylcyclohexyl hydroxy(di-2-thienyl)acetate Obtained as a colorless oil (85%) from trans-4-[{3-[(2-chloro-4-formyl-5-methoxyphenyl)amino]-3-oxopropyl}(methyl)amino]-1-methylcyclohexyl hydroxy(di-2-thienyl)acetate (intermediate 77, 0.4 g, 0.67 mmol), (2R)-2-{[tertbutyl(dimethyl)silyl]oxy}-2-(8-hydroxy-2-oxo-1,2-dihydroquinolin-5-yl)ethanaminium acetate (prepared according to preparation 8 from US20060035931) (0.4 g, 1.01 mmol) and sodium triacetoxyborohydride (0.54 g, 2.41 mmol) following the experimental procedure as described in intermediate 30, the crude obtained was purified by column chromatography with silica gel, eluting with chloroform/methanol (10:1).

LRMS (m/z): 924(M+1)$^+$.

Example 13 trans-4-[(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)(methyl)amino]-1-methylcyclohexyl hydroxy(di-2-thienyl)acetate

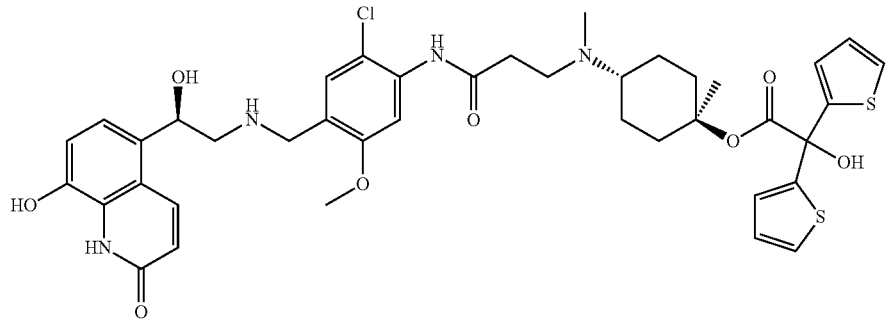 [SMILES: COc1cc(NC(=O)CCN(C)[C@H]2CC[C@](C)(OC(=O)C(O)(c3cccs3)c3cccs3)CC2)c(Cl)cc1CNC[C@H](O)c1ccc(O)c2[nH]c(=O)ccc12]

Obtained as a colorless oil (62%) from trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-3-oxopropyl)(methyl)amino]-1-methylcyclohexyl hydroxy(di-2-thienyl)acetate (intermediate 78, 0.43 g, 0.46 mmol) and triethylamine trihydrofluoride (0.32 mL, 1.98 mmol) following the experimental procedure as described in Example 1, followed by a purification by preparative reversed-phase HPLC (System 2).

LRMS (m/z): 809(M±1)$^+$.

$^1$H NMR (300 MHz, DMSO-d$_6$) ☐ ppm 1.45 (br. s., 11 H) 1.70 (t., 3 H) 1.96 (br. s., 3 H) 2.24 (s, 3 H) 2.45-2.50 (b.s., 3 H) 2.63-2.77 (m., 5 H) 3.63-3.70 (m, 4 H) 4.11 (m, 1H) 5.02 (m, 1 H) 5.34 (br. s., 1 H) 6.47 (d, J=9.89 Hz, 1 H) 6.89 (m, 2 H) 6.97 (dd, J=5.08, 3.71 Hz, 2 H) 7.07 (dd, J=3.71, 1.24 Hz, 2 H) 7.30 (s, 1 H) 7.45 (dd, J=5 Hz, 2 H) 7.68 (s, 1 H) 8.12 (d, J=9 Hz, 1 H) 10.36 (b.s, 2 H)

Intermediate 79

N-[4-(hydroxymethyl)phenyl]acrylamide

Obtained as a solid (82%) from (4-aminophenyl)methanol (0.5 g, 4.06 mmol), acryloyl chloride (0.3 mL, 4.06 mmol) and diethylisopropyl amine (1.4 mL, 8.1 mmol) following the experimental procedure as described in intermediate 40. The crude obtained was used in the next step without further purification.

LRMS (m/z): 178(M+1)$^+$.

Intermediate 80 trans-4-[(3-{[4-(hydroxymethyl)phenyl]amino}-3-oxopropyl)(methyl)-amino]cyclohexyl hydroxy(di-2-thienyl)acetate To a solution of N-[4-(hydroxymethyl)phenyl]acrylamide (intermediate 79; 0.3 g, 1.7 mmol) in tetrahydrofuran (6 mL) was added trans-4-(methylamino)cyclohexyl hydroxy(di-2-thienyl)acetate (intermediate 5; 0.5 g, 1.42 mmol). The mixture was placed in a sealed vessel and stirred for 4 days at 75° C. The solvent was removed under reduced pressure and the crude obtained was purified by preparative reversed-phase HPLC (System 2) to give the title compound (34%).

LRMS (m/z): 529(M+1)$^+$.

Intermediate 81 trans-4-[{3-[(4-formylphenyl)amino]-3-oxopropyl}(methyl)amino]cyclohexyl hydroxy(di-2-thienyl)acetate Obtained as an oil (96%) from trans-4-[(3-{[4-(hydroxymethyl)phenyl]amino}-3-oxopropyl)(methyl)amino]cyclohexyl hydroxy(di-2-thienyl)acetate (intermediate 80; 0.25 g, 0.47 mmol) and manganese (IV) oxide (0.4 g, 4.7 mmol) following the experimental procedure as described in intermediate 43. The crude obtained was used in the next step without further purification.

LRMS (m/z): 527(M+1)$^+$.

Intermediate 82 trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-3-oxopropyl)(methyl)-amino]cyclohexyl hydroxy(di-2-thienyl)acetate Obtained as foam (31%) from trans-4-[{3-[(4-formylphenyl)amino]-3-oxopropyl}-(methyl)amino]cyclohexyl hydroxy(di-2-thienyl)acetate (intermediate 81; 0.24 g, 0.46 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (0.2 g, 0.68 mmol) and sodium triacetoxyborohydride (0.34 g, 1.64 mmol) following the experimental procedure as described in intermediate 30, the crude obtained was purified by column chromatography with silica gel.

LRMS (m/z): 846(M+1)$^+$.

Example 14 trans-4-[(3-{[4-({[(2R)-2-hydroxy-2-(8-hydroxy-2-oxo-1,2-dihydroquinolin-5-yl-)ethyl]amino}methyl)phenyl]amino}-3-oxopropyl)(methyl)amino]cyclohexyl hydroxy(di-2-thienyl)acetate hydrofluoride (1:2)

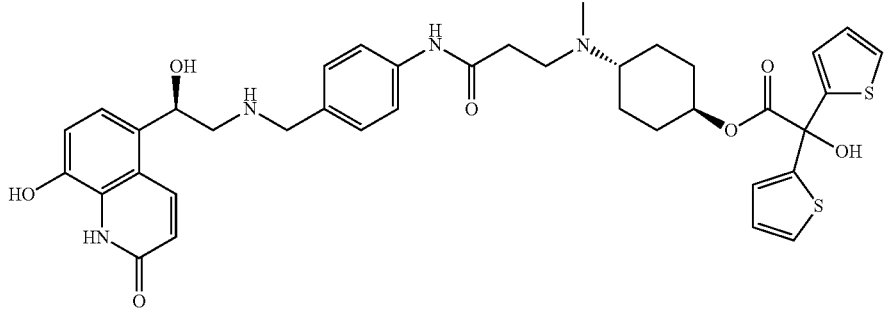 [SMILES: CN(CCC(=O)Nc1ccc(CNC[C@H](O)c2ccc(O)c3[nH]c(=O)ccc23)cc1)[C@H]1CC[C@H](OC(=O)C(O)(c2cccs2)c2cccs2)CC1]

Obtained as a colorless oil (82%) from trans-4-[(3-{[4-({[(2R)-2-{[tert-butyl(dimethyl)silyl]oxy}-2-(8-hydroxy-2-oxo-1,2-dihydroquinolin-5-yl)ethyl]amino}-methyl)phenyl]amino}-3-oxopropyl)(methyl)amino]cyclohexyl hydroxy(di-2-thienyl)-acetate (intermediate 82, 0.12 g, 0.14 mmol) and triethylamine trihydrofluoride (0.07 mL, 0.43 mmol) following the experimental procedure as described in Example 1, followed by a purification by preparative reversed-phase HPLC (System 2).

LRMS (m/z): 731(M+1)$^+$.

$^1$H NMR (300 MHz, DMSO-d$_6$) □ ppm 1.34-1.46 (br. s., 4 H) 1.76 (m, 1 H) 1.94 (br. s., 2 H) 2.27 (br. s., 3 H) 2.48-2.52 (b.s. 5H) 2.72-2.92 (m, 2 H) 4.71 (m., 1 H) 5.26 (br. s., 1 H) 6.52 (d, J=9 Hz, 1H) 6.91-7.00 (m., 3H) 7.05.-7.11 (m., 3 H) 7.27 (s. 1H) 7.36-7.42 (m, 2 H) 7.47 (d, J=6 Hz, 1 H) 7.57 (d, J=9 Hz. 1 H) 8.10 (dd, J=5.08, 1.24 Hz, 1 H) 10.15 (br.s., 1 H) 10.44 (s, 1 H)

Intermediate 83

4-bromo-N-[4-({[tert-butyl(dimethyl)silyl]oxy}methyl)-2-chloro-5-methoxyphenyl]-butanamide To a solution of 4-({[tert-butyl(dimethyl)silyl]oxy}methyl)-2-chloro-5-methoxyaniline (intermediate 39; 0.75 g, 2.48 mmol) in tetrahydrofuran (20 mL) and triethylamine (0.38 mL, 2.73 mmol) was added under nitrogen atmosphere at 0° C. 4-bromobutanoyl chloride (0.32 mL, 2.76 mmol). The mixture was stirred for half an hour. Ethyl acetate was added to the mixture and the organic layer was washed with bicarbonate and brine, dried and the solvent was removed under reduced pressure. The title compound was obtained (97%) and it was used in the next step without further purification.

LRMS (m/z): 451(M+1)$^+$.

Intermediate 84 trans-4-[(4-{[4-({[tert-butyl(dimethyl)silyl]oxy}methyl)-2-chloro-5-methoxyphenyl]-amino}-4-oxobutyl)(methyl)amino]cyclohexyl hydroxy(di-2-thienyl)acetate Obtained as an oil (4%) from 4-bromo-N-[4-({[tert-butyl(dimethyl)silyl]oxy}methyl)-2-chloro-5-methoxyphenyl] butanamide (intermediate 83; 2.2 g, 4.4 mmol), trans-4-(methylamino)cyclohexyl hydroxy(di-2-thienyl)acetate (intermediate 5; 1.03 g, 2.84 mmol) and triethylamine (1.2 mL, 8.82 mmol) following the experimental procedure as described in intermediate 6. The crude obtained was purified by preparative reversed-phase HPLC (System 2).

LRMS (m/z): 722(M+1)$^+$.

Intermediate 85 trans-4-[(4-{[2-chloro-4-(hydroxymethyl)-5-methoxyphenyl]amino}-4-oxobutyl)-(methyl)amino] cyclohexyl hydroxy(di-2-thienyl)acetate To a solution of trans-4-[(4-{[4-({[tert-butyl(dimethyl)silyl]oxy}methyl)-2-chloro-5-methoxyphenyl]amino}-4-oxobutyl)(methyl)amino]cyclohexyl hydroxy(di-2-thienyl)-acetate (intermediate 84; 90 mg, 0,12 mmol) in tetrahydrofuran (3.5 mL) was added triethylamine trihydrofluoride (0.55 mL, 5.46 mmol). The mixture was stirred at room temperature overnight. The solvent was removed under reduced pressure and the crude obtained was purified by preparative reversed-phase HPLC (System 2), to give the title compound (23%).

LRMS (m/z): 608(M+1)$^+$.

Intermediate 86 trans-4-[{4-[(2-chloro-4-formyl-5-methoxyphenyl)amino]-4-oxobutyl}(methyl)-amino]cyclohexyl hydroxy(di-2-thienyl)acetate Obtained as an oil (84%) from trans-4-[(4-{[2-chloro-4-(hydroxymethyl)-5-methoxyphenyl]amino}-4-oxobutyl)(methyl)amino]cyclohexyl hydroxy(di-2-thienyl)-acetate (intermediate 85; 0.68 g, 1.12 mmol) and manganese (IV) oxide (1.95 g, 22.39 mmol) following the experimental procedure as described in intermediate 43 (reaction time: 32 hours). The crude obtained was used in the next step without further purification.

LRMS (m/z): 606(M+1)$^+$.

Intermediate 87 trans-4-[(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)(methyl)amino]cyclohexyl hydroxy(di-2-thienyl)acetate Obtained as a brown solid (47%) from trans-4-[{4-[(2-chloro-4-formyl-5-methoxyphenyl)amino]-4-oxobutyl}(methyl)amino]cyclohexyl hydroxy(di-2-thienyl)-acetate (intermediate 86; 0.35 g, 0.4 mmol), 5-((1R)-2-amino-1-{[tert-butyl(dimethyl)-silyl]oxy}ethyl)-8-hydroxyquinolin-2(1H)-one (prepared according to preparation 8 from US20060035931) (0.2 g, 0.51 mmol) and triacetoxyborohydride (0.28 g, 1.32 mmol) following the experimental procedure as described in intermediate 30. The crude obtained was purified by column chromatography with silica gel, eluting with chloroform/methanol (95:5).

LRMS (m/z): 924(M+1)$^+$.

Example 15 trans-4-[(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)(methyl)amino]-cyclohexyl hydroxy(di-2-thienyl)acetate

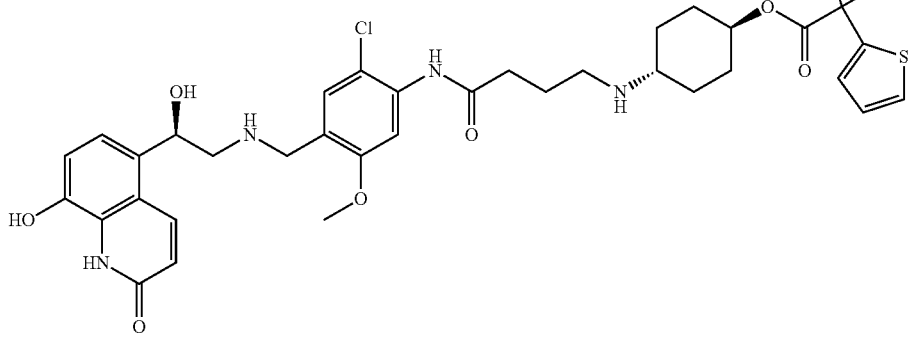

Obtained as a yellow solid (50%) from trans-4-[(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)(methyl)amino]cyclohexyl hydroxy(di-2-thienyl)acetate (intermediate 87, 0.18 g, 0.17 mmol) and triethylamine trihydrofluoride (0.08 mL, 0.52 mmol) following the experimental procedure as described in Example 1, followed by a purification by preparative reversed-phase HPLC (System 2).

LRMS (m/Z): 795(M+1)$^+$.

$^1$H NMR (300 MHz, DMSO-d$_6$) □ ppm 1.35 (br. s., 6 H) 1.71 (br. s., 4 H) 1.92 (br. s., 2 H) 2.06-2.19 (c.s, 4 H) 2.38 (br.s., 4 H) 2.65 (m., 1 H) 3.61-3.73 (m, 4 H) 4.68 (br. s., 1 H) 5.04 (br. s., 1 H) 5.37 (br.s., 1H) 6.48 (d, J=9.89 Hz, 1 H) 6.87-7.10 (c.s., 4H) 7.26 (br.s., 1 H) 7.32 (d., J=5.1 1 H) 7.47 (d., J=5.08, 1 H) 8.13 (d, J=9.89 Hz, 1H) 9.39 (s, 1 H)

Intermediate 88

4-amino-5-fluoro-2-methoxybenzonitrile

To a mixture of methanol (10.48 mL, 0.25 mol) and anh. tetrahidrofuran (60 mL) was added dropwise a solution of potassium tert-butilate (6.76 g, 0.05 mol) in anh. tetrahidrofuran (52 mL) at 0° C. under nitrogen atmosphere. The mixture was stirred for 10 minutes at room temperature and then 4-amino-2,5-difluorobenzonitrile (4 g, 0.02 mol) was added. The reaction mixture was stirred at 70° C. for 3 hours. The solvent was partially removed and ether was added into the mixture. The organic layer was washed with bicarbonate and brine, dried and filtered. The organic solvent was removed under reduced pressure to give the title compound as a yellow solid (97%), which was used in the next step without further purification.

LRMS (m/z): 167(M+1)$^+$.

Intermediate 89

4-amino-5-fluoro-2-methoxybenzoic acid

To a solution of 4-amino-5-fluoro-2-methoxybenzonitrile (intermediate 88; 5.3 g, 0.03 mol) in ethanol (20 mL) was added sodium hydroxide 8M (27.9 mL, 0.22 mol), the mixture was placed in a sealed vessel and heated to 110° C. for 20 hours. The solvent was removed under reduced pressure and the crude obtained was partitioned between water and ether. The aqueous layer was acidified by hydrochloric acid 6N until pH 4 and the crude was extracted with ethyl acetate, dried, filtered and evaporated under reduced pressure giving the title compound as a yellow solid (80%), which was used in the next step without further purification.

LRMS (m/z): 186(M+1)$^+$.

Intermediate 90 ethyl 4-amino-5-fluoro-2-methoxybenzoate

Obtained as a brown solid (91%) from 4-amino-5-fluoro-2-methoxybenzoic acid (intermediate 89; 4.78 g, 0.025 mol) and hydrogen chloride 1.25M in ethanol (153 mL, 0.19 mol) following the experimental procedure as described in intermediate 37. The crude obtained was used in the next step without further purification.

LRMS (m/z): 214(M+1)$^+$.

Intermediate 91

(4-amino-5-fluoro-2-methoxyphenyl)methanol

Obtained as a brown solid (56%) from ethyl 4-amino-5-fluoro-2-methoxybenzoate (intermediate 90; 0.3 g, 1.41 mmol) and lithium aluminium hydride (69 mg, 1.83 mmol) following the experimental procedure as described in intermediate 38. The crude obtained was used in the next step without further purification.

LRMS (m/z): 172(M+1)$^+$.

Intermediate 92

[4-({[tert-butyl(dimethyl)silyl]oxy}methyl)-2-fluoro-5-methoxyphenyl]amine

To a solution of (4-amino-5-fluoro-2-methoxyphenyl) methanol (intermediate 91; 1.49 g, 8.7 mmol) in tetrahidrofuran (117 mL) was added dimethylaminopiridine (0.1 g, 0.81 mmol) and triethylamine (3.4 mL, 24.3 mmol). Then the mixture was cooled to 0° C. and tert-butylchlorodimethylsilane (2.45 g, 16.2 mmol) was added under argon atmosphere. The mixture was stirred 2 hours at room temperature. The solvent was removed under reduced pressure and the crude obtained was purified by column chromatography with silica gel, eluting with hexane/ether (from 0% to 100%). The title compound was obtained as an pale-orange solid (82%).

LRMS (m/z); 286(M+1)$^+$.

Intermediate 93

N-[4-({[tert-butyl(dimethyl)silyl]oxy}methyl)-2-fluoro-5-methoxyphenyl]-acrylamide Obtained as a white solid (88%) from [4-({[tert-butyl(dimethyl)silyl]oxy}methyl)-2-fluoro-5-methoxyphenyl] amine (intermediate 92; 0.5 g, 1.75 mmol), acryloryl chloride (0.174 g, 1.93 mmol) and diisopropylethylamine (0.45 mL, 2.63 mmol) following the experimental procedure as described in intermediate 40. The crude obtained was purified by column chromatography with silica gel, eluting with hexane/ether (from 0% to 100%)

LRMS (m/z): 340(M+1)$^+$.

Intermediate 94 trans-4-[(3-{[4-({[tert-butyl(dimethyl)silyl]oxy}methyl)-2-fluoro-5-methoxyphenyl]-amino}-3-oxopropyl)(methyl)amino]cyclohexyl hydroxy(di-2-thienyl)acetate Obtained as a solid (28%) from N-[4-({[tert-butyl(dimethyl)silyl]oxy}methyl)-2-fluoro-5-methoxyphenyl]acrylamide (intermediate 93; 576 mg, 1.67 mmol) and trans-4-(methylamino)cyclohexyl hydroxy(di-2-thienyl)acetate (intermediate 5; 455 mg, 1.29 mmol) following the experimental procedure as described in intermediate 80. The crude obtained was purified by column chromatography with silica gel, eluting with hexane/chloroform:methanol (15:1) (from 0% to 100%).

LRMS (m/z): 691(M+1)$^+$.

Intermediate 95 trans-4-[(3-{[2-fluoro-4-(hydroxymethyl)-5-methoxyphenyl]amino}-3-oxopropyl)-(methyl)amino]cyclohexyl hydroxy(di-2-thienyl)acetate Obtained as an oil (94%) from trans-4-[(3-{[4-({[tert-butyl(dimethy)silyl]oxy}methyl)-2-fluoro-5-methoxyphenyl]amino}-3-oxopropyl)(methyl)amino]cyclohexyl hydroxy(di-2-thienyl)acetate (intermediate 94; 303 mg, 0.44 mmol) and hydrochloric said 1M (1.32 mL, 1.32 mmol) following the experimental procedure as described in intermediate 42. The crude obtained was purified by column chromatography with silica gel, eluting with chloroform:methanol (15:1).

LRMS (m/z): 577(M+1)$^+$.

Intermediate 96 trans-4-[{3-[(2-fluoro-4-formyl-5-methoxyphenyl)amino]-3-oxopropyl}-(methyl)amino]cyclohexyl hydroxy(di-2-thienyl)acetate Obtained as an oil (88%) from trans-4-[(3-{[2-fluoro-4-(hydroxymethyl)-5-methoxyphenyl]amino}-3-oxopropyl)(methyl)amino]cyclohexyl hydroxy(di-2-thienyl)-acetate (intermediate 85; 439 mg, 0.76 mmol) and manganese (IV) oxide (700 mg, 8.05 mmol) following the experimental procedure as described in intermediate 43.

LRMS (m/z): 577(M+1)$^+$.

Intermediate 97 trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-fluoro-5-methoxyphenyl]amino}-3-oxopropyl)(methyl)amino]cyclohexyl hydroxy(di-2-thienyl)acetate Obtained as an oil (57%) from trans-4-[{3-[(2-fluoro-4-formyl-5-methoxyphenyl)amino]-3-oxopropyl}(methyl)amino]cyclohexyl hydroxy(di-2-thienyl)acetate (intermediate 96; 392 mg, 0.68 mmol), (2R)-2-{[tert-butyl(dimethyl)silyl]oxy}-2-(8-hydroxy-2-oxo-1,2-dihydroquinolin-5-yl) ethanaminium acetate (prepared according to preparation 8 from US20060035931) (339 mg, 0.86 mmol) and sodium triacetoxyhydroborane (547 mg, 2.46 mmol) following the experimental procedure as described in intermediate 30, followed by a purification by preparative reversed-phase HPLC (System 2).

LRMS (m/z); 894(M+1)$^+$.

Example 16 trans-4-[(3-{[2-fluoro-4-({[(2R)-2-hydroxy-2-(6-hydroxy-2-oxo-1,2-dihydroquinolin-5-yl)ethyl]amino}methyl)-5-methoxyphenyl]amino}-3-oxopropyl)(methyl)amino]-cyclohexyl hydroxy(di-2-thienyl)acetate

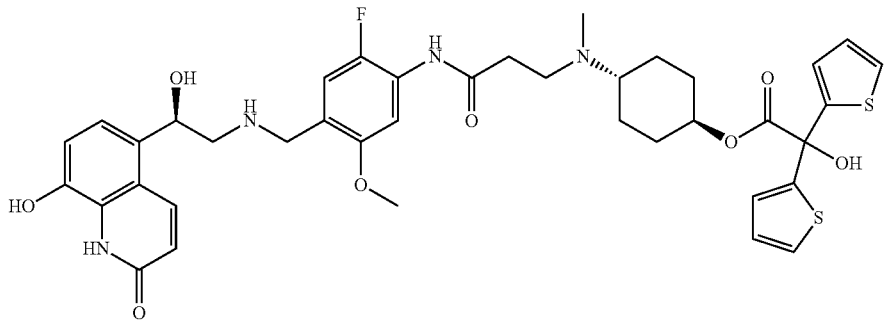 [SMILES: COc1cc(NC(=O)CCN(C)[C@H]2CC[C@H](OC(=O)C(O)(c3cccs3)c3cccs3)CC2)c(F)cc1CNC[C@H](O)c1ccc(O)c2[nH]c(=O)ccc12]

Obtained as a white solid (52%) from trans-4-[(3-{[4-({[(2R)-2-{[tert-butyl(dimethyl)silyl]oxy}-2-(8-hydroxy-2-oxo-1,2-dihydroquinolin-5-yl)ethyl]amino}-methyl)-2-fluoro-5-methoxyphenyl]amino}-3-oxopropyl)(methyl)amino]cyclohexyl hydroxy(di-2-thienyl)acetate (intermediate 97; 350 mg, 0.39 mmol) and triethylamine trihydrofluoride (568 mg, 3.53 mmol) following the experimental procedure as described in Example 1, followed by a purification by preparative reversed-phase HPLC (System 2).

LRMS (m/z): 779(M+1)$^+$.

$^1$H NMR (300 MHz, DMSO-d$_6$) □ ppm 1.40 (br. s., 4 H) 1.74 (br. s., 2 H) 1.93 (br. s., 2 H) 2.21 (s, 3 H) 2.44-2.50 (m, 1 H) 2.60-2.74 (br. s., 4 H) 3.62-3.68 (m, 5 H) 4.69 (br. s., 1 H) 5.01 (br. s., 1 H) 6.47 (d, J=9.89 Hz, 1 H) 6.89 (d, J=9.10 Hz, 1 H) 6.97 (dd, J=5.08, 3.71 Hz, 2 H) 7.01-7.08 (c.s., 2 H) 7.14 (d, J=12.0 Hz, 1 H) 7.46 (d, J=6.02 Hz, 1 H) 7.73 (d, J=6.0 Hz, 1 H) 8.12 (d, J=9.00 Hz, 1 H) 10.46 (s, 1 H)

Intermediate 98

(4-amino-2-methoxyphenyl)methanol

Obtained as a brown oil (66%) from methyl 4-amino-2-methoxybenzoate (2 g, 11.04 mmol) and lithium aluminium hydride (22.08 mL, 22.08 mmol) following the experimental procedure as described in intermediate 38. The crude obtained was used in the next step without further purification.

LRMS (m/z): 154(M+1)$^+$.

Intermediate 99

[4-({[tert-butyl(dimethyl)silyl]oxy}methyl)-3-methoxyphenyl]amine

Obtained as an oil (70%) from (4-amino-2-methoxyphenyl)methanol (intermediate 98; 3.2 g, 21.35 mmol), dimethylaminopiridine (0.26 g, 2.13 mmol), triethylamine (5.9 mL, 42.7 mmol) and tert-butylchlorodimethylsilane (4.83 g, 32.05 mmol) following the experimental procedure as described in intermediate 92. The crude obtained was used in the next step without further purification.

LRMS (m/z): 268(M+1)$^+$.

Intermediate 100

N-[4-({[tert-butyl(dimethyl)silyl]oxy}methyl)-3-methoxyphenyl]acrylamide

Obtained as a solid (63%) from [4-({[tert-butyl(dimethyl)silyl]oxy}methyl)-3-methoxyphenyl]amine (intermediate 99; 5 g, 18.7 mmol), acryl oil chloride (1.08 mL, 24.28 mmol) and diethyldiisopropylamine (4.9 mL, 28.06 mmol) following the experimental procedure as described in intermediate 40. The crude obtained was purified by column chromatography with silica gel, eluting with methylene chloride.

LRMS (m/z): 322(M+1)$^+$.

Intermediate 101 trans-4-[(3-{[4-({[tert-butyl(dimethyl)silyl]oxy}methyl)-3-methoxyphenyl]amino}-3-oxopropyl)(methyl)amino]cyclohexyl hydroxy(di-2-thienyl)acetate Obtained as an oil (29%) from N-[4-({[tert-butyl(dimethyl)silyl]oxy}methyl)-3-methoxyphenyl]acrylamide (intermediate 100; 1.93 g, 0.01 mol) and trans-4-(methylamino)cyclohexyl hydroxy(di-2-thienyl)acetate (intermediate 5; 1.8 g, 0.01 mmol) following the experimental procedure as described in intermediate 80. The crude obtained was purified by column chromatography with silica gel, eluting with chloroform/methanol (50:1).

LRMS (m/z): 673(M+1)$^+$.

Intermediate 102 trans-4-[(3-{[4-(hydroxymethyl)-3-methoxyphenyl]amino}-3-oxopropyl)(methyl)-amino]cyclohexyl hydroxy(di-2-thienyl)acetate Obtained as a solid (52%) from trans-4-[(3-{[4-({[tert-butyl(dimethyl)silyl]oxy}methyl)-3-methoxyphenyl]amino}-3-oxopropyl)(methyl)amino]cyclohexyl hydroxy(di-2-thienyl)-acetate (intermediate 101; 1 g, 1.49 mmol) and hydrochloric acid 1M (4.46 mL, 4.46 mmol) following the experimental procedure as described in intermediate 42. The crude obtained was used in the next step without purification.

LRMS (m/z); 559(M+1)⁺.

Intermediate 103 trans-4-[{3-[(4-formyl-3-methoxyphenyl)amino]-3-oxopropyl}(methyl)amino]-cyclohexyl hydroxy(di-2-thienyl)acetate Obtained as a foam (72%) from trans-4-[(3-{[4-(hydroxymethyl)-3-methoxyphenyl]amino}-3-oxopropyl)(methyl)amino]cyclohexyl hydroxy(di-2-thienyl)acetate (intermediate 102; 0.4 g, 0.74 mol) and manganese (IV) oxide (0.6 g, 7.42 mol) following the experimental procedure as described in intermediate 102. The crude obtained was used in the next step without further purification.

LRMS (m/z): 557 (M+1)⁺.

Intermediate 104 trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-3-methoxyphenyl]amino}-3-oxopropyl)-(methyl)amino]cyclohexyl hydroxy(di-2-thienyl)acetate Obtained as a foam (76%) from trans-4-[(3-{[(4-formyl-3-methoxyphenyl)amino]-3-oxopropyl}(methyl)amino]cyclohexyl hydroxy(di-2-thienyl)acetate (intermediate 103; 300 mg, 0.54 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (225 mg, 0.67 mmol) and sodium triacetoxyborohydride (411 mg, 1.94 mmol) following the experimental procedure as described in intermediate 30. The crude obtained was used in the next step without further purification.

LRMS (m/z): 874(M+1)⁺.

Example 17 trans-4-[(3-{[4-({[(2R)-2-hydroxy-2-(8-hydroxy-2-oxo-1,2-dihydroquinolin-5-yl)ethyl]amino}methyl)-3-methoxyphenyl]amino}-3-oxopropyl)-(methyl)amino]cyclohexyl hydroxy(di-2-thienyl)acetate hydrofluoride (1:2)

Obtained as a solid (27%) from trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-3-methoxyphenyl]-amino}-3-oxopropyl)(methyl)amino]cyclohexyl hydroxy(di-2-thienyl)acetate (intermediate 104; 400 mg, 0.46 mmol) and triethylamine trihydrofluoride (0.29 mL, 1.84 mmol) following the experimental procedure as described in Example 1, followed by a maceration with acetonitrile.

LRMS (m/z): 761(M+1)⁺.

¹H NMR (300 MHz, DMSO-d₆) □ ppm 1.42 (br. s., 4 H) 1.76 (br. s., 2 H) 1.96 (br. s., 2 H) 2.24 (s, 3 H) 2.45-2.50 (m, 1 H) 2.59 (br. s., 2 H) 2.75 (br. s., 4 H) 3.61-3.80 (m, 5 H) 4.74 (br. s., 1 H) 5.11 (br. s., 1 H) 6.52 (d, J=9.89 Hz, 1 H) 6.90-6.98 (m, 2 H) 7.01 (dd, J=5.08, 3.71 Hz, 2 H) 7.07 (c.s.,3 H) 7.21 (m, 1 H) 7.30 (s, 2 H) 7.38 (s., 1H) 7.50 (s, 1 H) 8.13 (d, J=9.89 Hz, 1 H) 10.10 (s, 1 H)

Intermediate 105

Ethyl 4-amino-2,5-difluorobenzoate

To a solution of 4-amino-2,5-difluorobenzonitrile (6.21 g, 38.28 mmol) in dioxane (32.5 mL) was added sulphuric acid 73% (52.2 mL) and the resulting mixture was stirred at 80° C. for 4 days. The crude reaction was added into water (250 mL) and basified with sodium hydroxide 32% (220 mL) until basic pH. The mixture was washed with methylene chloride and the aqueous phase was neutralized and extracted with ethyl acetate. The resulting organic phase was washed with brine, dried and filtered. The solvent was removed under reduced pressure to give the title compound as a white solid (42%), which was used in the next step without further purification.

LRMS (m/z): 174(M+1)⁺.

Intermediate 106

Ethyl 4-amino-2,5-difluorobenzoate

Obtained as a white solid (92%) from ethyl 4-amino-2,5-difluorobenzoate (intermediate 105; 2.7 g, 15.18 mmol) and hydrogen chloride 1.25M in ethanol (52.2 mL, 113.7 mmol) following the experimental procedure as described in intermediate 37. The crude obtained was used in the next step without further manipulation.

LRMS (m/z): 202(M+1)⁺.

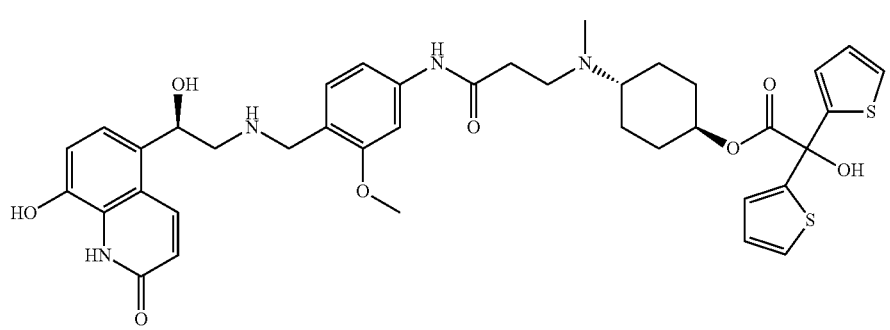 [SMILES: COc1cc(NC(=O)CCN(C)[C@H]2CC[C@H](OC(=O)C(O)(c3cccs3)c3cccs3)CC2)ccc1CNC[C@H](O)c1ccc(O)c2[nH]c(=O)ccc12]

Intermediate 107

(4-amino-2,5-difluorophenyl)methanol

Obtained as an orange solid (98%) from ethyl 4-amino-2,5-difluorobenzoate (intermediate 106; 2.89 g, 13.96 mmol) and lithium aluminium hydride (26.5 mL, 26.5 mmol) following the experimental procedure as described in intermediate 38. The crude obtained was used in the next step without further purification.

LRMS (m/z): 160(M+1)$^+$.

Intermediate 108

[4-({[tert-butyl(dimethyl)silyl]oxy}methyl)-2,5-difluorophenyl]amine

Obtained as a solid (85%) from (4-amino-2,5-difluorophenyl)methanol (intermediate 107; 2.48 g, 15.16 mmol), dimethylaminopiridine (0.18 g, 1.47 mmol), triethylamine (6.3 mL, 15.4 mmol) and tert-butylchlorodimethylsilane (4.5 g, 30.2 mmol) following the experimental procedure as described in intermediate 92, followed by a purification by column chromatography with silica gel, eluting with hexane/ethylacetate.

LRMS (m/z): 274(M+1)$^+$.

Intermediate 109

N-[4-({[tert-butyl(dimethyl)silyl]oxy}methyl)-2,5-difluorophenyl]acrylamide

Obtained as a solid (99%) from [4-({[tert-butyl(dimethyl)silyl]oxy}methyl)-2,5-difluorophenyl]amine (intermediate 108; 1 g, 3.49 mmol), acryloyl chloride (0.36 mL, 4.25 mmol) and diisopropylethylamino (0.92 mL, 5.25 mL) following the experimental procedure described in intermediate 40, followed by a purification by column chromatography with silica gel, eluting with hexene/ethylacetate.

LRMS (m/z): 328(M+1)$^+$.

Intermediate 110 trans-4-[(3-{[4-({[tert-butyl(dimethyl)silyl]oxy}methyl)-2,5-difluorophenyl]amino}-3-oxopropyl)(methyl)amino]cyclohexyl hydroxy(di-2-thienyl)acetate Obtained as a yellow oil (49%) from N-[4-({[tert-butyl(dimethyl)silyl]oxy}methyl)-2,5-difluorophenyl]acrylamide (intermediate 109; 0.51 g, 1,58 mmol) trans-4-(methyl-amino)cyclohexyl hydroxy(di-2-thienyl)acetate (intermediate 5, 0.5 g, 1.42 mmol) following the experimental procedure as described in intermediate 80, followed by a purification by column chromatography with silica gel, eluting with chloroform/hexane (15:1).

LRMS (m/z): 679(M+1)$^+$.

Intermediate 111 trans-4-[(3-{[2,5-difluoro-4-(hydroxymethyl)phenyl]amino}-3-oxopropyl)(methyl)-amino]cyclohexyl hydroxy(di-2-thienyl)acetate Obtained as a white solid (70%) from trans-4-[(3-{[4-({[tert-butyl(dimethyl)-silyl]oxy}methyl)-2,5-difluorophenyl]amino}-3-oxopropyl)(methyl)amino]-cyclohexyl hydroxy(di-2-thienyl)acetate (intermediate 110; 0.5 g, 0.75 mmol) and hydrochloric acid 1M (2.25 mL, 2.25 mol) following the experimental procedure as described in intermediate 42, followed by a purification by column chromatography with silica gel, eluting with chloroform/methanol (5:1).

LRMS (m/z): 565(M+1)$^+$.

Intermediate 112 trans-4-[{3-[(2,5-difluoro-4-formylphenyl)amino]-3-oxopropyl}(methyl)-amino]cyclohexyl hydroxy(di-2-thienyl)acetate Obtained as an oil (98%) from trans-4-[(3-{[2,5-difluoro-4-(hydroxymethyl)-phenyl]amino}-3-oxopropyl)(methyl)amino]cyclohexyl hydroxy(di-2-thienyl)acetate (intermediate 111; 0.28 g, 0.5 mmol) and manganese (IV) oxide (0.54 g, 5.32 mmol) following the experimental procedure as described in intermediate 43. The crude obtained was used in the next step without further manipulation.

LRMS (m/z): 563(M+1)$^+$.

Intermediate 113 trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-2,5-difluorophenyl]amino}-3-oxopropyl)(methyl)amino]cyclohexyl hydroxy(6-2-thienyl)acetate Obtained as an oil (71%) from trans-4-[{3-[(2,5-difluoro-4-formylphenyl)amino]-3-oxopropyl}(methyl)amino]cyclohexyl hydroxy(di-2-thienyl)acetate (intermediate 112; 0.28 g, 0.5 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (0.24 g, 0.63 mmol) and sodium triacetoxyborohydride (0.39 g, 1.78 mmol) following the experimental procedure as described in intermediate 30, followed by a purification by column chromatography with silica gel, eluting with chloroform/methanol (9:1).

LRMS (m/z): 882(M+1)$^+$.

Example 18 trans-4-[(3-{[2,5-difluoro-4-({[(2R)-2-hydroxy-2-(8-hydroxy-2-oxo-1,2-dihydroquinolin-5-yl)ethyl]amino}methyl)phenyl]amino}-3-oxopropyl)-(methyl)amino]cyclohexyl hydroxy(di-2-thienyl)acetate hydrofluoride (1:2)

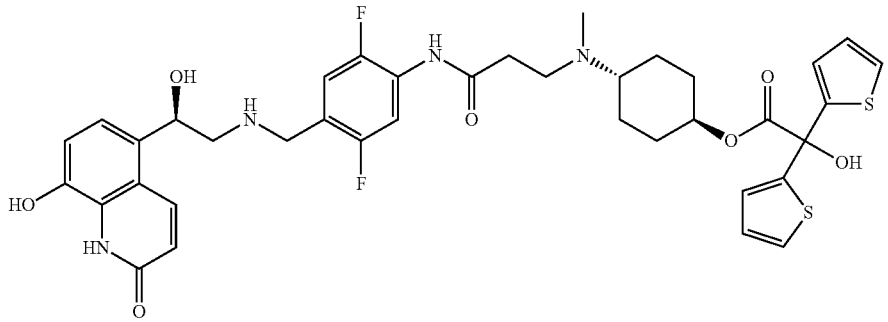 [SMILES: CN(CCC(=O)Nc1cc(F)c(CNC[C@H](O)c2ccc(O)c3[nH]c(=O)ccc23)cc1F)[C@H]1CC[C@H](OC(=O)C(O)(c2cccs2)c2cccs2)CC1]

Obtained as a white solid (88%) from trans-4-[(3-{[4-({[(2R)-2-{[tert-butyl(dimethyl)silyl]oxy}-2-(8-hydroxy-2-oxo-1,2-dihydroquinolin-5-yl)ethyl]amino}-methyl)-2,5-difluorophenyl]amino}-3-oxopropyl)(methyl)amino]cyclohexyl hydroxy(di-2-thienyl)acetate (intermediate 113; 0.3 g, 0.35 mmol) and triethylamine trihydrofluoride (0.25 mL, 1.52 mmol) following the experimental procedure as described in Example 1, without further manipulation.

LRMS (m/z): 767(M+1)$^+$.

$^1$H NMR (300 MHz, DMSO-d$_6$) □ ppm 1.41 (br. s., 4 H) 1.74 (br. s., 2 H) 1.95 (br. s., 2 H) 2.22 (s, 3 H) 2.45-2.50 (m, 1 H) 2.67-2.76 (c.s., 4 H) 3.74 (m, 2 H) 4.71 (br. s., 1 H) 5.06 (br. s., 1 H) 6.47 (d, J=9.95 Hz, 1 H) 6.88-6.93 (m, 2 H) 6.98 (dd, J=5.08, 371 Hz, 2 H) 7.06 (dd, J=3.71, 1.24 Hz, 2 H) 7.32 (m, 1 H) 7.46 (dd, J=5.08, 1.24 Hz, 2 H) 7.94 (m, 1 H) 8.14 (d, J=9.89 Hz, 1 H) 10.34 (s, 1 H) 10.73 (s, 1 H)

Intermediate 114

Ethyl 4-amino-3-fluorobenzoate

Obtained as a beige solid (97%) from 4-amino-3-flourobenzoic acid (0.9 g, 5.8 mmol) and hydrogen chloride 1.25M in ethanol (35 mL) following the experimental procedure as described in intermediate 37. The crude obtained was used in the next step without further manipulation.

LRMS (m/z): 184(M+1)$^+$.

Intermediate 115

(4-amino-3-fluorophenyl)methanol

Obtained as a light-yellow oil (90%) from ethyl 4-amino-3-fluorobenzoate (intermediate 114; 1 g, 5.62 mmol) and lithium aluminium hydride 1M in tetrahidrofuran (10.68 mL, 10.68 mmol) following the experimental procedure as described in intermediate 38. The crude obtained was used in the next step without further manipulation.

LRMS (m/z): 142(M+1)$^+$.

Intermediate 116

[4-({[tert-butyl(dimethyl)silyl]oxy}methyl)-2-fluorophenyl]amine

Obtained as a light-yellow oil (96%) from (4-amino-3-fluorophenyl)methanol (intermediate 115; 0.8 g, 5.72 mmol), dimethylaminopiridine (0.07 g, 0.57 mmol), triethylamine (2.39 mL, 17.17 mmol) and tert-butylchlorodimethylsilane (1.7 g, 11.4 mmol) following the experimental procedure as described in intermediate 92, followed by a purification by column chromatography with silica gel, eluting with hexane/ethylacetate (4:1).

LRMS (m/z): 256(M+1)$^+$.

Intermediate 117

N-[4-({[tert-butyl(dimethyl)silyl]oxy}methyl)-2-fluorophenyl]acrylamide

Obtained as a white solid (43%) from [4-({[tert-butyl(dimethyl)silyl]oxy}methyl)-2-fluorophenyl]amine (intermediate 116; 1.6 g, 6.52 mmol), acryloyl chloride (0.58 mL, 7.17 mmol) and diisopropylethylendiamine (1.7 mL, 9.77 mmol) following the experimental procedure as described in intermediate 40, followed by a purification by column chromatography with silica gel, eluting with hexane/ethylacetate (80:20).

LRMS (m/z): 310(M+1)$^+$.

Intermediate 118 trans-4-[(3-{[4-({[tert-butyl(dimethyl)silyl]oxy}methyl)-2-fluorophenyl]amino}-3-oxopropyl)(methyl)amino]cyclohexyl hydroxy(di-2-thienyl)acetate The title compound was obtained (44%) from N-[4-({[tert-butyl(dimethyl)-silyl]oxy}methyl)-2-fluorophenyl]acrylamide (intermediate 117; 0.5 g, 1.62 mmol), trans-4-(methylamino)cyclohexyl hydroxy(di-2-thienyl)acetate (intermediate 5, 0.51 g, 1.46 mmol) and sodium triacetoxyhydroborate (1.1 g, 5.24 mmol) following the experimental procedure as described in intermediate 30, followed by a purification by preparative reversed-phase HPLC (System 2).

LRMS (m/z): 661(M+1)$^+$.

Intermediate 119 trans-4-[(3-{[2-fluoro-4-(hydroxymethyl)phenyl]amino}-3-oxopropyl)(methyl)-amino]cyclohexyl hydroxy(di-2-thienyl)acetate Obtained as an oil (81%) from trans-4-[(3-{[4-({[tert-butyl(dimethyl)silyl]oxy}methyl)-2-fluorophenyl]amino}-3-oxopropyl)(methyl)amino]cyclohexyl hydroxy(di-2-thienyl)acetate (intermediate 118; 84 mg, 0.13 mmol) and hydrochloric acid 1M (0.38 mL, 0.38 mmol) following the experimental procedure as described in intermediate 42, followed by a purification by column chromatography with silica gel, eluting with Cl3CH to Cl3CH/MeOH 15:1.

LRMS (m/z): 310(M+1)$^+$.

Intermediate 120 trans-4-[{3-[(2-fluoro-4-formylphenyl)amino]-3-oxopropyl}(methyl)amino]-cyclohexyl hydroxy(di-2-thienyl)acetate 325 mg (0.59 mmol) of intermediate 119 are dissolved in 7.6 ml of Cl3CH and 546.8 mg (6.29 mmol) of activated MnO2 are added drop wise during 45 minutes under an argon atmosphere. The system is stirred 3 hr at 45° C. and is filtered, washed with Cl3CH and the filtrate concentrated in vacuo to give 290 mg (88% yield) of the pure title compound.

Intermediate 121 trans-4-[(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-fluorophenyl]amino}-3-oxo-propyl)-(methyl)amino]cyclohexyl hydroxy(di-2-thienyl)acetate The title compound was obtained (36%) from trans-4-[{3-[(2-fluoro-4-formylphenyl)amino]-3-oxopropyl}(methyl)amino]cyclohexyl hydroxy(di-2-thienyl)-acetate (0.29 g, 0.53 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (0.26 g, 0.67 mmol) and sodium triacetoxyhydroborate (0.4 g, 1.92 mmol) following the experimental procedure as described in intermediate 30, followed by a purification by preparative reversed-phase HPLC (System 2).

LRMS (m/z): 864(M+1)$^+$.

Example 19 trans-4-[(3-{[2-fluoro-4-({[(2R)-2-hydroxy-2-(8-hydroxy-2-oxo-1,2-dihydroquinolin-5-yl)ethyl]amino}methyl)phenyl]amino}-3-oxopropyl)(methyl)amino]cyclohexyl hydroxy(di-2-thienyl)acetate hydrofluoride (1:2)

Obtained as a white solid (88%) from trans-4-[(3-{[4-({[(2R)-2-{[tert-buty(dimethyl)silyl]oxy}-2-(8-hydroxy-2-oxo-1,2-dihydroquinolin-5-yl)ethyl]amino}-methyl)-2-fluorophenyl]amino}-3-oxopropyl)(methyl)amino]cyclohexyl hydroxy(di-2-thienyl)acetate (intermediate 121; 170 mg, 0.2 mmol) and triethylamine trihydrofluoride (137 mg, 0.55 mmol) following the experimental procedure as described in Example 1 without further manipulation.

LRMS (m/z): 749(M+1)$^+$.

1H NMR (300 MHz, DMSO-d$_6$) □ ppm 1.47 (br, s., 4 H) 1.81 (br. s., 2 H) 2.01 (br. s., 2 H) 2.29 (s, 3 H) 2.45-2.50 (m, 1 H) 2.57 (br. s., 2 H) 2.78 (br. s., 4 H) 3.83 (m, 2 H) 4.77 (br. s., 1 H) 5.15 (br. s., 1 H) 6.54 (d, J=9.89 Hz, 1 H) 6.94-7.00 (m, 2 H) 7.01-7.08 (m, 2 H) 7.09-7.19 (m 3H) 7.25-7.35 (m, 2 H) 7.53 (d, J=6.00 Hz, 1 H) 8.02 (m 1H) 8.18 (d, J=9.89 Hz, 1 H) 10.47 (s, 1 H)

Intermediate 122 trans-4-[[3-({2-chloro-5-methoxy-4-[(E)-2-methoxyvinyl]phenyl}amino)-3-oxo-propyl](methyl)amino]cyclohexyl hydroxy(di-2-thienyl)acetate To a suspension of (methoxymethyl) triphenylphosphonium chloride (0.83 g, 2.43 mmol) in anhydride tetrahidrofuran (4.3 mL) was added dropwise a solution of lithium bis(trimethylsilyl)amide 1M (2.43 mL, 2.43 mmol) at 0° C. under nitrogen atmosphere. The mixture was stirred for 30 minutes, then a solution of trans-4-((3-(2-chloro-4-formyl-5-methoxyphenylamino)-3-oxopropyl)(methyl)amino)cyclohexyl hydroxy(di-2-thienyl)acetate (intermediate 43; 0.41 g, 0.69 mmol) in anhydride tetrahidrofuran (2.1 mL) was added dropwise into the mixture. The reaction was stirred for 30 minutes at 0° C. and for 1.5 hours at room temperature. The crude was added into a saturated solution of ammonium chloride and extracted with ethyl acetate. The organic layer was washed with water, brine, dried and the solvent was removed under reduced pressure giving an orange solid. This crude was purified by column chromatography with silica gel, eluting with methylene chloride/isopropanol (93:7) to give the title compound as a white solid (56%).

LRMS (m/z): 620(M+1)$^+$.

Intermediate 123 trans-4-[(3-{[2-chloro-5-methoxy-4-(2-oxoethyl)phenyl]amino}-3-oxopropyl)-(methyl)amino]cyclohexyl hydroxy(di-2-thienyl)acetate To a solution of trans-4-[[3-({2-chloro-5-methoxy-4-[(E)-2-methoxyvinyl]phenyl}amino)-3-oxopropyl](methyl)

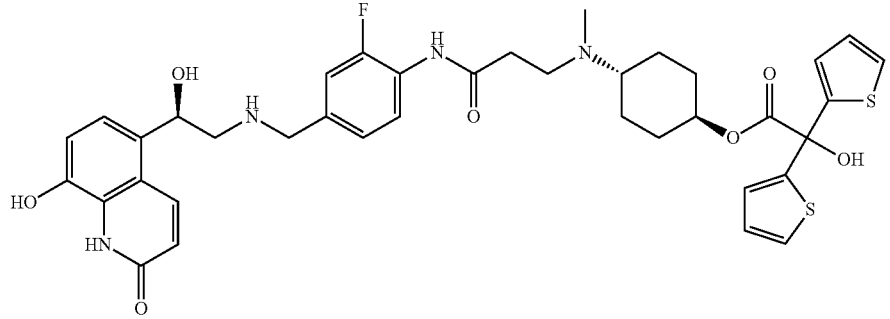 [SMILES: CN(CCC(=O)Nc1ccc(CNC[C@H](O)c2ccc(O)c3[nH]c(=O)ccc23)cc1F)[C@H]1CC[C@H](OC(=O)C(O)(c2cccs2)c2cccs2)CC1]

amino]cyclohexyl hydroxy(di-2-thienyl)acetate (intermediate 122: 0.36 g, 0.17 mmol) in anhydride tetrahidrofurane (0.5 mL) was added dropwise hydrochloric acid 2M (0.34 mL, 0.7 mmol). The mixture was stirred at 65° C. for 5 hours and a half. A mixture of water/ice was poured into the reaction and then extracted with ethyl acetate. The organic layer was washed with water and brine, dried and the solvent was removed under reduced pressure. The crude obtained was purified by column chromatography with silica gel, eluting with methylen chloride/methanol (95:5) to give the title compound as an oil (90%).

LRMS (m/z): 606(M+1)$^+$.

Intermediate 124 trans-4-[(3-{[4-(2-{[(2R)-2-{[tert-butyl(dimethyl) silyl]oxy}-2-(8-hydroxy-2-oxo-1,2-dihydroquinolin-5-yl)ethyl]amino}ethyl)-2-chloro-5-methoxyphenyl] amino}-3-oxopropyl(methyl)amino]cyclohexyl hydroxy(di-2-thienyl)acetate To a solution of trans-4-[(3-{[2-chloro-5-methoxy-4(2-oxoethyl)phenyl]amino}-3-oxopropyl)(methyl)amino]cyclohexyl hydroxy(di-2-thienyl)acetate (intermediate 123; 173 mg, 0.16 mmol) in methanol (1.73 mL) was added (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (78 mg, 0.2 mmol), diisopropylethylendiamine (0.03 mL, 0.2 mmol) and sodium triacetoxyborohydride (108 mg, 0.51 mmol). The reaction mixture was stirred for 2.5 hours at room temperature. At 0° C. the mixture was added into a 20 mL of bicarbonate 4%, then the crude was extracted with ethyl acetate, washed with water and brine, dried and the solvent was removed under reduced pressure. The crude obtained was purified by column chromatography with silica gel, eluting with methylen chloride/methanol (9;1) to give the title compound as a yellow solid (52%).

LRMS (m/z): 924(M+1)$^+$.

Example 20 trans-4-[(3-{[2-chloro-4-(2-{[(2R)-2-hydroxy-2-(8-hydroxy-2-oxo-1,2-dihydroquinolin-5-yl)ethyl] amino}ethyl)-5-methoxyphenyl]amino}-3-oxopropyl)-(methyl)amino]cyclohexyl hydroxy(di-2-thienyl)acetate hydrofluoride (1:2)

Obtained as a white solid (79%) from trans-4-[(3-{[4-(2-{[(2R)-2-{[tert-butyl(dimethyl)silyl]oxy}-2-(8-hydroxy-2-oxo-1,2-dihydroquinolin-5-yl)ethyl]amino}ethyl)-2-chloro-5-methoxyphenyl]amino}-3-oxopropyl)(methyl)amino] cyclohexyl hydroxy(di-2-thienyl)acetate (intermediate 124; 70 mg, 0.08 mmol) and triethylamine trihydrofluoride (0.049 mL, 0.3 mmol) following the experimental procedure as described in Example 1, followed by a maceration with acetonitrile.

LRMS (m/z): 809(M+1)$^+$.

1H NMR (300 MHz, DMSO-d6) ☐ ppm 1.34 (br.s. 4H) 1.70 (b.s. 2H) 1.88 (b.s. 2H) 2.20 (s. 3H) 2.51 (m 1H) 2.67 (br.s. 2H) 2.78 (br.s. 2H) 3.26 (c.s. 3H) 3.67 (s 3H) 4.63 (m.1H) 5.08 (br.s. 1H) 6.45 (d, J=9.89 Hz, 1 H) 6.84-6.95 (m, 3 H) 7.01-7.08 (m, 2 H) 6.99-7.07 (m 3H) 7.16-7.23 (m, 2 H) 7.40 (d, J=6.00 Hz, 1 H) 7.71 (s 1H) 8.12 (d, J=9.89 Hz, 1 H) 10.60 (s, 1 H)

Intermediate 125 trans-4-[(3-{2-chloro-5-methoxy-4-[(E)-2-methoxyvinyl]phenoxy}propyl)(methyl)-amino] cyclohexyl hydroxy(di-2-thienyl)acetate The title compound was obtained (59%) from trans-4-[[3.(2-chloro-4-formyl-5-methoxyphenoxy)propyl](methyl) amino]cyclohexyl hydroxy(di-2-thienyl)acetate (intermediate 57; 282 mg, 0.48 mmol), (methoxymethyl) triphenylphosphonium chloride (423 mg, 1.2 mmol) and lithium bis(trimethylsilyl)amide 1M (1.2 mL, 1.2 mmol) following the experimental procedure as described in intermediate 122, followed by a purification by column chromatography with silica gel, eluting with ether/methanol (9:1).

LRMS (m/z): 607(M+1)$^+$.

Intermediate 126 trans-4-[{3-[2-chloro-5-methoxy-4-(2-oxoethyl)phenoxy]propyl}(methyl)amino]-cyclohexyl hydroxy (di-2-thienyl)acetate The title compound was obtained (81%) from trans-4-[(3-{2-chloro-5-methoxy-4-[(E)-2-methoxyvinyl] phenoxy}propyl)(methyl)amino]cyclohexyl hydroxy(di-2-

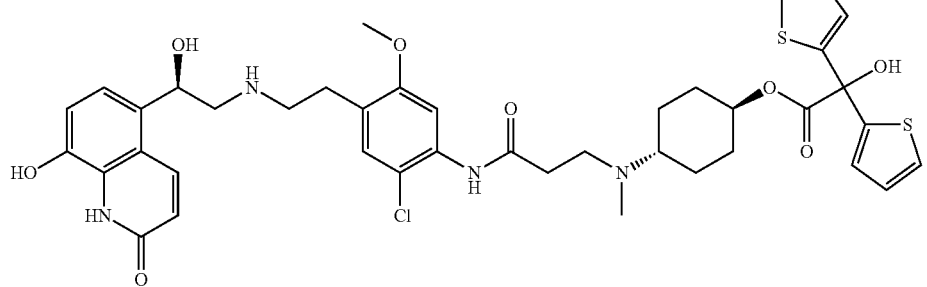

thienyl)acetate (intermediate 125; 193 mg, 0.28 mmol) and hydrochloric acid 2N (0.42 mL, 0.84 mmol) following the experimental procedure as described in intermediate 123, followed by a purification by column chromatography with silica gel, eluting with methylen chloride/methanol (95:5).

LRMS (m/z): 593(M+1)$^+$.

Intermediate 127 trans-4-[{3-[4-(2-{[(2R)-2-{[tert-butyl(dimethyl)silyl]oxy}-2-(8-hydroxy-2-oxo-1,2-dihydroquinolin-5-yl)ethyl]amino}ethyl)-2-chloro-5-methoxyphenoxy]propyl}-(methyl)amino]cyclohexyl hydroxy(di-2-thienyl)acetate Obtained as an oil (40%) from trans-4-[{3-[2-chloro-5-methoxy-4-(2-oxoethyl)phenoxy]propyl}(methyl)amino]cyclohexyl hydroxy(di-2-thienyl)acetate (intermediate 126; 137 mg, 0.23 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (109 mg, 0.28 mmol), diisopropylethylendiamine (0.048 mL, 0.28 mmol) and sodium triacetoxyborohydride (103 mg, 0.46 mmol) following the experimental procedure as described in intermediate 124, followed by a purification by preparative reversed-phase HPLC (System 2).

LRMS (m/z); 911(M+1)$^+$.

Example 21 trans-4-[{3-[2-chloro-4-(2-{[(2R)-2-hydroxy-2-(8-hydroxy-2-oxo-1,2-dihydroquinolin-5-yl)ethyl]amino}ethyl)-5-methoxyphenoxy]propyl}(methyl)-amino]cyclohexyl hydroxy(di-2-thienyl)acetate hydrofluoride (1:2)

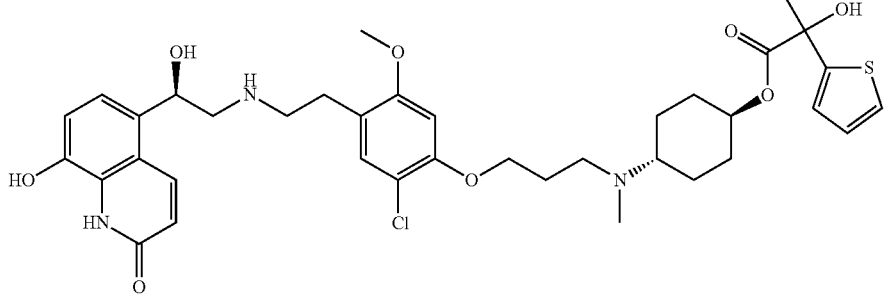

Obtained as a white solid (77%) from trans-4-[{3-[4-(2-{[(2R)-2-{[tert-butyl(dimethyl)silyl]oxy}-2-(8-hydroxy-2-oxo-1,2-dihydroquinolin-5-yl)ethyl]amino}ethyl)-2-chloro-5-methoxyphenoxy]propyl}(methyl)amino]cyclohexyl hydroxy(di-2-thienyl)-acetate (intermediate 127; 83 mg, 0.09 mmol) and triethylamine trihydrofluoride (0.06 mL, 0.4 mmol) following the experimental procedure as described in Example 1, followed by a maceration wilt acetonitrile.

LRMS (m/z): 796(M+1)$^+$.

1H NMR (300 MHz, DMSO-d6) □ ppm 1.41 (m., 4H) 1.76 (br. s., 2 H) 1.87 (br. s., 2 H) 1.94 (br. s., 2 H) 2.23 (s, 3 H) 2.44 (br. s., 2 H) 2.50 (br. s., 1 H) 2.61 (m., 2 H) 2.78 (br. s., 3 H) 2.92 (br.s., 4H) 3.84 (s., 3 H) 4.13 (br. s., 2 H) 4.72 (br. s., 1 H) 5.23 (br. s., 1 H) 6.56 (d, J=9.89 Hz, 1 H) 6.77 (s., 1 H) 6.94-7.04 (m, 3 H) 7.10-7.17 (m, 3 H) 7.22 (s., 1 H) 7.31 (br.s., 1 H) 7.50 (d, J=9.89 Hz, 1 H) 8.24 (s, 1 H)

Intermediate 128 methyl 4-amino-5-iodo-2-methoxybenzoate

To a solution of methyl 4-amino-2-methoxybenzoate (13 g, 0.07 mol) in acetic acid (300 mL) was added dropwise a solution of iodine monochloride (11.5 g, 0.07 mol) in acetic acid (50 mL). The mixture was stirred for 1.5 hours at room temperature. The precipitate was filtered and washed with ether. Then was dissolved with bicarbonate 4% and extracted with ethyl acetate. The organic layer was washed with brine, dried and the solvent was removed under reduced pressure giving the title compound as a white solid (88%), which was used in the next step without further purification.

LRMS (m/z): 308(M+1)$^+$.

Intermediate 129 methyl 4-amino-5-cyano-2-methoxybenzoate

A solution of methyl 4-amino-5-iodo-2-methoxybenzoate (intermediate 128; 5 g, 16.28 mmol) and dicyanozinc (1.5 g, 12.77 mmol) in dimethylformamide (50 mL) in a slenck vessel was degasified with nitrogen. Then tetrakis (1 g, 0.87 mmol) was added and the reaction mixture was stirred at 80° C. for 2 hours. Water was added into the reaction mixture and the crude was extracted with ethyl acetate, the organic layer was washed with brine, dried and the solvent was removed under reduced pressure. The crude obtained was treated with methanol and ether to obtain the title compound as a yellow solid (76%).

LRMS (m/z): 207(M+1)$^+$.

Intermediate 130

2-amino-5-(hydroxymethyl)-4-methoxybenzonitrile

To a solution of methyl 4-amino-5-cyano-2-methoxybenzoate (intermediate 129; 0.59 g, 2.88 mmol) in tetrahydrofuran (40 mL) was added dropwise lithium tetrahydroborate 2M (21.7 mL, 43.4 mmol) at 0° C. under nitrogen atmosphere. After 5 minutes was added dropwise ethanol (7.5 mL). The mixture was stirred for five days at room temperature. Then the crude was poured into a saturated solution of ammonium chloride and ice, and stirred for 10 minutes. The crude was extracted with ethyl acetate and washed with water and brine, dried and the solvent was removed under reduced pressure to obtain the title compound as a white solid (81%).

LRMS (m/z): 179(M+1)$^+$.

Intermediate 131

2-amino-5-({[tert-butyl(dimethyl)silyl]oxy}methyl)-4-methoxybenzonitrile

Obtained as a white solid (79%) from 2-amino-5-(hydroxymethyl)-4-methoxybenzonitrile (intermediate 130; 0.44 g, 2.35 mmol), tert-butylchlorodimethylsilane (0.71 g, 4.71 mmol) and imidazole (0.48 g, 7.05 mmol) following the experimental procedure as described in intermediate 39. The crude obtained was used in the next step without further manipulation.

LRMS (m/z): 293(M+1)$^+$.

Intermediate 132

5-({[tert-butyl(dimethyl)silyl]oxy}methyl)-2-isocyanato-4-methoxybenzonitrile Obtained as a yellow solid (56%) from 2-amino-5-({[tert-butyl(dimethyl)silyl]oxy}methyl)-4-methoxybenzonitrile (intermediate 131; 0.64 g, 1.87 mmol), trifosgene (0.21 g, 0.69 mmol) and triethylamine (0.52 mL, 3.73 mmol) following the experimental procedure as described in intermediate 59. The crude obtained was used in the next step without further manipulation.

LRMS (m/z): 319(M+1)$^+$.

Intermediate 133 trans-4-[{2-[({[4-({[tert-butyl(dimethyl)silyl]oxy}methyl)-2-cyano-5-methoxy-phenyl]amino}carbonyl)oxy]ethyl}(methyl)amino]cyclohexyl hydroxy(di-2-thienyl)acetate Obtained as a yellow solid (14%) from 5-({[tert-butyl(dimethyl)silyl]oxy}methyl)-2-isocyanato-4-methoxybenzonitrile (intermediate 132; 0.48 g, 1.51 mmol), trans-4-(methylamino)cyclohexyl hydroxy(di-2-thienyl)acetate (intermediate 5, 0.44 g, 1.13 mmol) and diisopropylethylendiamine (0.6 mL, 3.44 mmol) following the experimental procedure as described in intermediate 61, followed by a purification by column chromatography with silica gel, eluting with methylen chloride/isopropanol (9:1).

LRMS (m/z): 714(M+1)$^+$.

Intermediate 134 trans-4-[{2-[({[2-cyano-4-(hydroxymethyl)-5-methoxyphenyl]amino}carbonyl)-oxy]ethyl}(methyl)amino]cyclohexyl hydroxy(di-2-thienyl)acetate Obtained foam (72%) from trans-4-[{2-[({[4-({[tert-butyl(dimethyl)silyl]oxy}methyl)-2-cyano-5-methoxyphenyl]amino}carbonyl)oxy]ethyl}(methyl)amino]cyclohexyl hydroxy-(di-2-thienyl)acetate (intermediate 133; 155 mg; 0.17 mmol) and hydrochloric acid 1M (0.65 mL, 0.65 mmol) following the experimental procedure as described in intermediate 42, followed by a purification by column chromatography with silica gel, eluting with methylen chloride/isopropanol (9:1).

LRMS (m/z): 600(M+1)$^+$.

Intermediate 135 trans-4-[[2-({[(2-cyano-4-formyl-5-methoxyphenyl)amino]carbonyl}oxy)ethyl]-(methyl)amino]cyclohexyl hydroxy(di-2-thienyl)acetate Obtained as a yellow foam (94%) from trans-4-[{2-[({[2-cyano-4-(hydroxymethyl)-5-methoxyphenyl]amino}carbonyl)oxy]ethyl}(methyl)amino]cyclohexyl hydroxy(di-2-thienyl)acetate (intermediate 134: 68 mg, 0.11 mmol) and manganese (IV) oxide (106 mg, 1.22 mmol) following the experimental procedure as described in intermediate 43. The crude obtained was used in the next step without further manipulation.

LRMS (m/z): 598(M+1)$^+$.

Intermediate 136 trans-4-[{2-[({[4-({[(2R)-2-{[tert-butyl(dimethyl)silyl]oxy}-2-(8-hydroxy-2-oxo-1,2-dihydroquinolin-5-yl)ethyl]amino}methyl)-2-cyano-5-methoxyphenyl]amino}-carbonyl)oxy]ethyl}(methyl)amino]cyclohexyl hydroxy(di-2-thienyl)acetate Obtained as a foam (77%) from trans-4-[[2-({[(2-cyano-4-formyl-5-methoxyphenyl)amino]carbonyl}oxy)ethyl](methyl)amino]cyclohexyl hydroxy(di-2-thienyl)acetate (intermediate 135; 62 mg, 0.1 mmol), (2R)-2-{[tert-butyl-(dimethyl)silyl]oxy}-2-(8-hydroxy-2-oxo-1,2-dihydroquinolin-5-yl)ethanaminium acetate (prepared according to preparation 8 from US20060035931) (50 mg, 0.13 mmol), diisopropylethylendiamine (0.02 mL, 0.14 mmol) and triacetoxiborohydride (70 mg, 0.33 mmol) following the experimental procedure as described in intermediate 135. The crude obtained was used in the next step without further manipulation.

LRMS (m/z): 917(M+1)$^+$.

Example 22 trans-4-[{2-[({[2-cyano-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)amino]cyclohexyl hydroxy(di-2-thienyl)acetate hydrofluoride (1:2)

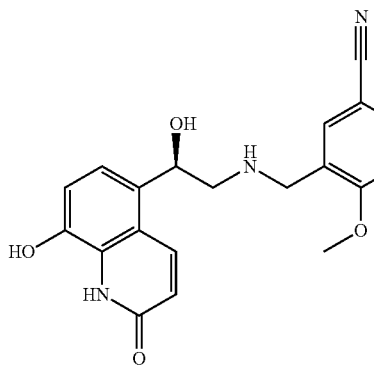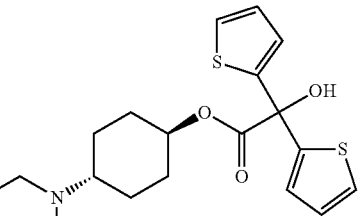

Obtained as a white solid (79%) from trans-4-[{2-[({[4-({[(2R)-2-{[tert-butyl(dimethyl)silyl]oxy}-2-(8-hydroxy-2-oxo-1,2-dihydroquinolin-5-yl)ethyl]amino}-methyl)-2-cyano-5-methoxyphenyl]amino}carbonyl)oxy]ethyl}(methyl)amino]cyclohexyl hydroxy(di-2-thienyl)acetate (intermediate 136; 75 mg, 0.08 mmol) and triethylamine trihydrofluoride (0.05 mL, 0.31 mmol) following the experimental procedure as described in Example 1, followed by a maceration with acetonitrile.

LRMS (m/z): 802(M+1)$^+$.

$^1$H NMR (300 MHz, DMSO-d6) ☐ ppm 1.37 (br.s., 4H); 1.73 (m., 2H); 1.91 (m., 2H); 2.22 (s., 3H); 2.43 (b.s., 1H); 2.66 (m., 2H); 2.73 (m., 2H); 3.76 (m., 2H); 3.81 (s., 3H); 4.12 (m., 2H); 4.69 (b.s., 1H); 5.10 (m., 1H); 6.50 (d., J=12 Hz, 1H); 6.89-7.01 (m., 3H); 7.06 (m., 3H); 7.13 (s., 1H); 7.25 (b.s., 1H); 7.46 (d., J=6 Hz; 1H); 7.68 (s., 1H); 8.13 (d., J=12 Hz, 1H); 9.71 (s., 1H); 10.37 (b.s., 1H).

Intermediate 137

4-amino-2,5-difluorobenzoic acid

To a solution of 4-amino-2,5-difluorobenzonitrile (6.21 g, 38.28 mmol) in dioxane (32.5 mL) was added 52.2 mL of sulphuric acid 73% p/p. The reaction mixture was stirred at 80° C. for 96 hours. The crude was poured into 250 mL of water and basified by sodium hydroxide 32% until basic pH and washed with methylen chloride. The aquoes phase was neutralized with hydrochloric acid 5N and the crude was extracted with ethyl acetate, washed with brine, dried and the solvent was removed under reduced pressure to give the title compound as a white solid (42%), which was used in the next step without further purification.

LRMS (m/z): 174(M+1)$^+$.

Intermediate 138 ethyl 4-amino-2,5-difluorobenzoate

A solution of 4-amino-2,5-difluorobenzoic acid (intermediate 137; 2.7 g; 0.015 mol) in hydrogen chloride 1.25 in ethanol (91 mL, 0.113 mol) was stirred for 24 hours at 60° C. The solvent was removed under reduced pressure and the crude obtained was treated with water and solid bicarbonate to obtain a basic pH, after few minutes stirring an extraction with ethyl acetate was done. The organic layer was washed with brine, dried and the solvent was removed under reduced pressure to give the title compound as a white solid (92%), which was used in the next step without further purification.

LRMS (m/z): 202(M+1)$^+$.

Intermediate 139

(4-amino-2,5-difluorophenyl)methanol

Obtained as an orange solid (98%) from ethyl 4-amino-2,5-difluorobenzoate (intermediate 138; 2.89 g, 0.013 mol) and lithium aluminum hydride (26.5 mL, 0.02 mol) following the experimental procedure as described in intermediate 38. The crude obtained was used in the next step without further manipulation.

LRMS (m/z): 160(M+1)$^+$.

Intermediate 140

[4-({[tert-butyl(dimethyl)silyl]oxy}methyl)-2,5-difluorophenyl]amine

Obtained as a solid (85%) from (4-amino-2,5-difluorophenyl)methanol (intermediate 139; 2.48 g, 0.01 mol), dimethylaminopiridine (0.18 g, 0.001 mmol), triethylamine (6.3 mL, 0.04 mmol) and tert-butylchlorodimethylsilane (4.56 g, 0.03 mmol) following the experimental procedure as described in intermediate 92, followed by a purification by column chromatography with silica gel, eluting with hexane/ethyl acetate.

LRMS (m/z): 274(M+1)$^+$.

Intermediate 141 tert-butyl[(2,5-difluoro-4-isocyanatobenzyl)oxy]dimethylsilane

Obtained as an oil (99%) from [4-({[tert-butyl(dimethyl)silyl]oxy}methyl)-2,5-difluorophenyl]amine (intermediate 140; 0.4 g, 1.46 mmol), triphosgene (0.15 g, 0.53 mmol) and

Intermediate 142 trans-4-[{2-[({[4-({[tert-butyl(dimethyl)silyl]oxy}methyl)-2,5-difluorophenyl]-amino}carbonyl)oxy]ethyl}(methyl)amino]cyclohexyl hydroxy(di-2-thienyl)-acetate Obtained as a colorless oil (41%) from tert-butyl[(2,5-difluoro-4-isocyanatobenzyl)oxy]dimethylsilane (intermediate 141; 0.43 g, 1.46 mmol), trans-4-[(2-hydroxyethyl)(methyl)amino]cyclohexylhydroxy(di-2-thienyl)acetate (intermediate 60; 0.57 g, 1.46 mmol) and diisopropylethylendiamine (0.38 mL, 2.22 mmol) following the experimental procedure as described in intermediate 61 (reaction time and temperature: 24 hours at 60° C.), followed by a purification by column chromatography with silica gel, eluting with methylene chloride/ethanol (9:1).

LRMS (m/z): 695(M+1)+.

Intermediate 143 trans-4-[{2-[({[2,5-difluoro-4-(hydroxymethyl)phenyl]amino}carbonyl)oxy]-ethyl}(methyl)amino]cyclohexyl hydroxy(di-2-thienyl)acetate Obtained as a white solid (98%) from trans-4-[{2-[({[4-({[tert-butyl(dimethyl)silyl]-oxy}methyl)-2,5-difluorophenyl]amino}carbonyl)oxy]ethyl}(methyl)amino]cyclohexyl hydroxy(di-2-thienyl)acetate (intermediate 142; 0.42 g, 0.61 mmol) and hydrochloric acid 1M (1.83 mL, 1.83 mmol) following the experimental procedure as described in intermediate 42, followed by a purification by column chromatography with silica gel, eluting with methylene chloride/ethanol (9:1).

LRMS (m/z): 581(M+1)+.

Intermediate 144 trans-4-[[2-({[(2,5-difluoro-4-formylphenyl)amino]carbonyl}oxy)ethyl](methyl)-amino]cyclohexyl hydroxy(di-2-thienyl)acetate Obtained as a colorless oil (87%) from trans-4-[{2-[({[2,5-difluoro-4-(hydroxymethyl)phenyl]amino}carbonyl)oxy]ethyl}(methyl)amino]cyclohexyl hydroxy(di-2-thienyl)acetate (intermediate 143; 0.35 g, 0.6 mmol) and manganese (IV) oxide (0.57 g, 6.6 mmol) following the experimental procedure as described in intermediate 43. The crude obtained was used in the next step without further manipulation.

LRMS 579(M+1)+.

Intermediate 145 trans-4-[{2-[({[4-({[(2R)-2-{[tert-butyl(dimethyl)silyl]oxy}-2-(8-hydroxy-2-oxo-1,2-dihydroquinolin-5-yl)ethyl]amino}methyl)-2,5-difluorophenyl]amino}carbonyl)-oxy]ethyl}(methyl)amino]cyclohexyl hydroxy(di-2-thienyl)acetate Obtained as a colorless oil (63%) from trans-4-[[2-({[(2,5-difluoro-4-formyl-phenyl)amino]carbonyl}oxy)ethyl](methyl)amino]cyclohexyl hydroxy(di-2-thienyl)-acetate (intermediate 144; 0.3 g, 0.52 mmol), (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) (0.24 g, 0.62 mmol), diisopropylethylendiamine (0.1 mL, 0.62 mmol) and sodium triacetoxyborohydride (0.23 g, 1.04 mmol) following the experimental procedure as described in intermediate 124, followed by a purification by preparative reversed-phase HPLC (System 2).

LRMS (m/z): 898(M+1)+.

Example 23 trans-4-[{2-[({[2,5-difluoro-4-({[(2R)-2-hydroxy-2-(8-hydroxy-2-oxo-1,2-dihydroquinolin-5-yl)ethyl]amino}methyl)phenyl]amino}carbonyl)oxy]ethyl}(methyl)-amino]cyclohexyl hydroxy(di-2-thienyl)acetate hydrofluoride (1:2)

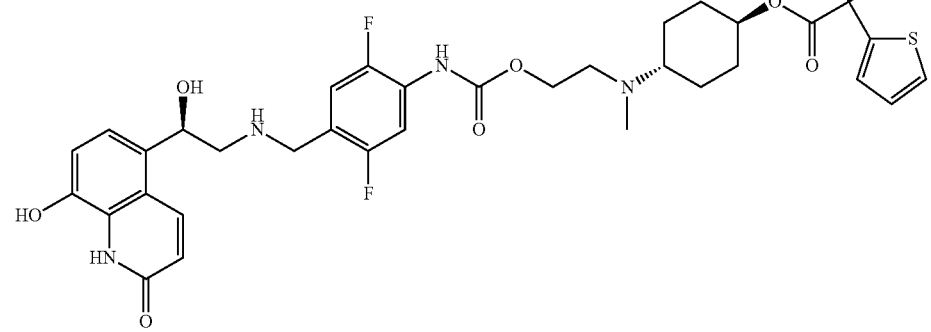

Obtained as a white solid (81%) from trans-4-[{2-[({[4-({[(2R)-2-{[tert-butyl(dimethyl)silyl]oxy}-2-(8-hydroxy-2-oxo-1,2-dihydroquinolin-5-yl)ethyl]amino}-methyl)-2,5-difluorophenyl]amino}carbonyl)oxy]ethyl}(methyl)amino]cyclohexyl hydroxy-(di-2-thienyl)acetate (intermediate 145; 0.29 g, 0.32 mmol) and triethylamine trihydrofluoride (0.22 mL, 1.39 mmol) following the experimental procedure as described in Example 1. The crude obtained was macerated with acetonitrile to afford the title compound.

LRMS (m/z): 783(M+1)+.

$^1$H NMR (300 MHz, DMSO-d$_6$) □ ppm 1.37 (m., 4H); 1.71 (m., 2H); 1.92 (m., 2H); 2.21 (s., 3H); 2.42 (b.s., 1H); 2.66 (m., 4H); 3.72 (m., 2H); 4.11 (m., 2H); 4.69 (b.s., 1H); 5.05 (m., 1H); 6.47 (d., J=12 Hz, 1H); 6.88-6.93 (m., 1H); 6.97 (m., 2H); 7.09 (m., 3H); 7.25 (m., 2H); 7.46 (d., J=6 Hz; 2H); 8.14 (d., J=12 Hz, 1H); 9.50 (s., 1H); 10.35 (b.s., 1H).

Intermediate 146

2,2-dimethylbut-3-enoic acid 2.11 ml (20.31 mmol) of diethylamine were dissolved in 9 ml of THF in a Schlenck vessel. After cooling to −78° C. 8.60 ml (21.5 mmol) of n-Butyllithium were added. The solution was stirred at 0° C. for 15 minutes. The system was cooled again to −78° C. and a solution of 1.0 g (9.69 mmol) of (E)-2-methylbut-2-enoic acid in 9 ml THF was dropped. The yellow solution was stirred 30 minutes at 0° C. and cooled once more to −78° C. 0.92 ml of dimethyl sulphate in 22 ml of THF were dropped slowly. The system was stirred at −78° C. for 30 minutes and 1 hour at room temperature. Excess water was then added and washed thrice with diethyl ether. The aqueous layer was acidified at 0° C. with concentrated hydrochloric acid and extracted thrice with ethyl acetate. The organic phase was washed with brine, dried and concentrated to give a compound pure enough to follow with the synthesis.

Intermediate 147

N-[4-({[tert-butyl(dimethyl)silyl]oxy}methyl)-2-chloro-5-methoxyphenyl]-2,2-dimethylbut-3-enamide 0.87 g (7.62 mmol) of 2,2-dimethylbut-3-enoic acid were dissolved in 1.79 ml (24.51 mmol) of thienyl chloride and the system is stirred 4 hr at 100° C. The excess thienyl chloride was evaporated and the residue is dissolved in 28 ml THF and slowly added at −20° C. to a solution of the intermediate 39 (2.1 g; 6.12 mmol) and 1.71 ml (12.27 mmol) of triethylamine in 32 ml THF. The system is stirred 20 minutes at −20° C. and at room temperature overnight. The crude was poured into 75 ml of a 4% solution of sodium hydrogen carbonate and the compound was extracted with 75 ml of ethyl acetate, which was in turn washed with water, dried and concentrated giving 2.42 g of an oil (target compound with intermediate 39). After SP1 chromatographic purification (hexane to hexane ethyl acetate 8:2), 0.89 g of the pure title compound (37% yield) were obtained as a colorless oil.

Intermediate 148

N-[4-({[tert-butyl(dimethyl)silyl]oxy}methyl)-2-chloro-5-methoxyphenyl]-2,2-dimethyl-3-oxopropanamide 0.95 g (2.39 mmol) of intermediate 147 are dissolved in 19 ml THF. Under an argon atmosphere, 0.56 g (4.78 mmol) of N-methylmorpholine N-oxyde and 0.73 ml (0.18 mmol) of a 4% aqueous solution of OsO4 are added. The system is stirred at 30° C. overnight. 0.36 additional ml of OsO4 solution are added and the stirring is prosecuted for 6 hr. The solvents are removed in vacuo, the residue is suspended in 100 ml of water and is extracted with 100 ml of ethyl acetate. The organic phase is washed with brine, dried and concentrated. The residue (1.08 g of a brown solid corresponding to the intermediate diol) is suspended in 8.2 ml THF+1.3 ml of water. 0.77 g (3.59 mmol) of sodium periodate are added and the system is stirred at room temperature overnight. The solvents are removed in vacuo and the residue is suspended in 4% sodium hydrogen carbonate and extracted with 2×50 ml of ethyl acetate. The organic layer is washed with water, dried and concentrated to give 0.89 g of a dark oil (45% title compound and 55% of desilylated derivative) which is used per se in the next step.

Intermediate 149 trans-4-[(3-{[4-({[tert-butyl(dimethyl)silyl]oxy}methyl)-2-chloro-5-methoxyphenyl]-amino}-2,2-dimethyl-3-oxopropyl)(methyl)amino]cyclohexyl hydroxy(di-2-thienyl)acetate 0.63 g (1.58 mmol) of intermediate 148 are dissolved in 12.6 ml of THF. 0.69 g (1.96 mmol) of intermediate 5 and 0.225 ml of acetic acid are added and the system is stirred at 65° C. overnight. After cooling externally with an ice bath, 1.08 g (5.11 mmol) of sodium cyanoborohydride are added and the stirring prosecuted for 15 minutes at 5° C. and 45 minutes at room temperature. The solution is poured on 50 ml of 4% solution of sodium hydrogen carbonate and extracted with 3×30 ml of ethyl acetate. The organic phases are washed with sodium hydrogen carbonate solution and brine, dried and concentrated to give 1.0 g of a brown oil (complex mixture containing a 7% of title product and 6% of the corresponding desilylated derivative) used per se in the next synthetic step.

Intermediate 150 trans-4-[(3-{[2-chloro-4-(hydroxymethyl)-5-methoxyphenyl]amino}-2,2-dimethyl-3-oxopropyl)(methyl)amino]cyclohexyl hydroxy(di-2-thienyl)acetate 1.0 g of the complex mixture from intermediate 149 in 20.1 ml of THF is cooled to 5° C. while 0.707 ml of 1N aqueous hydrochloric acid is dropped in. The system is stirred at room temperature for 3 hr. After cooling again, 40 ml of water are added and the pH adjusted around 8 by adding solid NaHCO3. The mixture is extracted with 2×30 ml of ethyl acetate, washed with 4% sol of sodium hydrogen carbonate and brine, dried and concentrated. The residue (0.88 g of a dark oil containing a 11% of the title product) is purified through a SP1 cartridge eluting with CH2Cl2 to Cl2CH2/MeOH 95:5 to give 0.104 g of an off-white solid (HPLC purity is 67%).

Intermediate 151 trans-4-[{3-[(2-chloro-4-formyl-5-methoxyphenyl)amino]-2,2-dimethyl-3-oxo-propyl}(methyl)amino]cyclohexyl hydroxy(di-2-thienyl)acetate 104 mg of the intermediate 150 (67% purity) are dissolved in 2.08 ml of Cl3CH and 98 mg of activated MnO2 are added. The system is stirred overnight at 45° C. After filtering through a pad of diathomeus earth the filtrate is concentrated to give 101 mg of an orange oil (64% purity) used per se in the next step.

Intermediate 152 trans-4-[(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-2,2-dimethyl-3-oxopropyl)-(methyl)amino]cyclohexyl hydroxy(di-2-thienyl)acetate 101 mg of the intermediate 151 (64% purity) are dissolved in 1 ml of MeOH. 51 mg (0.13 mmol) of 5-((1R)-2-amino-1-{[tert-butyl(dimethyl)silyl]oxy}ethyl)-8-hydroxyquinolin-2(1H)-one acetate (prepared according to preparation 8 from US20060035931), 0.023 ml (0.13 mmol) of diisopropylethylamine and 72 mg (0.34 mmol) of sodium triacetoxyborohydride are added and the system stirred at room temperature for 2.5 hr. The crude is poured over 25 ml of 4% solution of NaHCO3 and extracted with 3×15 ml of ethyl acetate. The organic layer is washed with sol. 4% NaHCO3, brine, dried and concentrated to 147 mg of a solid. After chromatographic purification through SP1 system (Cl$_2$CH$_2$ to Cl$_2$CH$_2$/MeOH 9:1) 96 mg of title compound are obtained.

Example 24 trans-4-[(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-2,2-dimethyl-3-oxopropyl)-(methyl)amino]cyclohexyl hydroxy(di-2-thienyl)acetate

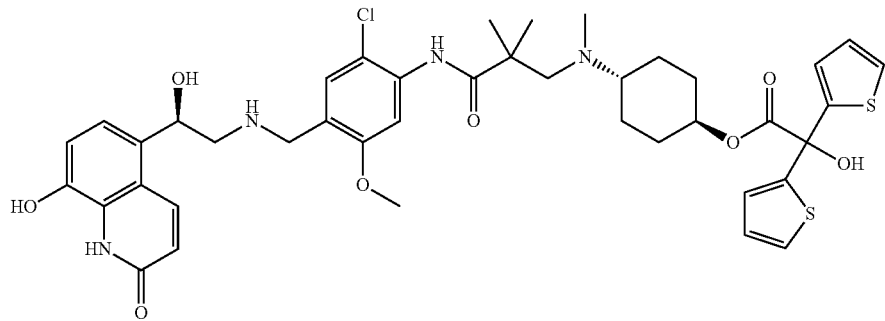 [SMILES: COc1cc(NC(=O)C(C)(C)CN(C)[C@H]2CC[C@H](OC(=O)C(O)(c3cccs3)c3cccs3)CC2)c(Cl)cc1CNC[C@H](O)c1ccc(O)c2[nH]c(=O)ccc12]

90 mg (0.08 mmol) of intermediate 152 (86% purity HPLC) are dissolved in 2.7 ml of THF. 0.054 ml (0.33 mmol) of Et$_3$N(HF)$_3$ are added and the system is stirred overnight at room temperature. The solvent is eliminated in vacuo and the residue is suspended in 20 ml of water: Solid NaHCO3 is added to saturation, 5 ml of Cl3CH added and the system is stirred for 1 hr. 20 additional ml of water and chloroform are added. The organic extracts are washed with brine, dried and concentrated. The crude product was purified by preparative reversed-phase HPLC (System 2) obtaining the title compound as a colourless solid (98% purity, 44% yield).

LRMS (m/z): 823(M+1)$^+$.

$^1$H NMR (300 MHz, DMSO-d$_6$) ☐ ppm 1.16 (s., 6H) 1.36 (br. s., 4 H) 1.76 (br. s., 2 H) 1.94 (br. s., 2 H) 2.27 (s, 3 H) 2.48-2.50 (m, 1 H) 2.59 (br. s., 2 H) 2.63-2.72 (br. s., 2 H) 3.58-3.64 (m, 5 H); 3.71 (s., 3H) 4.69 (br. s., 1 H) 5.02 (br. s., 1 H) 6.46 (d, J=9.89 Hz, 1 H) 6.86-6.90 (m, 2 H) 6.97 (dd, J=5.08, 3.71 Hz, 2 H) 7.06 (m., 2 H) 7.30 (s, 1 H) 7.46 (d., J=6 Hz, 2 H) 7.91 (s, 1 H) 8.13 (d, J=9.89 Hz, 1 H) 10.53 (s, 1 H)

Intermediate 153

5-chloro-4-hydroxy-2-methoxybenzoic acid methyl ester

To a suspension of 10 g (48 mmol) of 4-amino-5-chloro-2-methoxybenzoic acid in 50 ml H2O was added HBF4 (16.2 mL, 48% aqueous solution). The white cake was then cooled to 0° C. and NaNO2 (3.76 g in 30 mL of H2O) was added dropwise (addition funnel, 10 minutes). The suspension became bright yellow. It was stirred at that temperature for 30 minutes. The white precipitate was collected by filtration to isolate a diazonium salt (wet weight: 12.97 g). The diazonium salt was suspended in glacial AcOH (500 mL) and the resulting suspension was stirred at 100° C. for 1 hour (it became a brown solution). It was allowed to stand at RT for two additional hours. The solvent was removed under reduced pressure and the brown oily residue suspended in brine (500 mL) and extracted with EtOAC (3×300 mL). The combined organic layers were dried, filtered and evaporated under reduced pressure to give a brown oil which was treated with 0.5M NaOH in MeOH (150 mL) and stirred at RT for 90 min. It was stirred at RT for 3 hr. The solvent was evaporated and the residue redissolve in H2O (250 mL). The aqueous solution was acidified to pH=2 with 5N HCl and extracted with CH2Cl2 (3×250 mL). A solid precipitated which was filtered, washed with Et2O and dried in the oven (45° C., 90 min) to give 4.3 g of a dark-brown solid which was directly purified by column chromatography on a Merck column (80 g silica, Luer fitting) using the SP1 system with CH2Cl2 (A) and CH2Cl2/EtOAc 8:2(B) as eluents (0% to 25% B in 19 column volumes and 25% to 60% B in 10 CV, 100 mL/min). The appropriate fractions were collected and the solvent removed to afford 2.9 g (27% yield) of a pale red solid.

Intermediate 154

2-chloro-4-(hydroxymethyl)-5-methoxyphenol 1.1 g (5.08 mmol) of intermediate 153 are dissolved in 30 ml of THF. The solution is coded to 0° C. and 9.65 ml (9.65 mmol) of a 1M solution of LiAlh4 in THF are added drop wise. The system is stirred 10 minutes at 0° C. then 1 hr at rt. A 25% excess of hydride solution is added and the stirring prosecuted for 2 hr at rt and 30 minutes at 45° C. After cooling again to 0° C. 100 ml of saturated solution of sodium-potassium tartrate are slowly added. The compound is extracted with 2×200 ml of ethyl acetate which is dried and concentrated to give 930 mg of residue. Chromatographic purification (SP1 system eluting with Cl3CH to Cl3CH/MeOH 9:1) gives 459 mg (46% yield) of pure title compound.

Intermediate 155

[4-(4-bromobutoxy)-5-chloro-2-methoxyphenyl] methanol

A mixture of 391 mg (2.04 mmol) of intermediate 154, 1.48 ml (12.27 mmol) of 1,4-dibromobutane and 577 mg (4.09 mmol) of potassium carbonate in 9.2 ml of acetone in Ar atmosphere are heated to 75° C. in a microwave oven. After filtration the filtrate is concentrated and the residue purified chromatographically (SP1 system eluting with hexane to hexane/EtOAc 1:1) to give 264 mg (39% yield) of the title compound.

Intermediate 156 trans-4-[{4-[2-chloro-4-(hydroxymethyl)-5-methoxyphenoxy]butyl}(methyl)amino]-cyclohexyl hydroxy(di-2-thienyl)acetate A solution of 230 mg (0.71 mmol) of intermediate 155, 256 mg (0.71 mmol) of intermediate 5 and 0.19 ml (1.4 mmol) of triethylamine in 7 ml MeCN and 5 ml THF is heated to 70° C. for 24 hr. The solution is concentrated, 85 ml of Cl3CH and 40 ml water are added and the organic layer is washed with brine, dried and concentrated. The residue is chromatographically purified (SP1 system, Cl2CH2 to Cl2CH2/EtOH 9:1) to give 170 mg (43 pro yield) of the pure title compound.

Intermediate 157 trans-4-[[4-(2-chloro-4-formyl-5-methoxyphenoxy) butyl](methyl)amino]cyclohexyl hydroxy(di-2-thienyl)acetate 170 mg (0.29 mmol) of intermediate 156 are dissolved in 3.9 ml of chloroform. 321 mg (3.14 mmol) of activated MnO2 are added stepwise in 45 minutes and the system is stirred at 45° C. during 3 hr. After filtering the in organics and washing with 48 ml of Cl3CH the filtrate is concentrated to give 167 mg of title compound pure enough to be used in the next step.

Intermediate 158 trans-4-[{4-[4-({[(2R)-2-{[tert-butyl(dimethyl)silyl] oxy}-2-(8-hydroxy-2-oxo-1,2-dihydroquinolin-5-yl) ethyl]amino}methyl)-2-chloro-5-methoxyphenoxy] butyl}-(methyl)amino]cyclohexyl hydroxy(di-2-thienyl)acetate 163 mg (0.26 mmol) of intermediate 157, 125 mg (0.32 mmol) of 5-((1R)-2-amino-1-{[tert-butyl(dimethyl)silyl] oxy}ethyl)-8-hydroxyquinolin-2(1H)-one acetate (prepared according to preparation 8 from US20060035931) and 0.056 ml (0.32 mmol) of diisopropyl ethyl amine are dissolved in 1.3 ml of methanol. 117 mg (0.52 mmol) of sodium triacetoxyborohydride are added and the system is stirred at room temperature for 3.5 hr. The solvent is eliminated in vacuo and 16 ml of 4% NaHCO3 are added, The compound is extracted with 120 ml of ethyl acetate and the solution is dried and concentrated to give a residue which is purified by preparative reversed-phase HPLC (System 2) to give 173 mg of the title compound (71% yield).

Example 25 trans-4-[{4-[2-chloro-4-({[(2R)-2-hydroxy-2-(8-hydroxy-2-oxo-1,2-dihydroquinolin-5-yl)ethyl] amino}methyl)-5-methoxyphenoxy]butyl}(methyl) amino]cyclohexyl hydroxy(di-2-thienyl)acetate hydrofluoride (1:2)

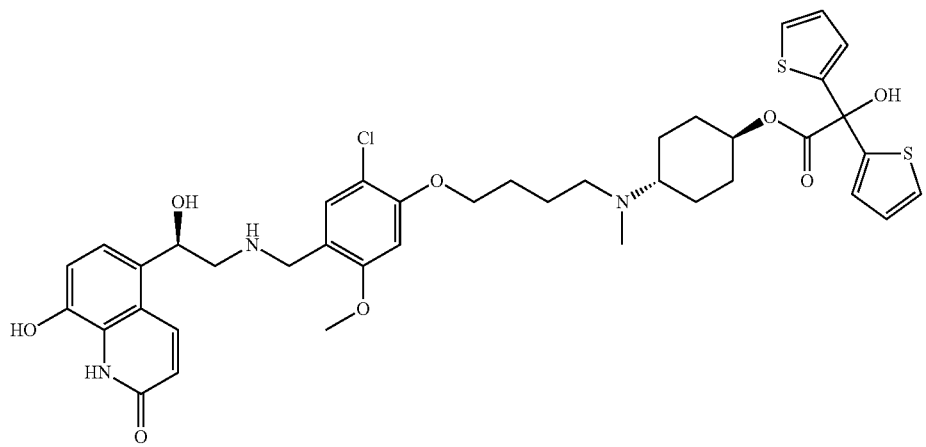 [SMILES: COc1cc(OCCCCN(C)[C@H]2CC[C@H](OC(=O)C(O)(c3cccs3)c3cccs3)CC2)c(Cl)cc1CNC[C@H](O)c1ccc(O)c2[nH]c(=O)ccc12]

170 mg (0.18 mmol) of the intermediate 158 are dissolved in 9 ml THF. 0.13 ml (0.80 mmol) of Et3N(HF)3 are added and the system stirred at rt overnight. The sod residue is decanted, treated with MeCN and filtered to give 136 mg of the title compound (88% yield).

LRMS (m/z): 796(M+1)$^+$.

$^1$H NMR (300 MHz, DMSO-d$_6$) ☐ ppm 1.44 (br. s., 4 H) 1.66 (br.s., 2 H) 1.80 (br.s, 4 H) 1.98 (br.s., 2 H) 2.30 (a, 3 H) 2.58-2.67 (m, 2 H) 2.80 (br. s., 2 H) 3.84 (s., 3 H) 4.15 (br. s., 2 H) 4.75 (br.s., 1H) 5.21 (br. s., 1 H) 6.53 (d, J=9.05 Hz, 1 H) 6.78 (s. 1H) 6.93-7.04 (m, 2 H) 7.11 (m., 3H) 7.31 (br.s., 1H) 7.41 (s., 1H) 7.51 (d, J=7.5 Hz, 2 H) 8.18 (d, J=9.05 Hz, 1 H)

Intermediate 159 trans-4-[{2-[({[4-({[(2R)-2-{[tert-butyl(dimethyl) silyl]oxy}-2-(5-hydroxy-3-oxo-3,4-dihydro-2H-1,4-benzoxazin-8-yl)ethyl]amino}methyl)-2-chloro-5-methoxyphenyl]-amino}carbonyl)oxy]ethyl} (methyl)amino]cyclohexyl hydroxy(di-2-thienyl)-acetate 100 mg (0.25 mmol) of 8-[(R)-2-amino-1-(tert-butyl-dimethyl-silanoxy)-ethyl-5-hydroxy-4H-benzo[1,4]oxazin-3-one (preparation described in WO2008149110 intermediate 65), 196 mg (0.26 mmol) of intermediate 62 and 0.045 ml (0.26 mmol) of diisopropyl ethyl amine are dissolved in 3 ml MeOH. 157 mg (0.75 mmol) of sodium triacetoxyborohydride are added and the system is stirred at rt during 2.5 hr. 50 mg (0.24 mmol) of sodium triacetoxyborohydride are added and the stirring prosecuted overnight. After three new additions of 50 mg of the hydride each followed by a subsequent stirring period of 2 hr the solvents are eliminated and the residue is treated with 20 ml of 4% sol of NaHCO3. The system is extracted thoroughly with ethyl acetate, which is dried and concentrated to give 220 mg of crude compound. After chromatographic purification (SP1 eluting with Cl3CH to Cl3CH/MeOH 9:1) 147 mg of title compound are obtained (59% yield).

Example 26 trans-4-[{2-[({[2-chloro-4-({[(2R)-2-hydroxy-2-(5-hydroxy-3-oxo-3,4-dihydro-2H-1,4-benzoxazin-8-yl) ethyl]amino}methyl)-5-methoxyphenyl] amino}carbonyl)-oxy]ethyl}(methyl)amino] cyclohexyl hydroxy(di-2-thienyl)acetate 140 mg (0.15 mmol) of intermediate 159 are dissolved in 6 ml THF. Under an argon atmosphere 0.15 ml (0.94 mmol) of Et$_3$N(HF)$_3$ are added and the system is stirred at rt for 18 hr and cooled externally with an acetone/dry ice bath. The supernatant is discarded and the oily residue is stirred 5 minutes with 8 ml THF, which is again discarded. The residue is treated with 8 ml MeCN for 10 minutes and the solid thus obtained is filtered, washed with a little MeCN and ethyl ether and dried in a vacuum dessicator at 40° C. for 2 hr, 68 mg (52% yield) of the pure title compound are obtained.

LRMS (m/z): 815(M+1)$^+$.

$^1$H NMR (300 MHz, DMSO-d$_6$) ☐ ppm 1.36 (m., 4H); 1.72 (m., 2H); 1.91 (m., 2H); 2.22 (s., 3H); 2.42 (b.s., 1H); 2.58 (m., 2H); 2.65 (m., 2H); 3.75 (m., 5H): 4.10 (m., 2H); 4.46 (s., 2H) 4.70 (b.s., 1H); 4.89 (b.s, 1H); 6.49 (d., J=6 Hz, 1H); 6.86 (d., J=6 Hz, 1H) 6.95-6.99 (m., 2H); 7.06 (m., 2H); 7.20 (s., 1H); 7.25 (b.s., 1H); 7.37 (s., 1H); 7.47 (d., J=6 Hz; 1H); 8.99 (s., 1H); 9.92 (b.s., 1H).

Intermediate 160

Methyl 9-methyl-9H-xanthene-9-carboxylate 3.25 g (13.53 mmol) of methyl 9H-xanthene-9-carboxylate are dissolved in 70 ml THF, the solution is cooled with an ice bath and 10.15 ml (20.29 mmol) of a 2M solution of LDA are added drop wise whilst keeping the temperature at 0° C. After stirring at room temperature for 1 hr, 1.68 ml (27.06 mmol) of iodomethane are added drop wise and the system is stirred at rt overnight. The solution is poured over excess of saturated solution of ammonium chloride and is extracted thrice with ethyl ether. After washing with brine, the solution is dried and concentrated to give a reddish residue which is purified by column chromatography (Cl$_3$CH/hexane from 1:3 to 1:1) to give 2.6 g of the title compound (75% yield) as a white solid.

Intermediate 161 trans-4-[(tert-butoxycarbonyl)(methyl)amino]cyclohexyl 9-methyl-9H-xanthene-9-carboxylate 405 mg (1.59 mmol) of the intermediate 160 and 420 mg (1.83 mmol) of the intermediate 3 are dissolved in 40 ml of toluene. 32 mg (0.80 mmol) of sodium hydride (60%

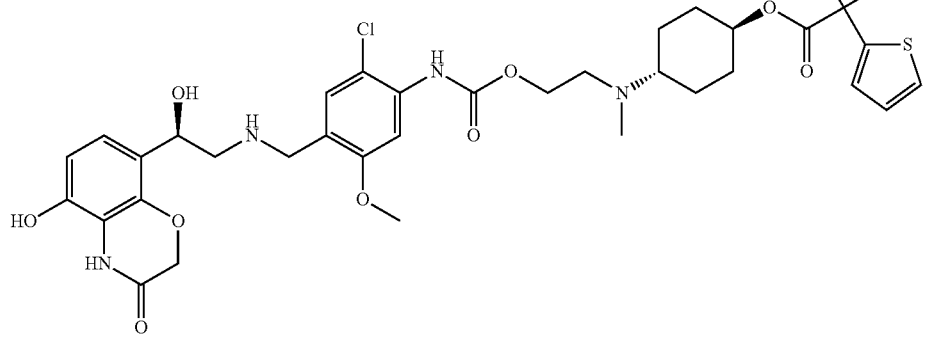

paraffin suspension) are added and the system is distilled at 150° C. (external bath) till 30 ml of toluene are collected. 30 additional ml of toluene are added and the distillation prosecuted again. The same operation is repeated twice. The solvent is eliminated in vacuo and the residue fractionated in ethyl ether/4% aqueous NaHCO3. The organic layer is washed with brine, dried and concentrated to give 650 mg of a yellowish oil containing a 83% of title compound which is used per se in te next synthetic step.

Intermediate 162 trans-4-(methylamino)cyclohexyl 9-methyl-9H-xanthene-9-carboxylate 650 mg (1.19 mmol) of intermediate 161 (83% purity) are dissolved in 2.5 ml of dioxane. 0.5 ml (2.0 mmol) of 4M solution of HCl in dioxane are added and the system is stirred at rt for 2 hr. 0.5 additional ml of 4M HCl in dioxane are added followed by overnight stirring. Ethyl ether and water are added and the aqueous layer is basified to pH 9 with potassium carbonate and extracted twice with ethyl acetate. After drying and concentrating 318 mg (63% yield) of the title compound are obtained (100% purity) as a light brown oil.

Intermediate 163 trans-4-[(9-bromononyl)(methyl)amino]cyclohexyl 9-methyl-9H-xanthene-9-carboxylate 318 mg (0.90 mmol) of intermediate 162 are dissolved in 12 ml THF 0.728 ml (3.61 mmol) of 1,9-dibromononane and 0.19 ml (1.36 mmol) of triethylamine are added and the system is stirred at 50° C. for 24 hr. 0.19 additional ml of triethylamine are added and the stirring at 50° C. prosecuted overnight. After a new addition of 1,9-dibromononane (0.911 ml; 4.5 mmol) and 72 hr of stirring at 70° C. the solvents are eliminated, ethyl ether is added and the solids (trimethylammonium hydrobromide) filtered. The filtrate is concentrated and purified via SP1 chromatography to give 220 mg (42% yield) of the title compound.

Intermediate 164 trans-4-[(9-{[(2R)-2-{[tert-butyl(dimethyl)silyl]oxy}-2-(8-hydroxy-2-oxo-1,2-dihydroquinolin-5-yl)ethyl]amino}nonyl)(methyl)amino]cyclohexyl 9-methyl-9H-xanthene-9-carboxylate 220 mg (0.40 mmol) of intermediate 163, 156 mg (0.40 mmol) of (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) and 140 mg (1.66 mmol) of sodium hydrogen carbonate in 5 ml dimethylacetamide are stirred at 60° C. overnight. The solvent is eliminated in vacuo and the residue is fractionated with ethyl acetate/water. The organic layer is washed with water, dried and concentrated to give a residue which is purified chromatographically (SP1 system eluting with Cl3CH to Cl3CH/EtOH 9:1) to give 93 mg (29% yield) of the title compound.

Example 27 trans-4-[(9-{[(2R)-2-hydroxy-2-(8-hydroxy-2-oxo-1,2-dihydroquinolin-5-yl)ethyl]-amino}nonyl)(methyl)amino]cyclohexyl 9-methyl-9H-xanthene-9-carboxylate

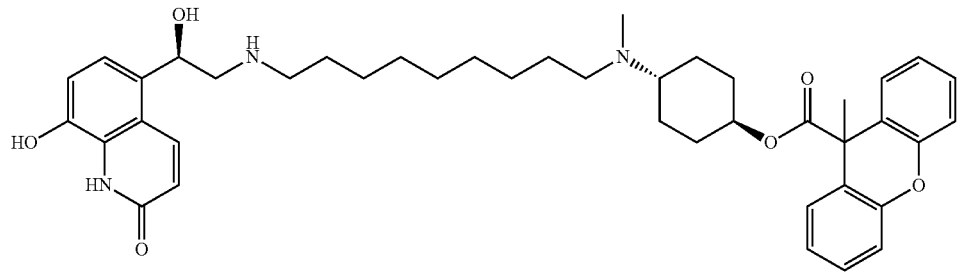 [SMILES: CN(CCCCCCCCCNC[C@H](O)c1ccc(O)c2[nH]c(=O)ccc12)[C@H]1CC[C@H](OC(=O)C2(C)c3ccccc3Oc3ccccc32)CC1]

68 mg (0.08 mmol) of the intermediate 164 are dissolved in 2 ml of THF. 0.068 ml (0.42 mmol) of triethylamine trihydrofluoride complex and the system is stirred under argon at room temperature for 4 hr. The supernatant is discarded and the remaining yellowish oil is washed again with more THF by stirring overnight. The solvent is again discarded and the residue dried overnight in a vacuum dessicator at 30° C. 30.0 mg (46% yield) of the title compound as a solid (100% purity UPLC) were obtained.

LRMS (m/z): 696(M+1)$^+$.

$^1$H NMR (300 MHz, DMSO-d$_6$) □ ppm 1.17-1.37 (br.s., 18H) 1.44-1.65 (br.s., 4H) 1.67-1.79 (c.s., 6H) 2.11 (s., 3H) 2.25-2.38 (br.s., 4H) 2.75 (t., 2H) 2.87 (br.s., 2H) 3.60 (m., 1H) 4.57 (m., 1H); 5.18 (m., 1H), 6.53 (d., J=12 Hz, 1H), 6.93 (d., J=6Hz, 1H) 7.06-7.16 (c.s., 5H) 7.23-7.34 (c.s., 4H) 8.16 (d., J=6Hz, 1H).

Intermediate 165 trans-4-[(tert-butoxycarbonyl)(methyl)amino]cyclohexyl (2R)-cyclopentyl (hydroxy)phenylacetate To a solution of 1500 mg (6.81 mmol) of (2R)-cyclopentyl(hydroxy)phenylacetic acid (pre-paration described in J. Med. Chem, 1977, 20(12), 1612-17 and WO2002/053564) in 20 ml THF are added 1320 mg (8.14 mmol) of carbonyldiimidazole. After stirring for 2 hr at rt, 1000 additional mg of carbonyldiimidazol are added and the stirring is prosecuted for 2 additional hr. To a solution of 2810 mg (12.25 mmol) of intermediate 3 in 20 ml THF 300 mg (7.50 mmol) of 60% sodium hydride are added and the solution is stirred for 3 hrs at rt. The solution of the imidazolide is added over the solution of the alcoxyde and the re-sulting system is stirred at rt overnight. The solution is poured over excess ice/water and is extracted with ethyl ether. The organic solution is successively washed with 4% Na—

HCO3 solution, water and brine. After drying and concentrating in vacuo the residue is purified using preparative reversed-phase HPLC (hexane to Cl3CH) to give 1900 mg (65% yield) of the pure title compound.

LRMS (m/z): 432 (M+1)+.

Intermediate 166 trans-4-(methylamino)cyclohexyl (2R)-cyclopentyl(hydroxy)phenylacetate 2.08 g (4.82 mmol) of intermediate 165 are dissolved in 60 ml dioxane. 9.50 ml of 4N hy-drogen chloride in dioxane are added and the system is stirred at rt for 72 hr. After frac-tionating in diethyl ether/water the aqueous phase is washed with ether, basified with solid potassium carbonate and extracted with ethyl acetate. After drying and concentrating 1.37 g of the pure title compound are obtained as a colorless oil.

LRMS (m/z): 332 (M+1)+.

Intermediate 167 trans-4-[(2-hydroxyethyl)(methyl)amino]cyclohexyl (2R)-cyclopentyl(hydroxy)phenylacetate Starting from intermediate 166 and following the same procedure described as for inter-mediate 60 the title compound was obtained as a colorless oil in 58% yield.

LRMS (m/z): 376 (M+1)+.

Intermediate 168 trans-4-[{2-[({[2-chloro-4-(hydroxymethyl)-5-methoxyphenyl]amino}carbonyl)oxy]ethyl}(methyl)amino]cyclohexyl (2R)-cyclopentyl(hydroxy)phenylacetate Starting from intermediates 167 and 59 and following the same procedures described as for intermediates 61 and 62 the title compound was obtained as a colorless oil in 30% yield using preparative reversed-phase HPLC (hexane/diethyl ether 10:0 to 5:5).

LRMS (m/z): 589 (M+1)+.

Intermediate 169 trans-4-[[2-({[(2-chloro-4-formyl-5-methoxyphenyl)amino]carbonyl}oxy)ethyl](methyl)amino]cyclohexyl (2R)-cyclopentyl(hydroxy)phenylacetate Starting from intermediate 168 and following the same procedure described as for inter-mediate 43 the title compound was obtained in 77% yield.

LRMS (m/z): 587 (M+1)+.

Intermediate 170 trans-4-[{2-[({4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}carbonyl)oxy]ethyl}(methyl)amino]cyclohexyl (2R)-cyclopentyl(hy-droxy)phenylacetate Starting from intermediate 169 and (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) and following the same procedure described as for intermediate 64 (purification by preparative reversed-phase HPLC (CH2Cl2/EtOH 10:0 to 9:1) the title compound was obtained in 54% yield.

LRMS (m/z): 905 (M+1)+.

Example 28 trans-4-[{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}-(methyl)amino]cyclohexyl (2R)-cyclopentyl(hydroxy)phenylacetate

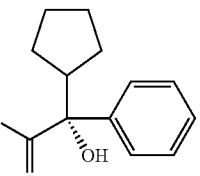

Starting from intermediate 170 and following the same procedure described as for exam-ple 12 the title compound was obtained in 37% yield.

LRMS (m/z): 791 (M+1)+.

$^1$H-NMR (300 MHz, DMSO-d6) □□ppm: 1.12-1.61 (m, 12 H), 1.63-1.82 (m, 3 H), 1.86-1.95 (m, 1 H), 2.21 (s, 3 H), 2.37-2.45 (m, 1 H), 2.60-2.68 (m, 2 H), 2.69-2.89 (m, 3 H), 3.74 (s, 5 H), 4.05-4.14 (t, 2 H), 4.50-4.62 (m, 1 H), 5.06-5.14 (m, 1 H), 5.54 (s, 1 H), 6.50 (d, J=9.89 Hz, 1 H), 6.92 (d, J=7.97 Hz, 1 H), 7.07 (d, J=7.97 Hz, 1 H), 7.16-7.40 (m, 5 H), 7.53-7.60 (m, 2 H), 8.11 (d, J=9.89 Hz, 1 H), 8.97 (s, 1 H), 10.35 (br. s., 1 H).

Intermediate 171 trans-4-[(tert-butoxycarbonyl)(methyl)amino]cyclohexyl (2S)-cyclopentyl (hydroxy)-2-thienylacetate To a solution of 450 mg (1.99 mmol) of (2S)-cyclopentyl (hydroxy)2-thienylacetic acid (preparation described in J. Med. Chem. 1977, 20(12), 1612-17 and WO2002/053564) in 6 ml THF are added 387 mg (2.39 mmol) of carbonyldiimidazole. After stirring for 3 hr at rt, 387 additional mg of carbonyldiimidazol are added and the stirring is prosecuted for 2 additional hr. To a solution of 822 mg (3.58 mmol) of intermediate 3 in 2 ml THF 87 mg (2.18 mmol) of 60% sodium hydride are added and the solution is stirred for 5 hrs at rt. The solution of the imidazolide is added over the solution of the alcoxyde and the resulting system is stirred at rt overnight. The solution is poured over excess ice/water and is ex-tracted with ethyl ether (2×100 ml). The organic solution is successively washed with 4% NaHCO3 solution, water and brine. After drying and concentrating in vacuo 1048 mg of a yellowish oil containing 60% of the title product are obtained and used per se in the next synthetic step.

Intermediate 172 trans-4-(methylamino)cyclohexyl (2S)-cyclopentyl(hydroxy)2-thienylacetate 1048 mg (1.44 mmol) of intermediate 171 are dissolved in 24 ml dioxane. 4.80 ml of 4N hy-drogen chloride in dioxane are added and the system is stirred at rt for 24 hr. After fractionating in diethyl ether/water the aqueous phase is washed with ether, basified with solid potassium hydrogen carbonate and extracted with ethyl acetate. After drying and concentrating 295 mg (59% yield) of the pure title compound are obtained as a colorless oil.
LRMS (m/z): 338 (M+1)+.

Intermediate 173 trans-4-[(2-hydroxyethyl)(methyl)amino]cyclohexyl (2S)-cyclopentyl(hydroxy)2-thienylacetate Starting from intermediate 172 and following the same procedure described as for inter-mediate 60 the title compound was obtained as a colorless oil in 73% yield.
LRMS (m/z): 382 (M+1)+.

Intermediate 174 trans-4-[{2-[({[2-chloro-4-(hydroxymethyl)-5-methoxyphenyl]amino}carbonyl)oxy]ethyl}(methyl)amino]cyclohexyl (2S)-cyclopentyl(hydroxy)2-thienylacetate Starting from intermediates 173 and 59 and following the same procedures described as for intermediates 61 and 62 the title compound was obtained as a colorless oil in 50% yield using preparative reversed-phase HPLC (Cl2CH2/MeOH 10:0 to 9:1).
LRMS (m/z): 595 (M+1)+.

Intermediate 175 trans-4-[[2-({[(2-chloro-4-formyl-5-methoxyphenyl)amino]carbonyl}oxy)ethyl](methyl)amino]cyclohexyl (2S)-cyclopentyl(hydroxy)2-thienylacetate Starting from intermediate 174 and following the same procedure described as for inter-mediate 43 the title compound was obtained in 86% yield.
LRMS (m/z): 593 (M+1)+.

Intermediate 176 trans-4-[{2-[({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}carbonyl)oxy]ethyl}(methyl)amino] cyclohexyl (2S)-cyclopentyl(hydroxy)2-thienylacetate Starting from intermediate 175 and (2R)-2-{[tert-butyl(dimethyl)silyl]oxy}-2-(8-hydroxy-2-oxo-1,2-dihydroquinolin-5-yl)ethanaminium acetate (prepared according to preparation 8 from US20060035931) and following the same procedure described as for intermediate 64 (purification by preparative reversed-phase HPLC (CHCl3/EtOH 10:0 to 9:1) the title compound was obtained in 72% yield.
LRMS (m/z): 911 (M+1)+.

Example 29 trans-4-[{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methyl)amino]cyclohexyl (2S)-cyclopentyl(hydroxy)2-thienylacetate

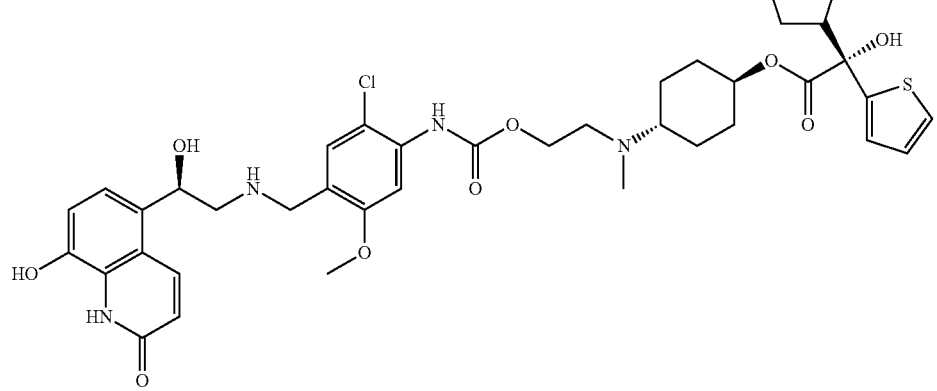

Starting from intermediate 176 and following the same procedure described as for exam-ple 12 the title compound was obtained in 59% yield.

LRMS (m/z): 797 (M+1)+.

$^1$H-NMR (300 MHz, DMSO-d6) ☐ ppm: 1.18-1.58 (m, 12 H), 1.65-1.77 (m, 2 H), 1.78-1.86 (m, 1 H), 1.89-2.00 (m, 1 H), 2.22 (s, 3 H), 2.37-2.47 (m, 1 H), 2.61-2.69 (m, 3 H), 2.70-2.77 (m, J=5.22 Hz, 2 H), 3.74 (s, 3 H), 3.77 (s, 2 H), 4.10 (t, J=5.77 Hz, 2 H), 4.53-4.65 (m, 1 H), 5.11 (t, J=5.91 Hz, 1 H), 5.94 (s, 1 H), 6.49 (d, J=9.89 Hz, 1 H), 6.89-6.98 (m, 2 H), 7.05 (s, 1 H), 7.06-7.09 (m, 1 H), 7.20 (s, 1 H), 7.37 (s, 1 H), 7.38 (d, J=1.10 Hz, 1 H), 8.12 (d, J=9.89 Hz, 1 H), 8.99 (s, 1 H) 10.37 (br. s., 1 H).

Biological Tests

Test 1: Human Adrenergic $\beta_1$ and $\beta_2$ Receptor Binding Assays

The study of binding to human adrenergic beta1 and beta2 receptors was performed using commercial membranes prepared from Sf9 cells where they are overexpressed (Perkin Elmer). The membrane suspensions (16 µg/well for beta1 and 5 µg/well for beta2) in assay buffer (75 mM Tris/HCl with 12.5 mM MgCl2 and 2 mM EDTA pH=7.4) were incubated with 0.14 or 0.6 nM of 3H-CGP12177 (Amersham) for beta 1 and beta 2 receptors respectively in a final volume of 250 µl, in GFC Multiscreen 96 well plates (Millipore) previously treated with assay buffer containing 0.3% PEI (Sigma). Non specific binding was measured in the presence of 1 µM propanolol. Incubation was maintained for 60 minutes at room temperature and with gentle shaking. The binding reactions were terminated by filtration and washing with 2.5 volumes of Tris/HCl 50 mM pH=7.4. The affinity of each test compound to the receptor was determined by using ten different concentrations ran in duplicate. IC50s were calculated using Activity Base software from IDBS and the four parameters-log equation.

Preferred compounds of the present invention were found to have $IC_{50}$ values less than 20 nM for $\beta_2$ receptor, preferably less than 10 nM.

Test 2: Human Muscarinic $M_1$, $M_2$, $M_3$, $M_4$ and $M_5$ Receptors Binding Assays The study of binding to human muscarinic M1, M2, M3, M4 and M5 receptors was performed using commercial membranes (Perkin Elmer) prepared from CHO-K1 cells. Radioligand binding experiments were conducted in 96 polypropylene well plates in a total volume of 200 µl. All reagents were dissolved in assay binding buffer (PBS with calcium and magnesium, SIGMA), except compounds that were dissolved in DMSO 100%. Non-specific binding (NSB) was measured in the presence of 1 µM atropine. [3H]-NMS was used as the radioligand at a concentration of 1 nM for M2, M3 and M5 and 0.3 nM for M1 and M4, [3H]-NMS and antagonists were incubated with membranes that express human muscarinic receptors M1, M2, M3, M4 and M5 at concentrations of 8.1, 10, 4.9, 4.5 and 4.9 µg/well, respectively.

After an incubation period of two hours with gentle shaking, 150 µl of the reaction mix were transferred to 96 GF/C filter plates (Millipore), previously treated with wash buffer (Tris 50 mM; NaCl 100 mM; pH:7.4), containing 0.05% PEI (Sigma) during one hour. Bound and free [3H]-NMS were separated by rapid vacuum filtration in a manifold from Millipore and washed four times with ice cold wash buffer. After drying 30 min, 30 µl of OPTIPHASE Supermix were added to each well and radioactivity quantified using a Microbeta microplate scintillation counter.

The affinity of each test compound to the receptors was determined by using ten different concentrations ran in duplicate. IC50s were calculated using Activity Base software from IDBS and the four parameters-log equation.

Preferred compounds of the present invention show $IC_{50}$ values for the $M_3$ receptor between 0.1 and 10 nM, preferably between 0.1 and 5 nM, more preferably between 0.1 y 2 nM.

| Example | Binding $IC_{50}$, nM | |
| --- | --- | --- |
| | $\beta_2$ | M3 |
| 1 | 6.4 | 0.2 |
| 2 | 36 | 1.3 |
| 9 | 8.5 | 1.1 |
| 10 | 6.7 | 2.2 |
| 12 | 1.6 | 1.6 |
| 13 | 2.2 | 2.1 |
| 15 | 2.1 | 1.0 |
| 16 | 4.8 | 2.0 |
| 18 | 13 | 1.6 |
| 20 | 5.3 | 0.7 |
| 22 | 4.5 | 1.4 |
| 25 | 9.6 | 0.3 |
| 26 | 0.38 | 1.7 |
| 28 | 1.3 | 8.5 |
| 29 | 1.1 | 3.8 |

Test 3: $\beta_2$ Adrenoreceptor Agonist Activity and Duration of Action on Isolated Guinea-Pig Tracheal Rings Stock drug solutions were prepared by dissolving the compounds in distilled water. Some of them were dissolved using a maximum of 10% polyethylene glycol 300 and/or 1% of HCl 1 N. Isoprenaline hemisulfate was supplied by Sigma (code I 5752) and dissolved in distilled water. Stock solutions were then diluted in Krebs Henseleit solution (NaCl 118 mM, KCl 4.7 mM, CaCl2 2.52 mM, MgSO4 1.66 mM, NaHCO3 24.9 mM, KH2PO4 1.18 mM, glucose 5.55 mM, sodium pyruvate 2 mM) to prepare different concentration ranges per each compound.

The activity of compounds in tracheal ring was assessed according to Cortijo et al. (Eur J Pharmacol. 1991, 198, 171-176). Briefly, adult, male guinea pigs (400-500 g) were sacrificed by a blow to the head with immediate exsanguinations (abdominal aorta). Trachea was excised and placed into Krebs solution in a Petri dish. The adherent connective tissue was dissected away and the lumen gently flushed with Krebs solution. Each trachea was dissected into single rings. First, cotton thread was attached to the cartilage at both sides of the smooth muscle. The rings were opened by cutting through the cartilage on the side opposite to the smooth muscle band. Then, one end of the ring was attached to the strain gauge and the other end was attached to the organ-bath under a resting tension of 1 g and changes in tension of the rings were measured using an isometric transducer TRI 201, 202 (Panlab, Spain). Tissues were than left for one hour to stabilize suspended in water jacketed organ baths containing 30 ml of Krebs solution at 37° C. bubbled with 5% CO2 in oxygen.

At the beginning of the experiment isoprenaline was added at a concentration of 0.1 µM to test tracheal ring relaxation. Preparations were then washed twice with Krebs solution and left to recover for 15-30 min. For each compound, a range of increasing and accumulative concentrations (0.01 nM to 0.1 µM) was administered with a maximum waiting time of 30 min between each administration. After the maximum effect (achievement of complete relaxation), ring preparations were washed every 15 min during 1 hour. At the and of the experiment, 0.1 µM of isoprenaline was added to each preparation to obtain maximum relaxation level.

Agonist activity was determined by assaying accumulative increasing concentrations of test compounds prepared in the Krebs solution. The magnitude of each response was measured and expressed as a percentage versus the maximum relaxation induced by isoprenaline. Potency values for the test compounds were expressed in absolute terms (concentration required to induce a 50% relaxation, $EC_{50}$).

The time spanning from the end of drug addition to attaintment of 50% recovery (T50 offset, with a maximum time of 60 min) was also determined per each compound.

Preferred compounds of the present invention show $EC_{50}$ values less than 3 nM.

Test 4: $\beta_1$ Adrenoreceptor Agonist Activity in the Electrically Stimulated Rat Left Atria Stock drug solutions were prepared dissolving the compounds in distilled water. Some of them were dissolved using a maximum of 10% polyethylene glycol 300 and/or 1% of HCl 1 N. Isoprenaline hemisulfate was supplied by Sigma (code I 5752) and dissolved in distilled water. Stock solutions were then diluted in Krebs Henseleit solution (NaCl 118 mM, KCl 4.7 mM, CaCl2 2.52 mM, MgSO4 1.66 mM, NaHCO3 24.9 mM, KH2PO4 1.18 mM, glucose 5.55 mM, sodium pyruvate 2 mM) to prepare different concentration ranges per each compound.

Male Wistar rats (150-250 g) were euthanized by stunning and cervical dislocation. Heart was removed and placed in the Krebs solution previously described. The left atria was dissected and suspended in water jacketed organ baths containing 30 ml of Krebs solution at 37° C. bubbled with 5% CO2 in oxygen. The isolated left atria was connected with cotton thread to a isometric force transducer TRI 201, 202 (Panlab, Spain) under a resting tension of 0.5 g. Transducers were connected to a PowerLab system 8/30 (ADInstruments, Australia) to measure changes in tension. Tissues were paced with afield stimulator Hugo Sachs Electronic type D7806 (Harvard Apparatus, Germany) at a frequency of 1 Hz (supra-maximal voltage, 0.1 ms) and than left for 45 minutes to stabilize for the measurements of basal contractions.

Isoprenaline 1 µM was added to the bath twice to test atria response. After test atria response, organs were washed twice with Krebs solution and left to recover for approximately 15 minutes. Compounds were assessed in a range of increasing and cumulative concentrations (1 nM to 10 µM) added every 10-15 min to allow the reading of a stable effect. After the last compound concentration assessment atria's were washed with Krebs, and isoprenaline 1 µM was added again to check whether the maximum contraction was still achieved.

The $\beta 1$ activity was determined through the quantification of the contraction produced by each dose of compound with respect to the response evoked by isoprenaline 1 µM that was considered as maximal and therefore equal to 100%. The corresponding cumulative response curves (CRCs) were built and potency values were expressed as the concentration required to induce the 50% of maximum contractile effect ($EC_{50}$).

Preferred compounds of the present invention show ratios more than 1000 fold between $EC_{50}$ values for the tests 4 and 3.

Test 5: Muscarinic Antagonist and Beta-Adrenergic Agonist Activity, Onset and Offset of Action on Electrically-Stimulated Guinea-Pig Trachea Adult, male guinea pigs (400-500 g) were euthanized by a blow to the head with subsequent exsanguinations. Trachea was excised and placed in Krebs solution in a Petri dish. The adherent connective tissue was dissected away and the lumen gently flushed with Krebs solution. Each trachea was dissected into rings containing 3-4 cartilage bands and the rings opened to form strips by cutting through the cartilage on the side opposite to the smooth muscle band. A long, cotton thread was attached to the cartilage at one end of the strip to attach the strain gauge, and a cotton loop on the other end for anchoring the tissue in the superfusion chamber.

Methodology for tissue superfusion has been described previously (Coleman & Nials, 1989). Preparations were mounted in a Superfusion bath Type 840 (Harvard Apparatus, Germany) under a resting tension of 1 g. For the entire duration of the experiment trachea strips were superfused at a rate of 2 ml min-1 with oxygenated (5% CO2 in O2) Krebs Henseleit solution at 37° C., containing 2.8 µM indomethacin. Bipolar platinum electrodes were positioned in parallel with and in close proximity to the superfused tissue. Tissues were then left for one hour to stabilize.

This methodology allows us to reveal the global relaxant activities, including both muscarinic antagonism and beta 2 agonism. In order to unmask the muscarinic antagonist activity of compounds, a beta antagonist (Propranolol at a final concentration of 1 µM) was added to the Krebs solution. Krebs solution containing propranolol was perfunded throughout all the assay.

Electrical stimulation was delivered as square wave pulses of 10-second trains every 2 minutes at a frequency of 5 Hz and a duration of 0.1 ms (Coleman & Nials, 1989). In each experiment, the voltage was chosen following construction of a voltage-dependent response curve from 8-16 V and selecting a supramaximal dose within 10-15% of the maximum response. To establish a baseline, trachea strips were stimulated for a minimum of 20 minutes (10 peaks) at this supramaximal voltage.

Stock drug solutions were prepared dissolving the compounds in distilled water. Some of them were dissolved using a maximum of 10% polyethylene glycol 300 and/or 1% of HCl 1 N. Stock solutions were then diluted in Krebs Henseleit to prepare different concentration ranges per each compound.

Activities were determined infusing increasing concentrations of test compound during 60 minutes. The magnitude of each response was measured and expressed as a percentage of inhibition of the baseline electrically-induced contractile response.

Potency values for the muscarinic antagonist beta-adrenergic agonists were expressed in absolute terms (concentration required to induce a 50% inhibition, $EC_{50}$). Duration of action was determined after infusing 60 min, a test compound concentration able to relax between 50%-80% of the maximal contraction.

$T_{50}$ onset is defined as the time spanning from drug addition to 50% attainment the maximum response ($T_{max}$). $T_{max}$ is defined as the time spanning from drug addition to attainment the maximum response. $T_{50}$ offset is defined as the time spanning from the end of drug addition to attainment of 50% relaxation recovery, Offset of action was also expressed as the percentage of recovery reached 8 h after the end of drug addition.

Selected compounds of the present invention show $EC_{50}$ values less than 5 nM for the global activity and less than 10 nM for the M3 assessment, with $T_{50}$ offset values more than 450 minutes.

Test 6: Acetylcholine-Induced or Histamine-Induced Bronchoconstriction in Anesthetized Guinea-Pig This in vivo assay was used to assess the bronchoprotective effects of test compounds exhibiting both muscarinic receptor antagonist and β2 adrenergic receptor agonist activity.

The test compounds were dissolved in distilled water. Some of them required to be dissolved using a maximum of 1% HCl or 1% NaOH and/or 2% polyethylene glycol 300. Acetylcholine chloride, histamine dihydrochloride and propranolol hydrochloride were supplied by Sigma-Aidrich (St. Louis, Mo., USA) and dissolved in saline solution.

Male guinea-pigs (450-600 g) were maintained at a constant temperature of 22±2° C., humidity 40-70% with 10 cycles of room air per hour. They were subjected to 12 hour cycles of artificial light (from 7 h am to 7 h pm) and underwent a minimum acclimatization period of 5 days before they were dosed with test compounds. The animals were fasted 18 hours before the experiment with water ad libitum.

Guinea pigs were exposed to an aerosol of a test compound or vehicle. These aerosols were generated from aqueous solutions using a Devilbiss nebuliser (Model Ultraneb 2000, Somerset, Pa., USA). A mixture of gases ($CO_2=5\%$, $O_2=21\%$, $N_2=74\%$) was flown through the nebuliser at 3 L/minute, This nebuliser was connected to a methacrylate box (17×17×25 cm) where the animals were placed one per session. Every guinea pig remained in the box for a total of 10 minutes. Either compound or vehicle was nebulised for 60 seconds at time 0 and 5 minutes (approximately 5 mL of solution was nebulised).

Concentrations between 0.1 and 100 μg/ml of the aerosolized compounds were administered. The bronchoprotective effects of test compounds were evaluated one hour or twenty four hours post-dose with a FinePointe™ RC System (Buxco Research Systems; Wilmington, N.C., USA).

The guinea pigs were anesthetized with an intramuscular injection of ketamine (69.8 mg/Kg), xylazine (5.6 mg/Kg) and acepromazine (1.6 mg/Kg) at a volume of 1 ml/kg. If required, anesthesia was extended by additional intramuscular injections of the aforementioned anesthetic mixture. Animals were then cannulated and placed into a plethysmograph (#PLY4214, Buxco Research Systems; Wilmington, N.C., USA) where temperature was maintained at 37° C. The ventilation pump was set to a tidal volume of 10 ml/kg at a rate of 60 breaths/min, and an oesophageal tube was inserted to measure pulmonary driving pressure. The jugular vein was also cannulated with a polyethylene catheter (Portex Ld.) to allow delivery of an intravenous bolus of acetylcholine or histamine at 3-min intervals. Once the chamber was sealed, flows were measured by a pneumotacograph located in the wall of the plethysmograph. These variations in flow and pressure were registered with a FinePointe™ RC System (Buxco Research Systems; NC, USA), assessing the airway resistance (RI) of the anesthetized animals (BioSystem XA software, version 2.10 for Windows; Buxco Research Systems; NC, USA).

As soon as baseline values were in the range of 0.1-0.3 cmH2O/mL per second of airway resistance, the pulmonary measurement was initiated. After a stabilization period (3-5 minutes), bronchoconstriction was induced by two intravenous bolus of acetylcholine (10 and 15 μg/kg) or histamine (5 and 10 μg/kg). The bronchoconstriction response to the 15 μg/kg acetylcholine dose was used to calculate the total inhibitory effect of each treated group, compared to the response of its respective control group. When histamine was injected i.v. (10 μg/kg) to induce the bronchoconstriction, the inhibition of this response in treated groups reflected the β2 adrenergic receptor agonist activity. Additionally, in order to isolate the muscarinic antagonist activity in the acetylcholine-induced bronchoconstriction model, the animals were given propanolol (5 mg/kg i.v.), a compound that blocks β receptor activity, 15 minutes prior to challenge with acetylcholine.

The overall bronchocoprotective effect of every inhaled compound and the dissection of their β2 agonist and antimuscarinic activities was then established by assessing the concentration of test compound that causes a 50% of inhibition of the bronchoconstriction (IC50) in three different conditions: the β2 adrenergic receptor agonist activity after histamine-induced bronchoconstriction, the muscarinic receptor antagonist activity when propranolol is administered prior to acetylcholine-induced bronchoconstiction, and the combination of both activities when the acetylcholine-induced bronchoconstriction is inhibited.

The effect of all the compounds was tested 1 h and 24 h post-dose in order to evaluate the duration of action of the overall bronchoprotective activity as well as the individual $β_2$ adrenergic receptor agonist and the muscarinic receptor antagonist components.

Selected compounds of the present invention show $IC_{50}$ values less than 5 □g/m1 at 1 hr and less than 25 □g/ml at 24 hr.

Pharmaceutical Compositions

The pharmaceutical formulations may conveniently be presented in unit dosage form and may be prepared by any of the methods well known in the art of pharmacy; All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Each capsule or cartridge may generally contain between 2 μg and 150 μg of each therapeutically active ingredient. Alternatively, the active ingredient(s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices, For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e. g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e. g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described in the following patent applications Nos.: WO97/000703, WO03/000325, WO03/061742 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e. g. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with.

Such atomisers are described, for example, in PCT Patent Application No. WO 91/14468 and International Patent Application No. WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient(s) and a suitable propellant such as a fluorocarbon or hydrogen-containing chlorofluorocarbon or mixtures thereof, particularly hydrofluoroalkanes, a, g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants, for example, oleic acid or lecithin and cosolvents, for example, ethanol. Pressurised formulations will generally be retained in a canister (for example, an aluminium canister) closed with a valve (for example, a metering valve) and fitted into an actuator provided with a mouthpiece.

Medicaments for administration by inhalation desirably have a controlled particle size. The optimum particle size for inhalation into the bronchial system is usually 1-10μ, preferably 2-5μ. Particles having a size above 20μ are generally too large when inhaled to reach the small airways. To achieve these particle sizes the particles of the active ingredient as produced may be size reduced by conventional means, for example, by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e. g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit contains suitably from 0.5 μg to 500 μg, and preferably from 5 μg to 100 μg of a compound according to the invention.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

Examples of suitable PDE4 inhibitors that can be combined with compounds of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluoro-benzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethyl-carbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)-naphthalen-1-yl]-1-(2-methoxyethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl]-cyclopropanecarboxylic acid (MK-0873), CDC-801, UK-500001, BLX-914, 2-carbomethoxy-4-cyano-4-(3-cyclopropylmethoxy-4-difluoromethoxy-phenyl)-cyclohexan1-one, cis [4-cyano-4-(3-cyclopropylmethoxy-4-difluoromethoxyphenyl)-cyclohexan-1-ol, CDC-801, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the salts claimed in the PCT patent applications number WO03/097613, WO2004/058729, WO 2005/049581, WO 2005/123693 and WO 2005/123692

Examples of suitable corticosteroids and glucocorticoids that can be combined with compounds of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone acepnate, dexamethasone palmitoate, tipredane, hydrocortisone acepnate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, Desisobutyrylciclesonide, hydrocortisone acetate, hydrocortisone sodium succinate, NS-126, prednisolone sodium phosphate and hydrocortisone probutate, Prednisolone sodium metasulfobenzoate and clobetasol propionate.

Particularly preferred pharmaceutical composition according to the invention comprises a compound of formula (I) and a therapeutically effective amount of one or more additional therapeutic agents selected from the group consisting of mometasone furoate, ciclesonide, budesonide, fluticasone propionate, fluticasone furoate, rolipram, roflumilast, cilomilast and the compounds claimed in the PCT patent applications number WO03/097613, WO2004/058729, WO 2005/049581, WO 2005/123693 and WO 2005/123692

Still particularly preferred pharmaceutical composition according to the invention comprise a compound of formula (I) and a therapeutically effective amount of one or more additional therapeutic agents selected from the group consisting of mometasone furoate, ciclesonide, budesonide, fluticasone propionate, fluticasone furoate, rolipram, roflumilast and cilomilast Thus, in one aspect of the invention, the composition comprises a compound of formula (I) and a corticosteroid. Particularly preferred corticosteroids are those selected from the group consisting of mometasone furoate, ciclesonide, budesonide, fluticasone furoate and fluticasone propionate.

In another aspect of the invention, the composition comprises a compound of formula (I) and a PDE4 inhibidor. Particularly preferred PDE4 inhibitors are those selected from the group consisting of rolipram, roflumilast, cilomilast and the compounds claimed in the PCT patent applications number WO03/097613, WO2004/058729, WO 2005/049581, WO 2005/123693 and WO 2005/123692. The composition may further comprise a corticosteroid selected from the group consisting of mometasone furoate, ciclesonide, budesonide, fluticasone furoate and fluticasone propionate.

In another preferred embodiment of the present invention, the composition comprises a compound of formula (I) and a therapeutically effective amount of a mometasone furoate. Optionally, the composition further comprises a PDE4 inhibitor.

The combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combination and the PDE4 inhibitors, corticosteroids or glucocorticoids may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other(s) later in the day. Or in another scenario, one or two actives could be taken twice daily and the other(s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive king diseases or for the treatment of asthma.

Additional suitable carriers for formulations of the active compounds of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

FORMULATION EXAMPLE

Formulation Example 1

(Oral Suspension)

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2

(Hard Gelatine Capsule for Oral Administration)

| Ingredient | Amount |
| --- | --- |
| Active Compound | 1 mg |
| Lactose | 150 mg |
| Magnesium stearate | 3 mg |

Formulation Example 3

(Gelatin Cartridge for Inhalation)

| Ingredient | Amount |
| --- | --- |
| Active Compound (micronized) | 0.2 mg |
| Lactose | 25 mg |

Formulation Example 4

(Formulation for Inhalation with a DPI)

| Ingredient | Amount |
| --- | --- |
| Active Compound (micronized) | 15 mg |
| Lactose | 3000 mg |

Formulation Example 5

(Formulation for a MDI)

| Ingredient | Amount |
| --- | --- |
| Active Compound (micronized) | 10 g |
| 1,1,1,2,3,3,3-heptafluoro-n-propane | q.s. to 200 ml |

The invention claimed is:

1. A compound of formula (I), or pharmaceutically acceptable salt or solvate or deuterated derivative thereof:

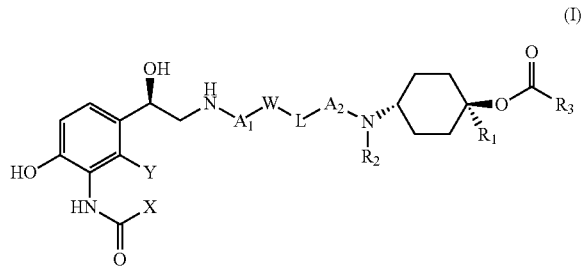

wherein:
X together with Y form a —CH=CH— group;
R₁ is a hydrogen atom;
R₂ is a methyl group;
R₃ has formula:

wherein
R$^a$ represents a hydroxy group,
R$^b$ and R$^c$ are each thienyl groups, and
* is a point of attachment of R₃ to the remainder of Formula (I);
A₁ and A₂ are each independently chosen from a C$_{1-6}$ alkylene group that is unsubstituted or substituted with one or two methyl groups;
L is chosen from —O—, —NH(CO)—, or —NH(CO)O— groups; and
W is a phenylene group that is substituted with two substituents chosen from a chlorine atom, a methyl group, a methoxy group, or a cyano group.

2. The compound according to claim 1, wherein the compound is chosen from:
trans-4((3-(2-Chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexyl hydroxy(di-2-thienyl)acetate;
trans-4-[{3-[2-Chloro-4-({[(2R)-2-hydroxy-2-(8-hydroxy-2-oxo-1,2-dihydroquinolin-5-yl)ethyl]amino}methyl)-5-methoxyphenoxy]propyl}(methyl)amino]cyclohexylhydroxy(di-2-thienyl)acetate;
trans-4-[{2-[({[2-Chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}-(methyl)amino]-cyclohexyl hydroxy(di-2-thienyl)acetate;
trans-4-[(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)(methy)amino]-clohexyl hydroxy(di-2-thienyl)acetate;
trans-4-[(3-{[2-chloro-4-(2-{[(2R)-2-hydroxy-2-(8-hydroxy-2-oxo-1,2-dihydroquinolin-5-yl)ethyl]amino}ethyl)-5-methoxyphenyl]amino}-3-oxopropyl)-(methyl)amino]cyclohexyl hydroxy(di-2-thienyl)acetate;
trans-4-[{3-[2-chloro-4-{[(2R)-2-hydroxy-2-(8-hydroxy-2-oxo-1,2-dihydroquinolin-5-yl)ethyl]amino}ethyl)-5-methoxyphenoxy]propyl}(methyl)amino]cyclohexyl hydroxy(di-2-thienyl)acetate;
trans-4-[{2-[({[2-cyano-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}(methy)amino]cyclohexyl hydroxy(di-2-thienyl)acetate;
trans-4-[(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-2,2-dimethyl-3-oxopropyl)-(methy)amino]cyclohexyl hydroxy(di-2-thienyl)acetate;
trans-4-[{4-[2-chloro-4-({[(2R)-2-hydroxy-2-(8-hydroxy-2-oxo-1,2-dihydroquinolin-5-yl)ethy]amino}methyl)-5-methoxyphenoxy]buty}(methyl)amino]cyclohexyl hydroxy(di-2-thienyl)acetate;
or a pharmaceutically acceptable salt thereof.

3. The compound according to claim 2, wherein the compound is trans-4-[{2[({[2-Chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}-(methyl)amino]-cyclohexyl hydroxy(di-2-thienyl)acetate or a pharmaceutically acceptable salt thereof.

* * * * *